(12) United States Patent
Koo et al.

(10) Patent No.: US 11,246,819 B2
(45) Date of Patent: Feb. 15, 2022

(54) COMPOSITIONS AND METHODS FOR INHIBITING BIOFILM DEPOSITION AND PRODUCTION

(71) Applicant: THE TRUSTEES OF THE UNIVERSITY OF PENNSYLVANIA, Philadelphia, PA (US)

(72) Inventors: Hyun Koo, Philadelphia, PA (US); Henry Daniell, Media, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 16/301,023

(22) PCT Filed: May 12, 2017

(86) PCT No.: PCT/US2017/032437
§ 371 (c)(1),
(2) Date: Nov. 13, 2018

(87) PCT Pub. No.: WO2017/197280
PCT Pub. Date: Nov. 16, 2017

(65) Prior Publication Data
US 2019/0328643 A1 Oct. 31, 2019

Related U.S. Application Data

(60) Provisional application No. 62/335,650, filed on May 12, 2016.

(51) Int. Cl.
| | | |
|---|---|---|
| *A61P 1/02* | (2006.01) |
| *A61K 9/68* | (2006.01) |
| *A61K 8/64* | (2006.01) |
| *A61P 31/04* | (2006.01) |
| *A01N 43/40* | (2006.01) |
| *A01N 65/38* | (2009.01) |
| *A61K 8/02* | (2006.01) |
| *A61K 8/21* | (2006.01) |
| *A61K 8/49* | (2006.01) |
| *A61K 8/66* | (2006.01) |
| *A61K 9/00* | (2006.01) |
| *A61K 38/16* | (2006.01) |
| *A61K 38/47* | (2006.01) |
| *A61Q 11/00* | (2006.01) |

(52) U.S. Cl.
CPC .............. *A61K 8/645* (2013.01); *A01N 43/40* (2013.01); *A01N 65/38* (2013.01); *A01N 65/385* (2013.01); *A61K 8/0216* (2013.01); *A61K 8/21* (2013.01); *A61K 8/4926* (2013.01); *A61K 8/66* (2013.01); *A61K 9/0056* (2013.01); *A61K 9/0058* (2013.01); *A61K 38/168* (2013.01); *A61K 38/47* (2013.01); *A61P 1/02* (2018.01); *A61P 31/04* (2018.01); *A61Q 11/00* (2013.01); *C12Y 302/01003* (2013.01); *C12Y 302/01011* (2013.01); *C12Y 302/01059* (2013.01)

(58) Field of Classification Search
None
See application file for complete search history.

(56) References Cited

U.S. PATENT DOCUMENTS

| | | | |
|---|---|---|---|
| 5,741,487 A | 4/1998 | Assai et al. | |
| 2007/0140990 A1* | 6/2007 | Fetissova ............. | A61K 8/8164 424/50 |
| 2010/0184654 A1* | 7/2010 | Eckert ................ | C07K 16/1275 514/1.1 |
| 2011/0302675 A1 | 12/2011 | Daniell | |
| 2012/0189682 A1* | 7/2012 | O'Neil ................. | A61K 31/145 424/411 |
| 2013/0052182 A1 | 2/2013 | Miller | |

FOREIGN PATENT DOCUMENTS

| | | | | |
|---|---|---|---|---|
| JP | 2000-300271 | * 10/2000 | ............. | C12N 15/09 |
| WO | WO 2013/063049 | * 5/2013 | ............. | A61K 31/40 |
| WO | WO 2013/063059 | * 5/2013 | ............. | C12N 15/82 |

OTHER PUBLICATIONS

Agrawal, Pankaj et al., "Expression of Trichoderma reesei B-Mannanase in Tobacco Chloroplasts and Its Utilization in Lignocellulosic Woody Biomass Hydrolysis", PLoS ONE, 6(12): e29302 (2011).
Ajdic, Dragana et al., "Genome sequence of *Streptococcus mutans* UA159, a cariogenic dental pathogen", PNAS, 99(22): 14434-14439 (2002).
Autio-Gold, J. et al., "The Role of Chlorhexidine in Caries Prevention", Operative Dentistry, 33-6: 710-716 (2008).
Balakrishnan, Mayooran et al., "Dental caries is a preventable infectious disease", Australian Dental Journal, 45(4): 235-245 (2000).
Banas, J.A. et al., "Glucan-Binding Proteins of the Oral Streptococci", Crit. Rev. Oral Biol. Med., 14(2): 89-99 (2003).
Bowen, W.H. et al., Biology of *Streptococcus mutans*-Derived Glucosyltransferases: Role in Extracellular Matrix Formation of Cariogenic Biofilms, Craies Res., 45: 69-86 (2011).
Caufield, Page W. et al., "The Antimicrobial Approach to Caries Management", Journal of Dental Education, 65(10): 1091-1095 (2001).

(Continued)

*Primary Examiner* — Kevin S Orwig
(74) *Attorney, Agent, or Firm* — Kathleen D. Rigaut; Howson & Howson LLP

(57) ABSTRACT

The invention provides a method for combating biofilm, said method comprising contacting a biofilm with a composition comprising an effective amount of antimicrobial peptide biofilm enzyme combinations, preferably in the form of a fusion protein. The biofilm may be on an animate or inanimate surface and both medical and non-medical uses and methods are provided. In one aspect the invention provides a composition for use in the treatment or prevention of a biofilm in a subject, particularly in the oral cavity.

26 Claims, 23 Drawing Sheets

Specification includes a Sequence Listing.

(56) References Cited

OTHER PUBLICATIONS

DeGray, Gerald et al., "Expression of an Antimicrobial Peptide via the Chloroplast Genome to Control Phytopathogenic Bacteria and Fungi", Plant Physiology, 127, 852-862 (2001).
Dige, I. et al., "Actinomyces naeslundii in initial dental biofilm formation", Microbiology, 55: 2116-2126 (2009).
Dye, Bruce A. et al., "Prevalence and Measurement of Dental Caries in Young Children", Pediatric Dentistry, 37(3): 200-216 (2015).
Guo, Lihong et al., "Precision-guided antimicrobial peptide as a targeted modulator of human microbial ecology", PNAS, 112(24): 7569-7574 (2015).
Gupta, Kshitij et al., "Activation of human mast cells by retrocyclin and protegrin highlight their immunomodulatory and antimicrobial properties", Oncotarget, 6(30): 28573-28587 (2015).
Hope, C.K. et al., "Analysis of the Effects of Chlorhexidine on Oral Biofilm Vitality and Structure Based on Viability Profiling and an Indicator of Membrane Integrity", Antimicrobial Agents and Chemotherapy, 48(5): 1461-1468 (2004).
Jin, Shuangxia et al., "Engineered Chloroplast Genome just got Smarter", Trends Plant Sci., 20(10): 622-640 (2015).
Kohli, Neha et al., "Oral Delivery of Bioencapsulated Proteins Across Blood-Brain and Blood-Retinal Barriers", Molecular Therapy, 22(3): 535-546 (2014).
Koo, H. et al., "Exopolysaccharides Produced by *Streptococcus mutans* Glucosyltransferases Modulate the Establishment of Microcolonies within Multispecies Biofilms", Journal of Bacteriology, 192(12): 3024-3032 (2010).
Koo, H. et al., "The Exopolysaccharide Matrix: A Virulence Determinant of Cariogenic Biofilm", J. Dent. Res., 92(12): 1065-1073(2013).
Kwon, Kwang-Chui et al., "Oral delivery of bioencapsulated exendin-4 expressed in chloroplasts lowers blood glucose level in mice and stimulates insulin secretion in beta-TC6 cells", Plant Biotechnol. J., 11(1): 77-86 (2013).
Kwon, Kwang-Chui et al., "Oral delivery of human biopharmaceuticals, autoantigens and vaccine antigens bioencapsulated in plant cells", Adv. Drug Deliv. Rev., 65(6): 782-799 (2013).
Lakshmi, Priya Saikumar et al., "Low Cost Tubercuslosis Vaccine Antigens in Capsules: Expression in Chloroplasts, Bio-Encapsulation, Stability and Functional Evaluation in Vitro", PLoS ONE, 8(1): e54708 (2013).
Lee, Seung-Bum etal., "Expression and characterization of antimicrobial peptides Retrocyclin-101 and Protegrin-1 in chloroplasts to control viral and bacterial infections", Plant Biotechnol., J., 9(1): 100-115 (2011).
Morassutti, Carla et al., "Producgtion of a recombinant antimicrobial peptide in transgenic plants using a modified VMA intein expression system", FEBS Letters, 519: 141-146 (2002).
Ohashi, Tomoo et al., "An experimental study of GFP-based FRET, with application to intrinsically unstructured proteins", Protein Sequence, 16: 1429-1438 (2007).
Otsuka, Ryoko et al., "Application of chimeric glucanase comprising mutanse and dextranse for prevention of dental biofilm formation", Microbiol. Immunol., 59: 28-36 (2015).
Paes, A.F. et al., "The Role of Sucrose in Cariogenic Dental Biofilm Formation—New Insight", J. Dent. Res., 85(10): 878-887 (2006).
Peterson, Brandon W. et al., "Viscoelasticity of biofilms and their recalcitrance to mechanical and chemical challenges", FEMS Microbiology Reviews, 39: 234-245 (2015).
Sassi, A.B. etal., "Formulation Development of Retrocyclin 1 Analog RC-101 as an Anti-HIV Vaginal Microbicide Product", Antimicrobial Agents and Chemotherapy, 55(5): 2282-2289 (2011).
Sassi, A.B. et al., "Preformulation and stability in biological fluids of the retrocyclin RC-101, a potential anti-HIV topical microbicide", AIDS Research and Therapy, 8: 27 (2011).
Verma, Dheeraj et al., "Chloroplast-derived enzyme cocktails hydrolyse lignocellulosic biomass and release fermentable sugars", Plant Biotechnol. J., 8(3): 332-350 (2010).
Wang, Wei et al., "Retrocyclin, an Antiretroviral O-Defensin, Is a Lectin", J. Immunol., 170: 4708-4716 (2003).
Xiao, Jin et al., "The Exopolysaccharide Matrix Modulates the Interactions between 3D Architecture and Virulence of a Mixed-Species Oral Biofilm", PLoS Pathog., 8(4): e1002623 (2012).
Xiao, Yuhong et al., "Low cost delivery of proteins bioencapsulated in plant cells to human non-immune or immune modulatory cells", Biomaterials, 80: 68-79 (2016).
Wiater, Adrian et al., "Purification and properties of an alpha-(1-3)-glucanase (EC 3.2.1.84) from Trichoderma harzianum and its use for reduction of artificial dental plaque accumulation", Acta Biochim. Pol. 60: 123-128 (2013).
Wiater, Adrian et al., "Mutanase Induction in Trichoderma harzianum by Cell Wall by Laetiporus sulphureus and its Application for Mutan Removal from Oral Biofilms", J. Microbiol. Biotechnol., 18(7): 1335-1341 (2008).
Shimotsuura, Isao et al., "Biochemical and Molecular Characterization of a Novel Type of Mutanase from *Paenibacillus* sp. Strain RM1: Identification of Its Mutan-Binding Domain, Essential for Degradation of *Streptococcus mutans* Biofilms", Applied and Environmental Microbiology, 2759-2765 (2008).
Quivey, Robert G. et al., "Raffinose-induced mutanase production from Trichoderma harzianum", FEMS Microbiology Letters, 112: 307-312 (1993).
Chen, Jie et al., "Development of Protegrins for the Treatment and Prevention of Oral Mucositis: Structure-Activity Relationships of Synthetic Protegrin Analogues", Biopolymers, 55: 88-98 (2000).
DaSilva, Bruno Rocha et al., "Antimicrobial peptide control of pathogenic microorganisms of the oral cavity: A review of the literature", Peptides, 36: 315-321 (2012).
Flemmig, Thomas F. et al., "Control of oral biofilms", Periodontology, 55: 9-15 (2000).
Hayachibara, Mitsue F. et al., "The influence of mutanase and dextranase on the production and structure of glucans synthesized by streptococcal glucosyltransferases", Carbohydrate Research, 339: 2127-2137 (2004).
Jiao, Yu-Liang et al., "Characterization of a marine-derived dextranase and its application to the prevention of dental caries", J. Ind. Microbiol. Biotechnol., 41:17-26 (2014).
Strydonck, Danielle A.C. et al., "Effect of a chlorhexidine mouthrinse on plaque, gingival inflammation and stainming in gingivitis patients: a systematic review", J. Clin. Periodontol., 39: 1042-1055 (2012).
Eckert, Randal et al., "Targeted Killing of *Streptococcus mutans* by a Pheromone-Guided "Smart" Antimicrobial Peptide", Antimicrobial Agents and Chemotherapy, 50(11): 3651-3657 (2006).
Gawande, Purushottam et al., "Antibiofilm and Antimicrobial Efficacy of DispersinB-KSL-W Peptide-Based Wound Gel Against Chronic Wound Infection Associated Bacteria", Curr. Microbiol., 68: 635-641 (2014).
Lee, Seung-Bum et al., "Expression and characterization of antimicrobial peptides Retrocyclin-101 and Protegrin-1 in chloroplasts to control viral and bacterial infections", Plant Biotechnology Journal, 9: 110-115 (2011).
Liu, Yuan et al., "Topical delivery of low-cost protein drug candidates made in chloroplasts for biofilm disruption and uptake by oral epithelial cells", Biomaterials, 105: 156-166 (2016).
Otsuka, Ryoko et al., "Application of chimeric glucanase comprising mutanase and dextranase for prevention of dental biofilm formation", Microbiology and Immunology, 59: 28-36 (2015).
Extended European Search Report and Search Opinion, dated Oct. 23, 2019, issued in corresponding European Patent Application No. 17796946.6.
International Search Report and Written Opinion, dated Oct. 19, 2017, issued in corresponding International Application No. PCT/US17/32437.

* cited by examiner

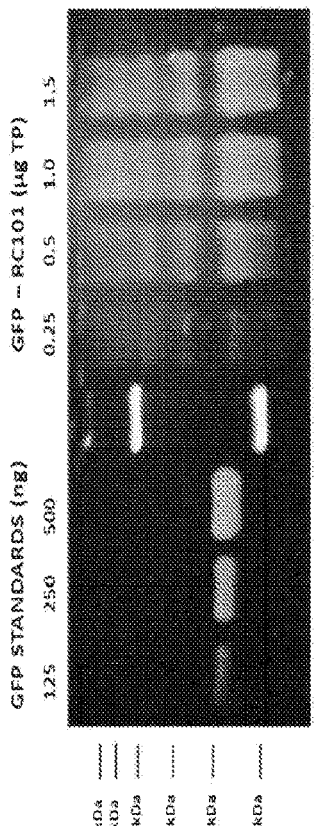
FIG. 1A
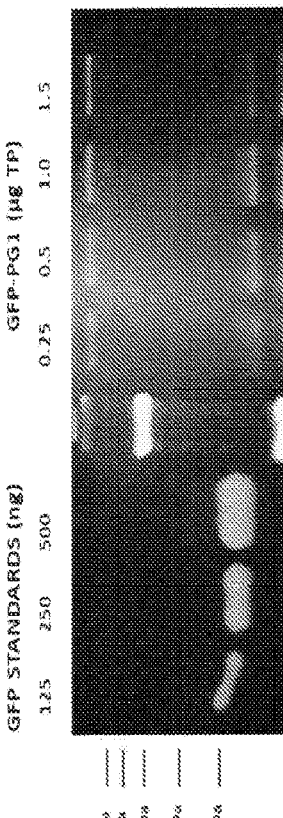
FIG. 1B
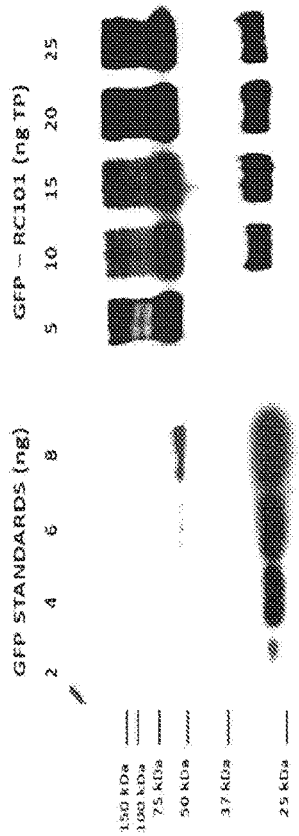
FIG. 1C
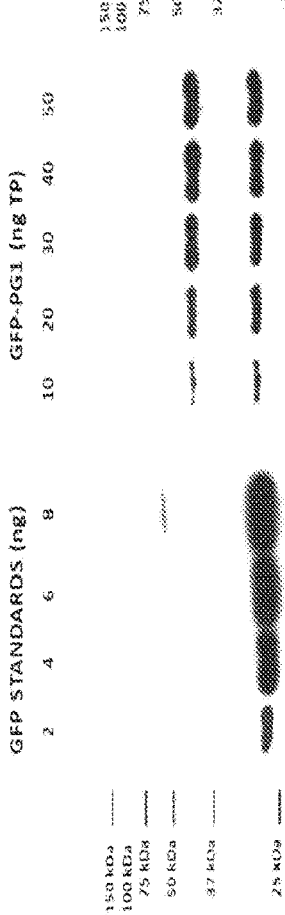
FIG. 1D
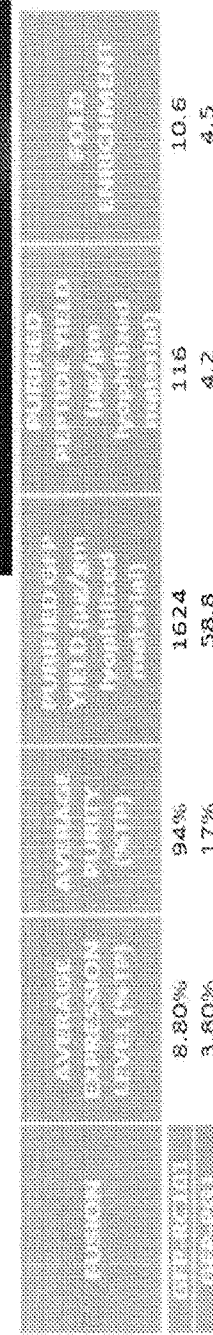

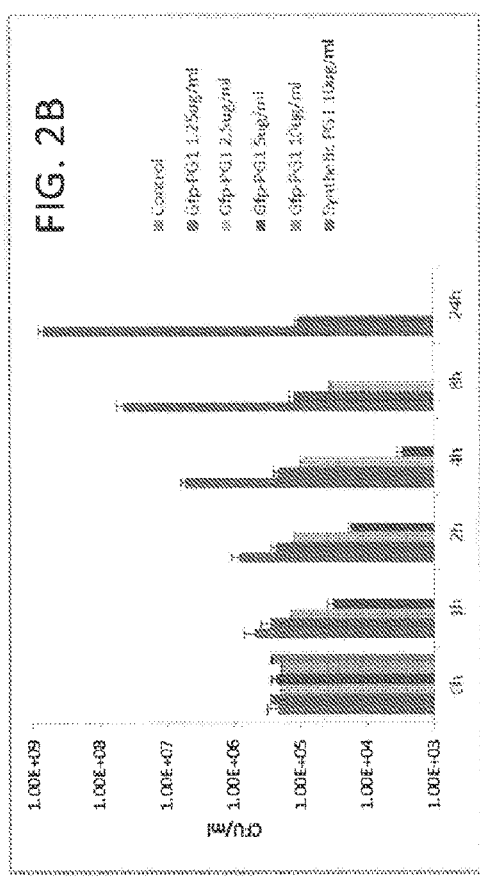
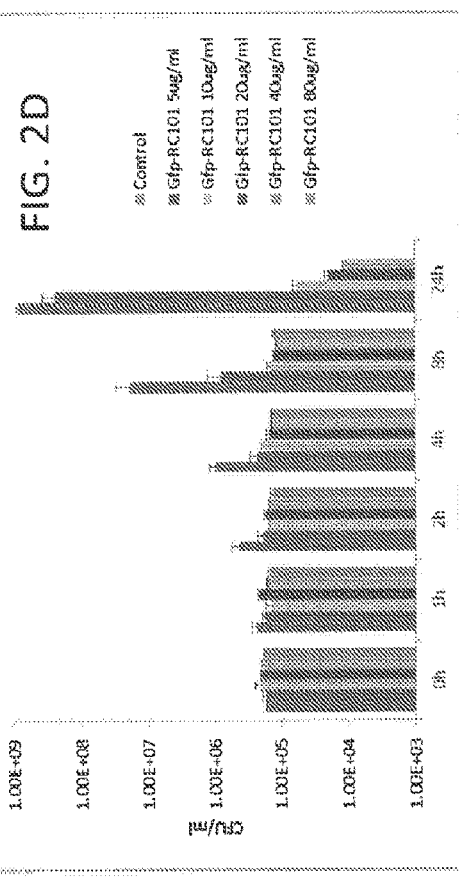
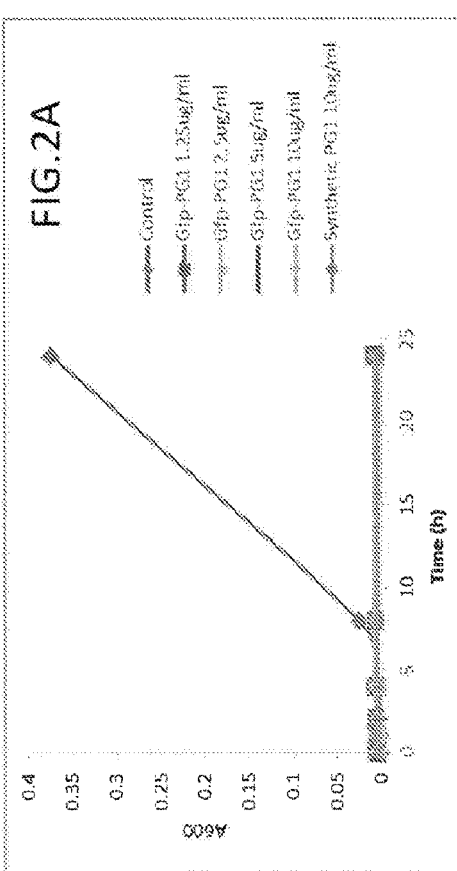
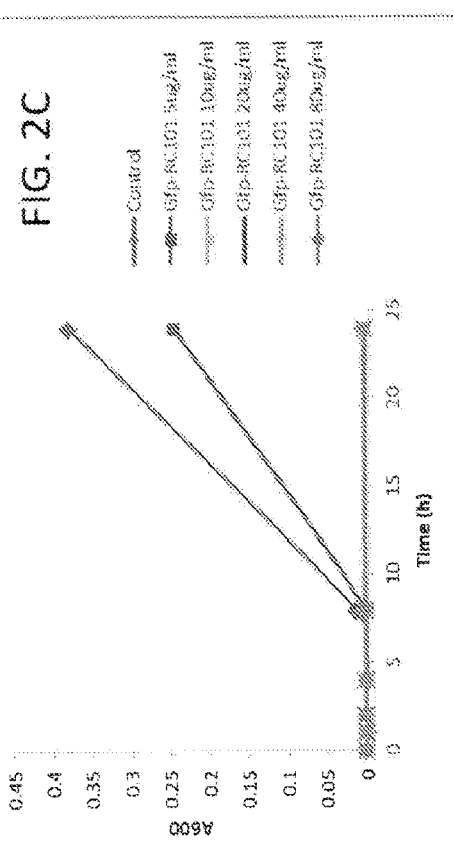

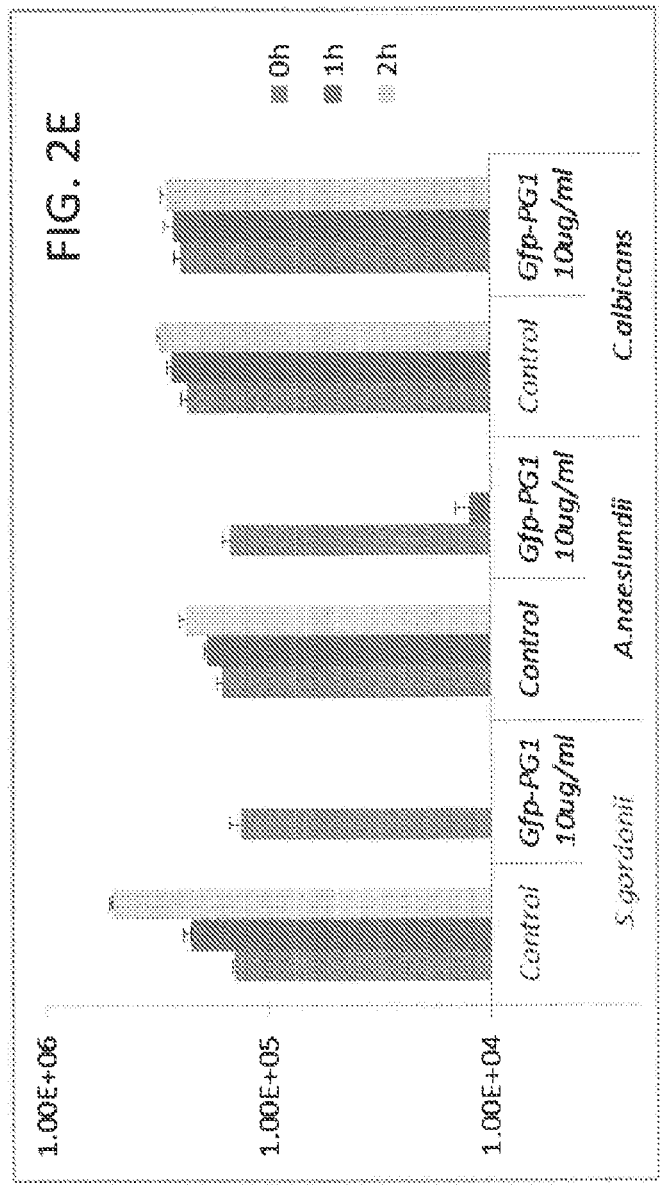

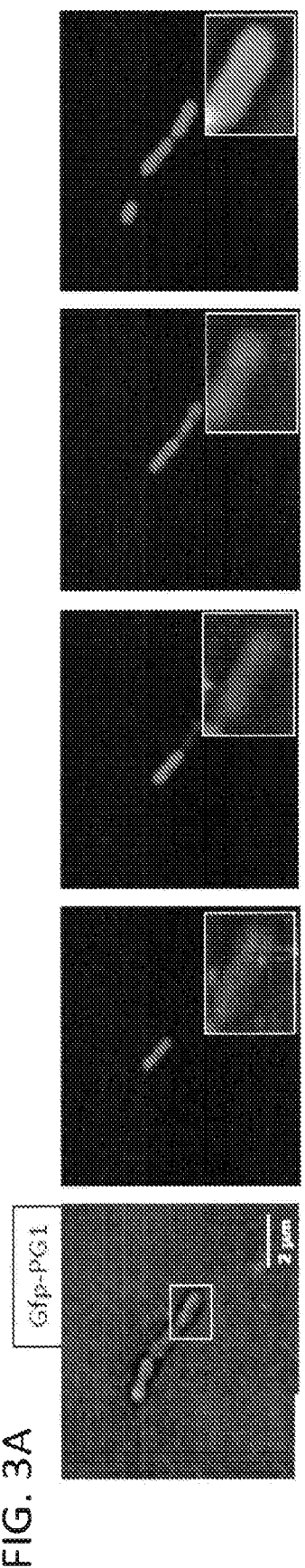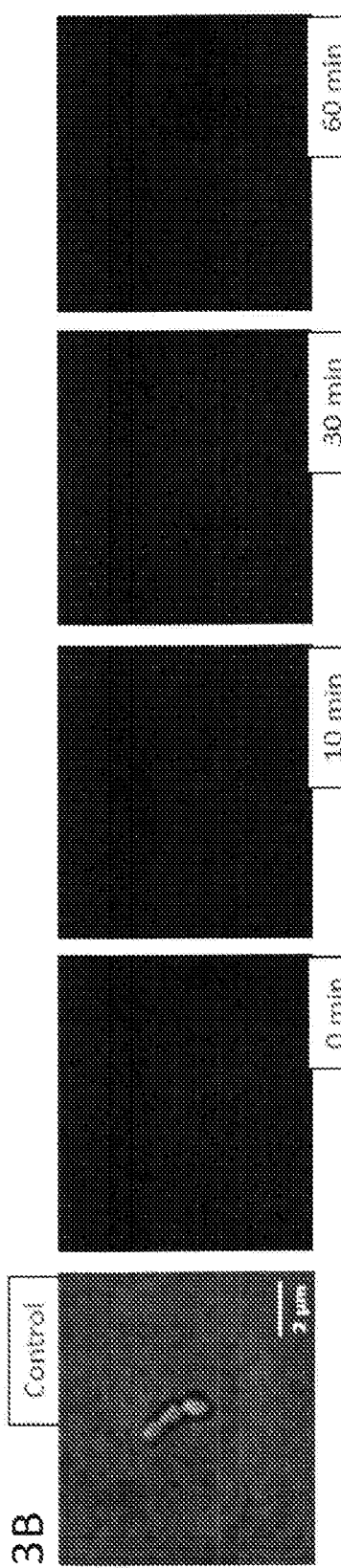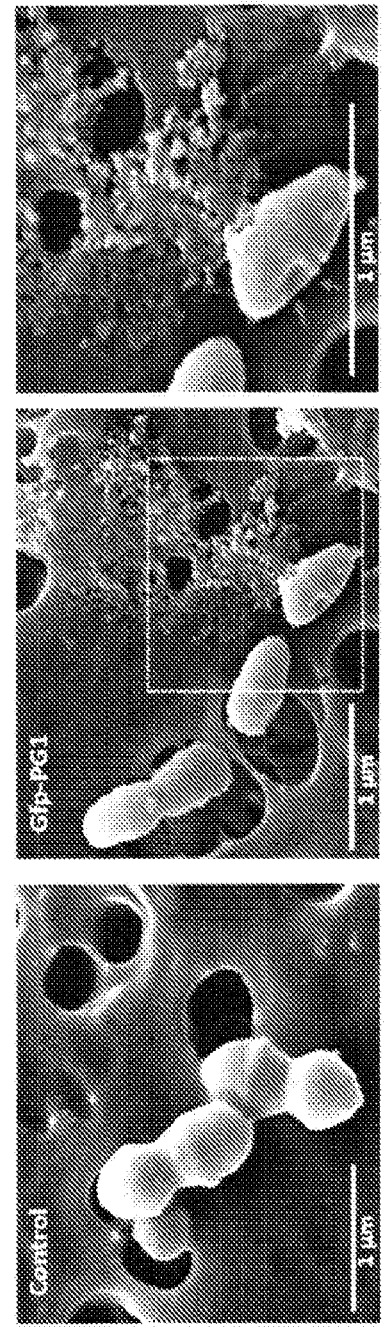
FIG. 3A
FIG. 3B
FIG. 3C

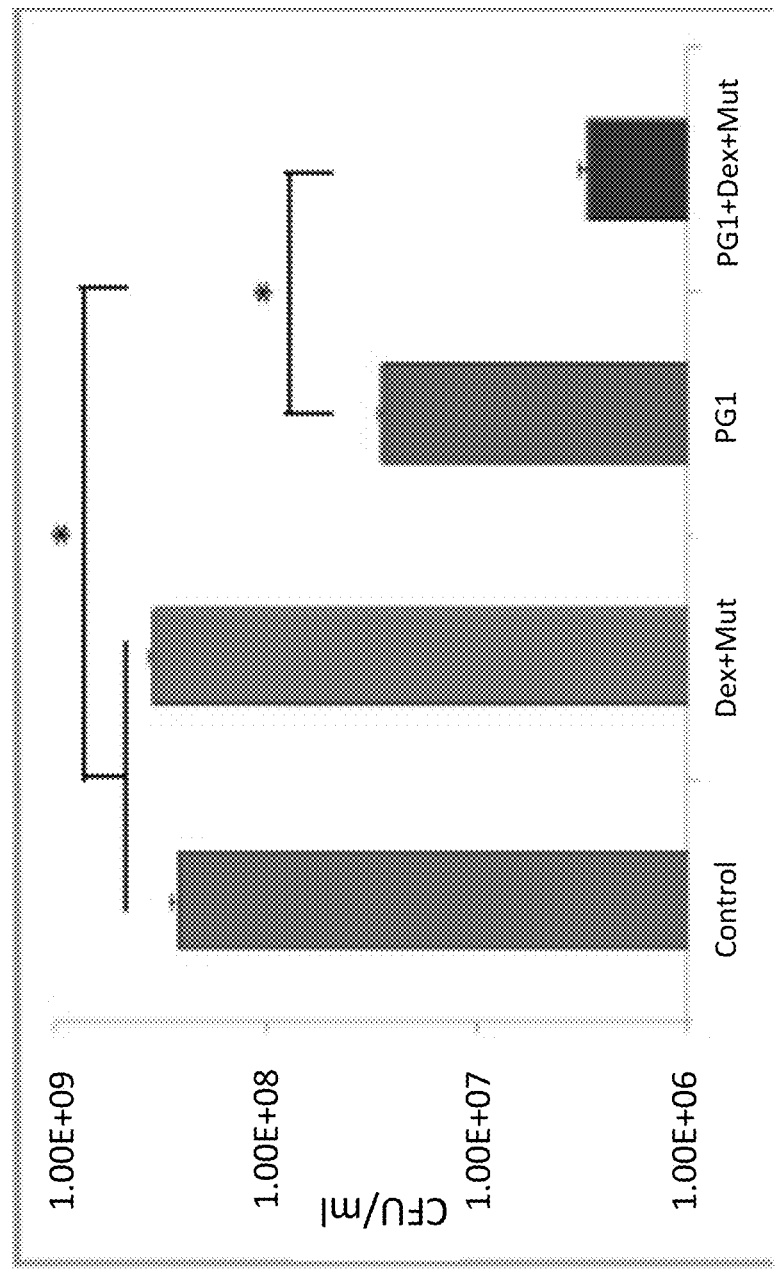

Construction of codon-optimized mutanase sequence from Paenibacillus sp. Strain RM1 into chloroplast transformation vector

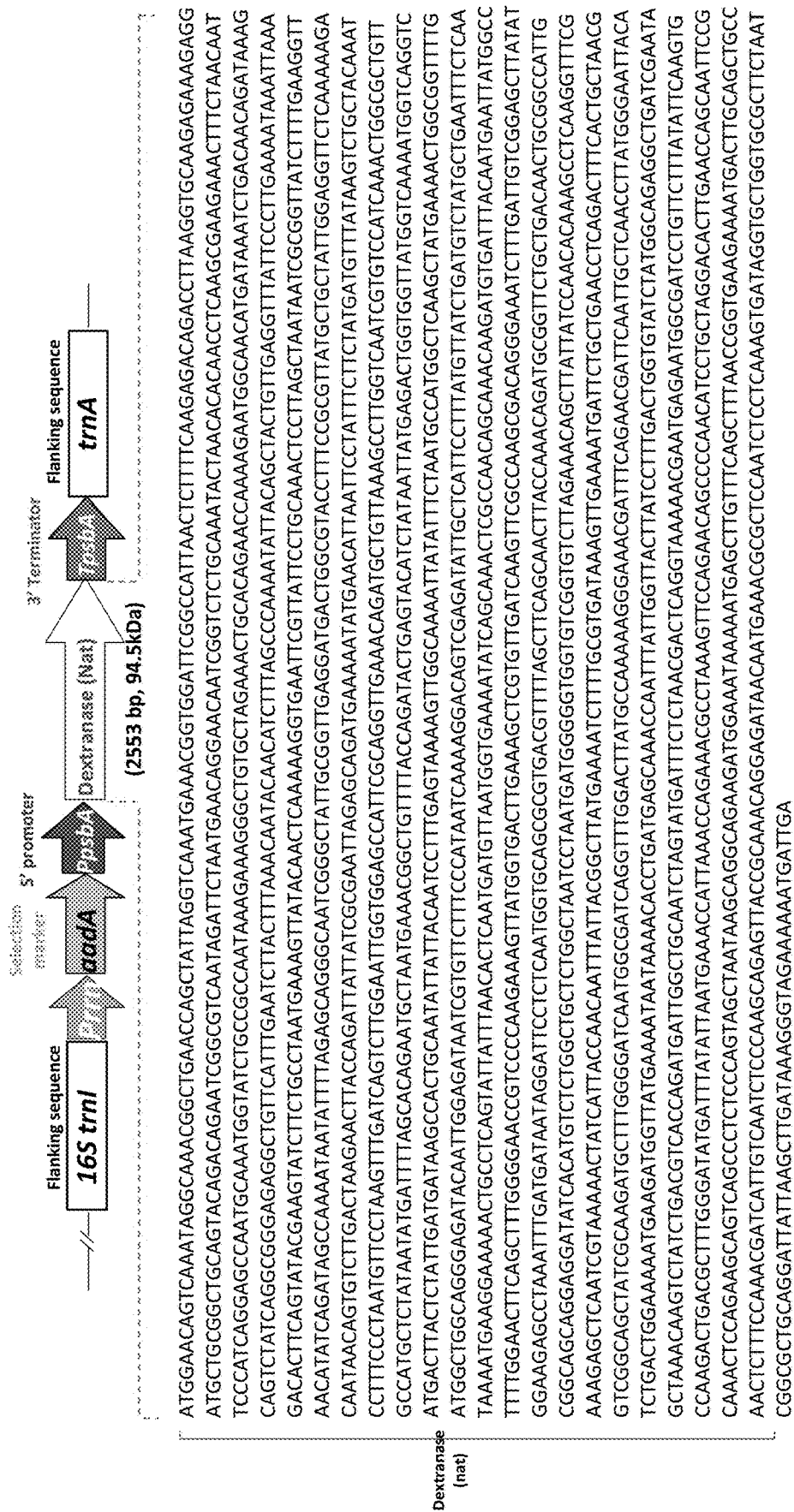
FIG. 9B. Construction of Dextranase sequence from Streptococcus mutans into chloroplast transformation vector Activity test of Dextranse expressed in E.coli

FIGURE 14
Chewing Gum tablet preparation
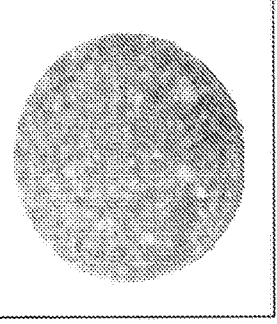
25mg Dry Plant Powder
0.45mg GFP/tablet
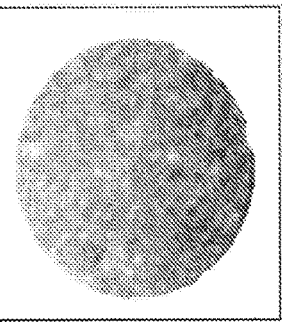
50mg Dry Plant Powder
0.9mg GFP/tablet
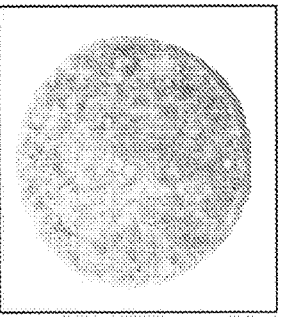
75mg Dry Plant Powder
1.35mg GFP/tablet
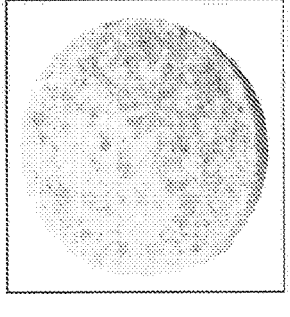
100mg Dry Plant Powder
1.8mg GFP/tablet
| Lyophilized powder | 25mg | 50mg | 75mg | 100mg |
|---|---|---|---|---|
| GFP | 0.45mg | 0.9mg | 1.35mg | 1.8mg |
| Total Weight of the tablet | ~2g | ~2g | ~2g | ~2g |
| Weight of Sample taken for analysis and GFP concentration | 250mg (56µg) | 250mg (112µg) | 250mg (168µg) | 250mg (225µg) |

FIGURE 15

Evaluation of gum tablet

Fluorescence

| Gum tablet | GFP Concentration (In 250mg) | |
|---|---|---|
| | Expected | Observed |
| 25 mg | 39 μg | 20 μg |
| 50 mg | 78.12 μg | 41.3 μg |
| 75 mg | 117.18 μg | 82.03 μg |
| 100 mg | 156.25 μg | 130 μg |

Western blot

| Gum tablet | GFP Concentration (In 250mg) | |
|---|---|---|
| | Expected | Observed |
| 25 mg | 56 μg | 11.6 μg |
| 50 mg | 112 μg | 41.3 μg |
| 75 mg | 168 μg | 66.8 μg |
| 100 mg | 225 μg | 111 μg |

COMPOSITIONS AND METHODS FOR INHIBITING BIOFILM DEPOSITION AND PRODUCTION

CROSS-REFERENCE TO RELATED APPLICATIONS

This application is as § 371 of International Application No. PCT/US17/32437, filed May 12, 2017, which claims priority to U.S. Provisional Application No. 62/335,650 filed May 12, 2016, the entire disclosure of each of the foregoing applications being incorporated herein by reference as though set forth in full.

This invention was made with government support under Grant Nos: R01 HL107904 and R01 HL109442 awarded by the National Institutes of Health. The government has certain rights in the invention.

FIELD OF THE INVENTION

The present invention relates to the fields of biofilm deposition and the treatment of disease. More specifically, the invention provides compositions and methods useful for the treatment of dental caries and other oral diseases. The invention also provides methods for coating biomedical devices for inhibiting undesirable biofilm deposition thereon.

BACKGROUND OF THE INVENTION

Several publications and patent documents are cited throughout the specification in order to describe the state of the art to which this invention pertains. Each of these citations is incorporated by reference herein as though set forth in full.

Biopharmaceuticals produced in current systems are prohibitively expensive and are not affordable for large majority of the global population. The cost of protein drugs ($140 billion in 2013) exceeds GDP of >75% of countries around the globe [Walsh 2014], making them unaffordable. One third of the global population earns <$2 per day and can't afford any protein drug (including the underprivileged, elderly and lower socio-economic groups in the US). Such high costs are associated with protein production in prohibitively expensive fermenters, purification, cold transportation/storage, short shelf life and sterile delivery methods [Daniell et al 2015, 2016].

Biofilms are formed by a complex group of microbial cells that adhere to the exopolysaccharide matrix present on the surface of medical devices. Biofilm-associated infections associated with medical device implantation pose a serious problem and adversely affects the function of the device. Medical implants used in oral and orthopedic surgery are fabricated using alloys such as stainless steel and titanium. Surface treatment of medical implants by various physical and chemical techniques has been attempted in order to improve surface properties, facilitate biointegration and inhibit bacterial adhesion as bacterial adhesion is associated with surrounding tissue damage and often results in malfunction of the implant.

Many infectious diseases in humans are caused by biofilms, including those occurring in the mouth [Hall-Stoodley et al., 2004; Marsh, et al 2011]. For example, dental caries (or tooth decay) continues to be the single most prevalent biofilm-associated oral disease, afflicting mostly underprivileged children and adults in the US and worldwide, resulting in expenditures of >$81 billion annually [Beiker and Flemmig, 2011; Dye et al., 2015; Kassebaum et al, 2015]. Caries-causing (cariogenic) biofilms develop when bacteria accumulate on tooth-surfaces, forming organized clusters of bacterial cells that are firmly adherent and enmeshed in a extracellular matrix composed of polymeric substances such as exopolysaccharides (EPS) [Bowen and Koo, 2011]. Current topical antimicrobial modalities for controlling cariogenic biofilms are limited. Chlorhexidine (CHX) is considered the 'gold standard' for oral antimicrobial therapy, but has adverse side effects including tooth staining and calculus formation, and is not recommended for daily therapeutic use [Jones, 1997; Autio-Gold, 2008]. As an alternative, several antimicrobial peptides (AMPs) have emerged with potential antibiofilm effects against caries-causing oral pathogens such as *Streptococcus mutans* [da Silva et al., 2012; Guo et al., 2015]. Antimicrobial peptides (AMP) are an evolutionarily conserved component of the innate immune response and are naturally found in different organisms, including humans. When compared with conventional antibiotics, development of resistance is less likely with AMPs. They are potently active against bacteria, fungi and viruses and can be tailored to target specific pathogens by fusion with their surface antigens (Lee et al 2011; DeGray et al 2001; Gupta et al 2015). Linear AMPs have poor stability or antimicrobial activity when compared to AMPs with complex secondary structures. For example, retrocyclin or protegrin has high antimicrobial activity or stability when cyclized (Wang et al 2003) or when it forms a hairpin structure (Chen et al 2000) via disulfide bond formation. RC101 is highly stable at pH 3, 4, 7 and temperature 25° C. to 37° C. as well as in human vaginal fluid for 48 hours (Sassi et al 2011a), while its antimicrobial activity was maintained for up to six months (Sassi et al 2011b). Likewise, protegrin is highly stable in salt or human fluids (Lai et al 2002; Ma et al 2015) but lost potency when linearized. These intriguing characteristics of antimicrobial peptides with complex secondary structures may facilitate development of novel therapeutics. However, the high cost of producing sufficient amounts of antimicrobial peptides is a major barrier for their clinical development and commercialization.

SUMMARY OF THE INVENTION

In accordance with the present invention, a multi-component composition comprising at least one antimicrobial peptide (AMP) and at least one biofilm degrading enzyme which act synergistically to degrade biofilm structures and inhibit biofilm deposition is provided. In certain embodiments, the AMP is selected from protegrin 1, RC-101 and the AMPs listed in Table 1. The biofilm degrading enzyme, includes, for example, mutanase, dextranase, glucoamylase, deoxyribonuclease I, DNAase, dispersin B, glycoside hydrolases and the enzymes provided in Table 2. In certain embodiments, the coding sequences for these enzymes are codon optimized for expression in a plant chloroplast. In a particularly preferred embodiment, the at least one AMP and at least one biofilm degrading enzyme are produced recombinantly. In a particularly preferred embodiment the AMP and biofilm degrading enzyme(s) are expressed as a fusion protein. When the composition is for the treatment of oral diseases, the composition may optionally further comprise an antibiotic, fluoride, CHX or all of the above. The composition may be contained within chewing gum, hard candy, or within an an oral rinse. Preferred fusion proteins of the invention include, without limitation, PG-1-Mut, PG-1-Dex, PG-1-Mut-Dex, RC-101-Mut, RC-101-Dex, RC-101-Mut-Dex for use alone or in combination for the degradation of biofilms. Notably any of the AMPs listed in Table 1 can replace either PG-1 or RC-101 in the aforementioned fusion proteins to alter or improve the bacteriocidal action of the fusion protein. To alter the degradation activity of the fusion proteins, the enzymes listed above and hereinbelow may replace Mut, Dex or both in the fusion proteins of the invention. In another embodiment, when two different EPS enzymes are employed in the compositions, such enzymes may be delivered at different ratios, e.g., 1:2, 1:3, 1:4, 1:5, 1:6, 1:7, 1:8 etc. When Mut and Dex are delivered together in a gum or oral rinse for example, a preferred ratio is 5:1 Dex:Mut.

In another aspect, the invention provides a method of degrading and/or removing biofilm comprising contacting a surface harboring said biofilm with the compositions described above, the composition having a bactericidal effect, and reducing or eliminating said biofilm comprising one or more undesirable microorganisms, wherein when said biofilm is present in or on an animal subject in need of said reduction or elimination. In certain embodiments, the biofilm is present in the mouth. In other embodiments, the biofilm is present on an implanted medical device. The method may also be used to remove biofilms present in an internal or external body surface iselected from the group consisting of a surface in a urinary tract, a middle ear, a prostate, vascular intima, heart valves, skin, scalp, nails, teeth and an interior of a wound.

In yet another embodiment, the composition of the invention comprising said at least one AMP and said at least one biofilm degrading enzyme are produced in a plant plastid. The plant may be a tobacco plant and the sequences encoding said AMP and enzyme is codon optimized for expression in a plant plastid. In a preferred embodiment, the AMP and biofilm degrading enzyme are expressed in a lettuce plant as a fusion protein under the control of endogenous regulatory elements present in lettuce plastids.

BRIEF DESCRIPTION OF THE DRAWINGS

FIGS. 1A-1D—Purification of GFP fused Retrocyclin (RC101) and Protegrin (PG1) expressed in tobacco chloroplasts—FIG. 1A. Western blot analysis of purified GFP-RC101 fusion using Anti-GFP antibody. FIG. 1B. Native fluorescence gel of purified GFP-RC101 fusion. FIG. 1C. Western blot of purified GFP-PG1 fusion using Anti-GFP antibody. FIG. 1D. Native fluorescence gel of purified GFP-PG1. Note—All the samples for FIG. 1A-1D were loaded based on total protein values obtained from the Bradford method. Densitometry using Image J software was done to determine GFP concentration Expression level, purity and yield. Expression level and yield were calculated from GFP concentrations relative to total protein values. Yield was determined by multiplying GFP concentration with recovered volume after purification. Individual peptide yield was determined by dividing GFP yield with molar factor 14 (ratio of GFP MW to peptide MW). The fold enrichment was calculated by dividing % purity with % expression in plant crude extracts.

FIGS. 2A-2E. Antimicrobial activity of AMPs (GFP-PG1 and GFP-RC101) against Streptococcus mutans and other oral microbes. Cell viability was determined by absorbance ($A_{600\ nm}$) and counting colony forming units (CFU) overtime. (FIG. 2A) Time-killing curve of S. mutans treated with different concentrations of GFP-PG1 and synthetic PG1 (A600 nm). (FIG. 2B) Viable cells (CFU/ml) of S. mutans treated with GFP-PG1 and synthetic PG1 at each time point. (FIG. 2C) Time-killing curve of S. mutans treated with GFP-RC101 at different concentrations ($A_{600}$ nm). (FIG. 2D) Viable cells (CFU/ml) of S. mutans treated with GFP-RC101 at each time point. (FIG. 2E) Viable cells (CFU/ml) of S. gordonii, A. naeslundii and C. albicans treated with GFP-PG1 at 10 µg/ml for 1 h and 2 h.

FIGS. 3A-3C. Bacterial killing by GFP-PG1 as determined via confocal fluorescence and SEM imaging (FIG. 3A) Time-lapse killing of S. mutans treated with GFP-PG1 at 10 µg/ml. The control group (FIG. 3B) consisted of S. mutans cells treated with buffer only. Propidium iodide (PI) (in red) was used with confocal microscopy to determine the bacterial viability over time at single-cell level. PI is cell-impermeant and only enters cells with damaged membranes; in dying and dead cells a bright red fluorescence is generated upon binding of PI to DNA. GFP-PG1 is shown in green. (FIG. 3C) Morphological observations of S. mutans subjected to GFP-PG1 at a concentration of 10 µg/ml for 1 h using scanning electron microscopy. Red arrows show dimpled membrane and extrusion of intracellular content.

(FIG. 4C) Quantitative analysis of proportion of live and dead S. mutans cells via quantitative PCR (qPCR) with or without propidium monoazide (PMA) treatment (Klein et al., 2012). The combination of PMA and qPCR (PMA-qPCR) quantify viable cells with intact membrane. Before genomic DNA isolation and qPCR quantification, PMA is added to selectively cross-link DNA of dead cells, and thereby prevent PCR amplification (Klein et al., 2012). Asterisks indicate that the values from GFP-PG1 treatment are significantly different from control ($P<0.05$).

FIGS. 6A-6C. Biofilm disruption by synthetic PG1 alone or in combination with EPS-degrading enzymes. (FIG. 6A) Time-lapse quantification of EPS degradation within intact biofilms using COMSTAT. (FIG. 6B) The viability of S. mutans biofilm treated with synthetic PG1 and EPS-degrading enzymes (Dex/Mut) either alone or in combination by ImageJ. (FIG. 6C) Antibiofilm activity of synthetic PG1 was enhanced by EPS-degrading enzymes (Dex/Mut). Asterisks indicate that the values for different experimental groups are significantly different from each other ($P<0.05$).

FIGS. 9A-9B. Vectors and codon optimized sequences for mutanase (FIG. 9A) and dextranase (FIG. 9B). Codon optimized mutanase: SEQ ID NO: 1. Codon Optimized dextranase: SEQ ID NO: 2.

FIG. 12 shows western blots showing mutanase expression in *E. coli*. FIG. 12B shows *E. coli* spread on 0.5% blue dextran plates. Transformed clones are able to produce recombinant dextranase normally made in *S. mutans* and able to clear a blue halo around the colony.

FIG. 14. Chewing gum tablet preparation is shown. While GFP is exemplified herein, chewing gum comprising the AMP-enzyme fusion proteins (e.g., those provided in FIGS. 9 and 10) is also within the scope of the invention.

FIG. 15. Gum tables were evalulated via fluorescence, and by western blot to ascertain the concentration of GFP. Quantification of the GFP release from chewing gum based on (i) Western blotting (ii) Fluorometer (Fluoroskan Ascent™ Microplate Fluorometer—Thermo; $\lambda_{ex}$ 485 nm; $\lambda_{em}$ 538 nm). Commercial GFP (Vector Laboratories, Cat# MB-0752) was used as standard. The chewing gum was ground in the protein extraction buffer.

DETAILED DESCRIPTION OF THE INVENTION

Figure 4A:
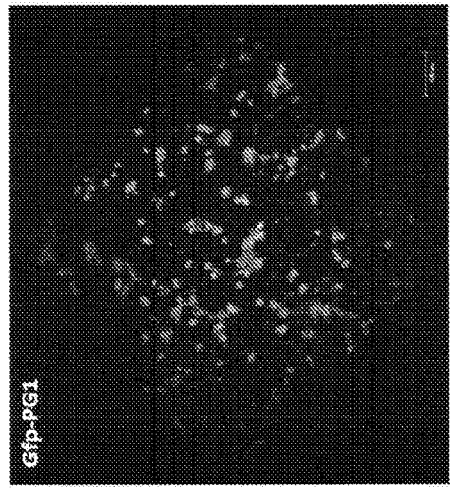
FIGS. 4A-4C Inhibition of biofilm formation by a single topical treatment of GFP-PG1. This figure displays representative images of three-dimensional (3D) rendering of S. mutans biofilm. Bacterial cells were stained with SYTO 9 (in green) and EPS were labeled with Alexa Fluor 647 (in red). Saliva-coated hydroxyapatite (sHA) disc surface was treated with a single topical treatment of GFP-PG1 with a short-term 30 min exposure (FIG. 4B). The control group (FIG. 4A) was treated with buffer only. Then, the treated sHA disc was transferred to culture medium containing 1% (w/v) sucrose and actively growing S. mutans cells ($10^5$ cfu/ml) and incubated at 37° C., 5% $CO_2$ for 19 h. After biofilm growth, the biofilms were analyzed by two photon confocal microscopy.

Many infectious diseases in humans are caused by virulent biofilms, including those occurring within the mouth (e.g. dental caries and periodontal diseases). Dental caries (or tooth decay) continues to be the single most costly and prevalent biofilm-associated oral disease in the US and worldwide. It afflicts children and adults alike, and is a major reason for emergency room visits leading to absenteeism from work and school. Unfortunately, the prevalence of dental caries is still high (>90% of US adult population) and it remains the most common chronic disease afflicting children and adults, particularly from a poor socio-economic background. Furthermore, poor oral health often leads to systemic consequences and impacts overall health. Importantly, the cost to treat the ravages of this disease (e.g. carious lesions and pulpal infection) exceeds $40 billion/yr in the US alone. Fluoride is the mainstay of dental caries prevention. However, its widespread use offers incomplete protection against the disease. Fluoride is effective in reducing demineralization and enhancing demineralization of early carious lesions, but has limited effects against biofilms. Conversely, current antimicrobial modalities for controlling caries-causing biofilms are largely ineffective.

There is an urgent need to develop efficacious therapies to control virulent oral biofilms. In accordance with the present invention, methods for low-cost production and delivery of therapeutically effective plant-expressed biopharmaceuticals superior to current antibiofilm/anti-caries modalities are provided.

Definitions:

As used herein, antimicrobial peptides are small peptides having any bacterial activity. "RC-101" is an analogue of retrocyclin, a cyclic octadecapeptide, which can protect human CD4+ cells from infection by T- and M-tropic strains of HIV-1 in vitro and prevent HIV-1 infection in human cervicovaginal tissue. The ability of RC-101 to prevent HIV-1 infection and retain full activity in the presence of vaginal fluid makes it a good candidate for other topical microbicide applications, especially in oral biofilms. The sequence of RC-101 is provided in Plant Biotechnol J. 2011 January; 9(1): 100-115 which is incorporated herein by reference.

"C16G2" is a novel synthetic antimicrobial peptide with specificity for *S. mutans*, "Protegrin-1 (PG)" is a cysteine-rich, 18-residue β-sheet peptide. It has potent antimicrobial activity against a broad range of microorganisms, including bacteria, fungus, virus, and especially some clinically relevant, antibiotic-resistant bacteria. For example, bacterial pathogens *E. coli* and fungal opportunist *C. albicans* are effectively killed by PG in laboratory testing. The sequence of PG-1 is provided in Plant Biotechnol J. 2011 January; 9(1): 100-115 which is incorporated herein by reference.

Additional antimicrobial peptides include those set forth below in Table 1 below.

TABLE 1

Peptide sequences (single-letter amino acid code) of CSP, $CSP_{C16}$-containing STAMPs, and STAMP components

| Peptide | Amino acid sequence[a] | Molecular wt (observed) |
|---|---|---|
| CSP | SGSLSTFFRLFNRSFTQALGK (SEQ ID NO: 28) | 2,364.9 |
| $CSP_{C16}$ | TFFRLFNRSFTQALGK (SEQ ID NO: 3) | 1,933.3 |
| G2 | KNLRIIRKGIHIIKKY[b] (SEQ ID NO: 4) | 1,993.5 |
| C16G2 | TFFRLFNRSFTQALGKGGGKNLRIIRKGIHIIKKY[b] (SEQ ID NO: 5) | 4,079.0 |
| $CSP_{M8}$ | TFFRLFNR (SEQ ID NO: 6) | 1,100.6 |
| M8G2 | TFFRLFNRGGGKNLRIIRKGIHIIKKY[b] (SEQ ID NO: 7) | 3,246.9 |
| S6L3-33 | FKKFWKWFRRF (SEQ ID NO: 8) | 1,677.5 |
| C16-33 | TRRRLFNRSFTQALGKSGGGFKKFWKWFRRF (SEQ ID NO: 9) | 3,849.0 |
| M8-33 | TFFRLFNRSGGGFKKFWKWFRRF (SEQ ID NO: 10) | 3,016.9 |

[a] Linker regions between targeting and killing peptides are underlined.
[b] Peptide C-terminal amidation.

A "biofilm" is a complex structure adhering to surfaces that are regularly in contact with water, consisting of colonies of bacteria and usually other microorganisms such as yeasts, fungi, and protozoa that secrete a mucilaginous protective coating in which they are encased. Biofilms can form on solid or liquid surfaces as well as on soft tissue in living organisms, and are typically resistant to conventional methods of disinfection. Dental plaque, the slimy coating that fouls pipes and tanks, and algal mats on bodies of water are examples of biofilms. Biofilms are generally pathogenic in the body, causing such diseases as dental caries, cystic fibrosis and otitis media.

"Biofilm degrading enzymes" include, without limitation, exo-polysaccharide degrading enzymes such as dextranase, mutanase, DNAse, endonuclease, deoxyribonuclease I, dispersin B, and glycoside hydrolases, such as 1→3)-α-D-glucan hydrolase, although use of chloroplast codon optimized sequences encoding dextranase and mutanase are preferred, the skilled person is well aware of many different biofilm degrading enzymes in the art. Additional enzyme sequences for use in the fusion proteins of the invention are provided below.

As used herein, the terms "administering" or "administration" of an agent, drug, or peptide to a subject includes any route of introducing or delivering to a subject a compound to perform its intended function. The administering or administration can be carried out by any suitable route, including orally, topically, intranasally, parenterally (intravenously, intramuscularly, intraperitoneally, or subcutaneously), or rectally. Administering or administration includes self-administration and the administration by another.

As used herein, the terms "disease," "disorder," or "complication" refers to any deviation from a normal state in a subject.

As used herein, by the term "effective amount" "amount effective," or the like, it is meant an amount effective at dosages and for periods of time necessary to achieve the desired result.

As used herein, the term "inhibiting" or "preventing" means causing the clinical symptoms of the disease state not to worsen or develop, e.g., inhibiting the onset of disease, in a subject that may be exposed to or predisposed to the disease state, but does not yet experience or display symptoms of the disease state.

As used herein, the term "expression" in the context of a gene or polynucleotide involves the transcription of the gene or polynucleotide into RNA. The term can also, but not necessarily, involves the subsequent translation of the RNA into polypeptide chains and their assembly into proteins.

A plant remnant may include one or more molecules (such as, but not limited to, proteins and fragments thereof, minerals, nucleotides and fragments thereof, plant structural components, etc.) derived from the plant in which the protein of interest was expressed. Accordingly, a composition pertaining to whole plant material (e.g., whole or portions of plant leafs, stems, fruit, etc.) or crude plant extract would certainly contain a high concentration of plant remnants, as well as a composition comprising purified protein of interest that has one or more detectable plant remnants. In a specific embodiment, the plant remnant is rubisco.

In another embodiment, the invention pertains to an administrable composition for treating or preventing biofilm formation in situ (e.g., in the mouth) and on biomedical devices useful for surgical implantation such as stents, artificial joints, and the like. In this embodiment, the devices are coated with the composition to inhibit unwanted biofilm deposition on the device. The composition comprises a therapeutically-effective amount of one or more antimicrobial peptides (AMP) and one or more enzymes having biofilm degrading activity in combination, each of said AMP and enzyme thereof having been expressed by a plant and a plant remnant and acting synergisticall to degrade said biofilm. In certain embodiments the AMP(s) and enzymes(s) are expressed from separate plastid transformation vectors. In other embodiments, the plastid transformation vectors comprising polycistronic coding sequences where both the AMP and the enzymes are expressed from a single vector.

Proteins expressed in accord with certain embodiments taught herein may be used in vivo by administration to a subject, human or animal in a variety of ways. The pharmaceutical compositions may be administered orally, topically, subcutaneously, intramuscularly or intravenously, though oral topical administration is preferred.

Oral compositions produced by embodiments of the present invention can be administrated by the consumption of the foodstuff that has been manufactured with the transgenic plant producing the plastid derived therapeutic protein. The edible part of the plant, or portion thereof, is used as a dietary component. The therapeutic compositions can be formulated in a classical manner using solid or liquid vehicles, diluents and additives appropriate to the desired mode of administration. Orally, the composition can be administered in the form of tablets, capsules, granules, powders, gums, and the like with at least one vehicle, e.g., starch, calcium carbonate, sucrose, lactose, gelatin, etc. The therapeutic protein(s) of interst may optionally be purified from a plant homogenate. The preparation may also be emulsified. The active ingredient is often mixed with excipients which are pharmaceutically acceptable and compatible with the active ingredient. Suitable excipients are, e.g., water, saline, dextrose, glycerol, ethanol or the like and combination thereof. In addition, if desired, the compositions may contain minor amounts of auxiliary substances such as wetting or emulsifying agents, pH buffering agents, or adjuvants. In a preferred embodiment the edible plant, juice, grain, leaves, tubers, stems, seeds, roots or other plant parts of the pharmaceuticalproducing transgenic plant is ingested by a human or an animal thus providing a very inexpensive means of treatment of disease.

In a specific embodiment, plant material (e.g. lettuce material) comprising chloroplasts expressing AMPs and biofilm degrading enzymes and combinations thereof, is homogenized and encapsulated. In one specific embodiment, an extract of the lettuce material is encapsulated. In an alternative embodiment, the lettuce material is powderized before encapsulation. As mentioned previously, the biofilm degrading proteins may also be purified from the plant following expression.

In alternative embodiments, the compositions may be provided with the juice of the transgenic plants for the convenience of administration. For said purpose, the plants to be transformed are preferably selected from the edible plants consisting of tomato, carrot and apple, among others, which are consumed usually in the form of juice.

According to another embodiment, the subject invention pertains to a transformed chloroplast genome that has been transformed with a vector comprising a heterologous gene that expresses a combination of peptides as disclosed herein.

Of particular present interest is a transformed chloroplast genome transformed with a vector comprising a heterologous gene that expresses one or more AMP and biofilm degrading enzyme or a combination thereof, polypeptide. In a related embodiment, the subject invention pertains to a plant comprising at least one cell transformed to express a peptide as disclosed herein.

Reference to genetic sequences herein refers to single- or double-stranded nucleic acid sequences and comprises a coding sequence or the complement of a coding sequence for polypeptide of interest. Degenerate nucleic acid sequences encoding polypeptides, as well as homologous nucleotide sequences which are at least about 50, 55, 60, 65, 60, preferably about 75, 90, 96, or 98% identical to the cDNA may be used in accordance with the teachings herein polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of nucleic acid sequences which encode biologically active polypeptides also are useful polynucleotides.

Variants and homologs of the nucleic acid sequences described above also are useful nucleic acid sequences. Typically, homologous polynucleotide sequences can be identified by hybridization of candidate polynucleotides to known polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% basepair mismatches.

Species homologs of polynucleotides referred to herein also can be identified by making suitable probes or primers and screening cDNA expression libraries. It is well known that the $T_m$ of a double-stranded DNA decreases by 1-1.5° C. with every 1% decrease in homology (Bonner et al., J. Mol. Biol. 81, 123 (1973). Nucleotide sequences which hybridize to polynucleotides of interest, or their complements following stringent hybridization and/or wash conditions also are also useful polynucleotides. Stringent wash conditions are well known and understood in the art and are disclosed, for example, in Sambrook et al., MOLECULAR CLONING: A LABORATORY MANUAL, $2^{nd}$ ed., 1989, at pages 9.50-9.51.

The following materials and methods are provided to facilitate the practice of the present invention.

Microorganisms and Growth Conditions

*Streptococcus mutans* UA159 serotype c (ATCC 700610), *Actinomyces naeslundii* ATCC 12104, *Streptococcus gordonii* DL-1 and *Candida albicans* SC5314 were used in present study. These strains were selected because *S. mutans* is a well-established virulent cariogenic bacteria [Ajdić D et al, 2002]. *S. gordonii* is a pioneer colonizer of dental biofilm, and *A. naeslundii* is also detected during the early stages of dental biofilm formation and may be associated with development of root caries [Dige I et al, 2009]. *C. albicans* is a fungal organism that colonizes human mucosal surfaces, and it is also detected in dental plaque from toddlers with early childhood caries [Hajeshengallis E et al, 2015]. All strains were stored at −80° C. in tryptic soy broth containing 20% glycerol. Blood agar plates were used for cultivating *S. mutans, S. gordonii* and *A. naeslundii*. Sabouraud agar plates were used for *C. albicans*. All these strains were grown in ultra-filtered (10 kDa molecular-weight cut-off membrane; Prep/Scale, Millipore, Mass.) buffered tryptone-yeast extract broth (UFTYE; 2.5% tryptone and 1.5% yeast extract, pH 7.0) with 1% glucose to mid-exponential phase (37° C., 5% CO2) prior to use.

Creation of Transplastomic Lines Expressing Different Tagged GFP Fusion Proteins The transplastomic plants expressing GFP fused with CTB, PTD, retrocyclin and protegrin were created as described in previous studies [Limaye et al 2006; Kwon et al 2013; Xiao et al 2016; Lee et al 2011]. Transplastomic lines expressing GFP fusion proteins were confirmed using Southern blot assay as described previously [Verma et al 2008]. Also, expression of GFP tagged proteins were confirmed by visualizing green fluorescence from the leaves of each construct under UV illumination.

Purification of Tag-Fused GFP Proteins

Purification of GFP fusions Protegrin-1 (PG1) and Retrocyclin (RC101) from transplastomic tobacco was accomplished by organic extraction followed by hydrophobic chromatography done previously (Lee et al, 2011). About 0.2-1 gm of lyophilized leaf material was taken and reconstituted in 10-20 ml of plant extraction buffer (0.2M Tris HCl pH 8.0, 0.1M NaCl, 10 mM EDTA, 0.4M sucrose, 0.2% Triton X supplemented with 2% Phenylmethylsulfonylfluoride and 1 protease inhibitor cocktail). The resuspension was incubated in ice for 1 hour with vortex homogenization every 15 min. The homogenate was then spun down at 75000 g at 4° C. for 1 hour (Beckman LE-80K optima ultracentrifuge) to obtain the clarified lysate. The lysate was subjected to pretreatment with 70% saturated ammonium sulfate and $\frac{1}{4}^{th}$ volume of 100% ethanol, followed by vigorous shaking for 2 min (Yakhnin et al, 1998). The treated solution was spun down at 2100 g for 3 min. The upper ethanol phase was collected and the process was repeated with $\frac{1}{16}^{th}$ volume of 100% ethanol. The pooled ethanol phases were further treated with $\frac{1}{3}^{rd}$ volume of 5M NaCl and $\frac{1}{4}^{th}$ volume of 1-butanol, homogenized vigorously for 2 min and spun down at 2100 g for 3 min. The lowermost phase was collected and loaded onto a 7 kDa MWCO zeba spin desalting column (Thermo scientific) and desalted as per manufacturer's recommendations.

The desalted extract was then subjected to hydrophobic interaction chromatography during the capture phase for further purification. The desalted extract was injected into a Toyopearl butyl—650S hydrophobic interaction column (Tosoh bioscience) which was run on a FPLC unit (Pharmacia LKB-FPLC system). The column was equilibriated with 2.3 column volumes of salted buffer (10 mM Tris-HCl, 10 mM EDTA and 50% saturated ammonium sulfate) to a final 20% salt saturation to facilitate binding of GFP onto the resin. This was followed by a column wash with 5.8 column volumes of salted and unsalted buffer mix and then eluted with unsalted buffer (10 mM Tris-HCl, 10 mM EDTA). The GFP fraction was identified based on the peaks observed in the chromatogram and collected. The collected fractions were subjected to a final polishing step by overnight dialysis. After dialysis the purified proteins were lyophilized (labconco lyophilizer) in order to concentrate the finished product and then stored in −20° C.

Quantification of Purified GFP Fusions

Quantification of GFP-RC101 and GFP-PG1 was done by both western blot and fluorescence based methods. The lyophilized purified proteins were resuspended in sterile 1×PBS and the total protein was determined by Bradford method. The purified protein was then quantified by SDS-PAGE method by loading denatured protein samples along with commercial GFP standards (Vector labs) onto a 12% SDS gel and then western blotting was done using 1:3000 dilution of mouse Anti-GFP antibody (Millipore) followed by probing with 1:4000 dilution of secondary HRP conjugated Goat-Anti Mouse antibody (Southern biotech).

The purified proteins were also quantified using GFP fluorescence. The protein samples were run on a 12% SDS gel under native conditions. After the run, the gel was placed under a UV lamp and then photographed. The GFP concentration in both western and native fluorescence methods was determined by densitometric analysis using Image J software with commercial GFP standards in order to obtain the standard curve. Purity was determined based on GFP quantitation with respect to total protein values determined in Bradford method.

Uptake of Purified Tag-Fused GFP Proteins by Human Periodontal Cell Lines

As previously described (Xiao, et al 2016), to determine the uptake of four tags, CTB, PTD, PG1 and RC101, in different human periodontal cell lines, including human periodontal ligament stem cells (HPDLS), maxilla mesenchymal stem cells (MMS), human head and neck squamous cell carcinoma cells (SCC-1), gingiva-derived mesenchymal stromal cells (GMSC), adult gingival keratinocytes (AGK) and osteoblast cells (OBC), briefly, each human cell line cells ($2 \times 10^4$) were cultured in 8 well chamber slides (Nunc) at 37° C. overnight, followed by incubation with purified GFP-fused tags: CTB-GFP (8.8 μg), PTD-GFP (13 μg), GFP-PG1 (1.2 μg) and GFP-RC101 (17.3 ag) in 100 al PBS supplemented 1% FBS at 37° C. for 1 hour. After fixing with 2% paraformaldehyde at RT for 10 min and washing with PBS for three times, all cells were stained with antifade mounting medium with DAPI (Vector laboratories, Inc). For negative control, cells were incubated with commercial GFP (2 μg) in PBS with 1% FBS at 37° C. for 1 hour. All fixed cells were imaged using confocal microscopy. The images were observed under 100× objective, and at least 10-15 GFP-positive cells were recorded for each cell line in three independent analysis.

Evaluation of Antibacterial Activity

The killing kinetics of AMPs (Gfp-PG1 and Gfp-RC101) against S. mutans were analyzed by time-lapse killing assay. S. mutans were grown to log phase and diluted to $10^5$ CFU/ml in growth medium. GFP-PG1 and GFP-RC101 were added to S. mutans suspensions at concentrations of 0 to 10 μg/ml and 0 to 80 μg/ml, respectively. At 0, 1, 2, 4, 8 and 24 h, samples were taken and serially diluted in 0.89% NaCl, then spread on agar plates and colonies were counted after 48 h. Absorbance at 600 nm was also checked at each time point. S. gordonii, A. naeslundii and C. albicans suspensions were mixed with Gfp-PG1 at concentration of 10 μg/ml, and at 0, 1 and 2 h, aliquots were taken out for enumeration of CFU.

The effects of AMP on the viability of S. mutans cells were also assessed by time-lapsed measurements. S. mutans were grown to log phase and harvested by centrifugation (5500 g, 10 min) and the pellet was washed once with sodium phosphate-buffered saline (PBS) (pH 7.2), re-suspended in PBS and adjusted to a final concentration of $1 \times 10^5$ CFU/ml. GFP-PG1 was added to S. mutans suspensions at concentrations of 10 μg/ml and 2.5 μM propidium iodide-PI (Molecular Probe Inc., Eugene, Oreg., USA) was added for labeling dead cells. 5 μl of mixtures were loaded on an agarose pad for confocal imaging. Confocal images were acquired using Leica SP5-FLIM inverted single photon laser scanning microscope with a 100×. (numerical aperture, 1.4) Oil immersion objective. The excitation wavelengths were 488 nm and 543 nm for GFP and PI, respectively. The emission filter for GFP was a 495/540 OlyMPFC1 filter, while PI was a 598/628 OlyMPFC2 filter. For the time-lapse series, images in the same field of view were taken at 0, 10, 30, and 60 min and created by ImageJ 1.44 on the world wide web at (//rsbweb.nih.gov/ij/download.html). Morphological observations of S. mutans treated with AMP were also examined by scanning electron microcopy (SEM). S. mutans were grown to log phase and diluted to $10^5$ CFU/ml in PBS. Bacteria suspension was mixed with GFP-PG1 (final concentration of 10 μg/ml) for 1 h at 37° C. After treatment, the bacteria were collected by filtration using 0.4 µm Millipore filters. The deposits were fixed in 2.5% glutaraldehyde and 2.0% paraformaldehyde in 0.1 M cacodylate buffer (pH 7.4) for 1 hour at room temperature and processed for SEM (Quanta FEG 250, FEI, Hillsboro, Oreg.) observation. Untreated or bacteria treated with buffer only served as controls.

Evaluation of Anti-Biofilm Activity

A well-characterized EPS-matrix producing oral pathogen, S. mutans UA159, was used to form biofilms on saliva-coated hydroxyapatite disc surfaces. Briefly, hydroxyapatite discs (1.25 cm in diameter, surface area of 2.7±0.2 cm2, Clarkson, Chromatography Products, Inc., South Williamsport, Pa.) were coated with filter-sterilized, clarified human whole saliva (sHA) [Xiao J et alo, 2012]. S. mutans was grown in UFTYE medium with 1% (w/v) glucose to mid-exponential phase (37° C., 5% $CO_2$). Each sHA disc was inoculated with $10^5$ CFU of actively growing S. mutans cells per ml in UFTYE medium containing 1% (w/v) sucrose, and inoculated at 37° C. and 5% $CO_2$ for 19 h. Before inoculum, the sHA discs were topically treated with GFP-PG1 solution (10 ug) for 30 min. The inhibition effect of GFP-PG1 treatment on 3D biofilm architectures were observed via confocal imaging. Briefly, EPS was labeled using 2.5 µM Alexa Fluor 647-labeled dextran conjugate (10 kDa; 647/668 nm; Molecular Probes Inc.), while the bacteria cells were stained with 2.5 µM SYTO9 (485/498 nm; Molecular Probes Inc.). The imaging was performed using Leica SP5 microscope with 20× (numerical aperture, 1.00) water immersion objective. The excitation wavelength was 780 nm, and the emission wavelength filter for SYTO 9 was a 495/540 OlyMPFEC1 filter, while the filter for Alexa Fluor 647 was a HQ655/40M-2P filter. The confocal image series were generated by optical sectioning at each selected positions and the step size of z-series scanning was 2 µm. Amira 5.4.1 software (Visage Imaging, San Diego, Calif., USA) was used to create 3D renderings of biofilm architecture [Xiao J et al. 2012, Koo H et al. 2010].

To examine the effects of the PG1 on biofilms formed with S. mutans for 19 h on sHA discs, we examined the 3D architecture of the EPS-matrix and in situ cell viability using time-lapse confocal microscopy following biofilms incubation with 1) Control, 2) EPS-degrading enzymes only, 3) PG1 only, or 4) PG1 and EPS-degrading enzymes for up to 60 minutes. The EPS-degrading enzymes used here were dextranase and mutanase, which were capable of digesting the EPS derived from S. mutans by hydrolyzing α-1,6 glucosidic linkages and α-1,3 glucosidic linkages [Hayacibara et al. 2004]. Dextranase produced from Penicillium sp. was commercially purchased from Sigma (St. Louis, Mo.) and mutanase produced from Trichoderma harzianum was kindly provided by Dr. William H. Bowen (Center for Oral Biology, University of Rochester Medical Center). Dextranase and mutanase were mixed at ratio of 5:1 before applying to biofilms [Mitsue F. Hayacibara et al. 2004]. Alexa Fluor 647-labeled dextran conjugate was used to label the EPS-matrix, while SYTO 9 and PI were used to label live cells and dead cells. Biofilms were examined using confocal fluorescence imaging at 0, 10 30 and 60 min, and subjected to AMIRA/COMSTAT/ImageJ analysis. The total biomass of EPS matrix, live and dead cells in each series of confocal images was quantified using COMSTAT and ImageJ. The ratio of live to the total bacteria at each time point was calculated, and the survival rate of live cells (relative to live cells at 0 min) was plotted. The initial number of viable cells at time point 0 min was considered to be 100%. The percent-survival rate was determined by comparing to time point 0 min.

Microbiological Assays

At selected time point (19 h), biofilms were removed, homogenized via sonication and subject to microbiological analyses as detailed previously [Xiao J et al. 2012, Koo H et al. 2010]; our sonication procedure does not kill bacteria cells while providing optimum dispersal and maximum recoverable counts. Aliquots of biofilm suspensions were serially diluted and plated on blood agar plates using an antomated Eddy Jet Spiral Plater (IUL, SA, Barcelona, Spain). Meanwhile, propidium monoazide (PMA) combined with quantitative PCR (PMA-qPCR) was used for analysis of S. mutans cell viability as describe Klein M I et al. [Klein M I et al. 2012]. The combination of PMA and qPCR will quantify only the cells with intact membrane (i.e. viable cells) because the PMA cross-linked to DNA of dead cells and extracellular DNA modifies the DNA and inhibits the PCR amplification of the extracted DNA. Briefly, biofilm pellets were resuspended with 500 µl TE (50 mM Tris, 10 mM EDTA, pH 8.0). Using a pipette, the biofilm suspensions were transferred to 1.5 ml microcentrifuge tubes; then mixed with PMA. 1.5 µl PMA (20 mM in 20% dimethyl sulfoxide; Biotium, Hayward, Calif.) was added to the biofilm suspensions. The tubes were incubated in the dark for 5 min, at room temperature, with occasional mixing. Next, the samples were exposed to light for 3 min (600-W halogen light source). After photo-induced cross-linking, the biofilm suspensions were centrifuged (13,000 g/10 min/4° C.) and the supernatant was discarded. The pellet was resuspended with 100 µl TE, following by incubation with 10.9 µl lysozyme (100 mg/ml stock) and 5 µl mutanylysin (5U/µl stock) (37° C./30 min). Genomic DNA was then isolated using the MasterPure DNA purification kit (Epicenter Technologies, Madison, Wis.). Ten pictograms of genomic DNA per sample and negative controls (without DNA) were amplified by MyiQ real-time PCR detection system with iQ SYBR Green supermix (Bio-Rad Laboratories Inc., CA) and S. mutans specific primer (16S rRNA) [Klein M I et al 2010].

Statistical Analysis

Data are presented as the mean±standard deviation (SD). All the assays were performed in duplicate in at least two distinct experiments. Pair-wise comparisons were made between test and control using Student's t-test. The chosen level of significance for all statistical tests in present study was P<0.05.

The following examples are provided to illustrate certain embodiments of the invention. They are not intended to limit the invention in any way.

Example I

Creation and Characterization of Transplastomic Lines

All fusion tags (CTB, PTD, protegrin, retrocyclin) were fused to the green fluorescent protein (smGFP) at N-terminus to evaluate their efficiency and specificity. Fusion constructs encoding these fusion proteins were cloned into chloroplast transformation vectors which were then used to transform plants of interest as described in U.S. patent application Ser. No. 13/101,389 which is incorporated herein by reference. To create plants expressing GFP fusion proteins, tobacco chloroplasts were transformed using biolistic particle delivery system. As seen in the FIG. 1B, each tag-fused GFP is driven by identical regulatory sequences—the psbA promoter and 5' UTR regulated by light and the transcribed mRNA is stabilized by 3' psbA UTR. The psbA gene is the most highly expressed chloroplast gene and therefore psbA regulatory sequences are used for transgene expression in our lab [7, 34]. To facilitate the integration of the expression cassette into chloroplast genome, two flanking sequences, isoleucyl-tRNA synthetase (trnI) and alanyl-tRNA synthetase (trnA) genes, flank the expression cassette, which are identical to the native chloroplast genome sequence. The emerging shoots from selection medium were investigated for specific integration of the transgene cassette at the trnI and trnA spacer region and then transformation of all chloroplast genomes in each plant cell (absence of untransformed wild type chloroplast genomes) was confirmed by Southern blot analysis. Thus, stable integration of all GFP expression cassettes and homoplasmy of chloroplast genome with transgenes were confirmed before extracting fusion proteins. In addition, by visualizing the green fluorescence under UV light, GFP expression of was phenotypically confirmed. Confirmed homoplasmic lines were then transferred and cultivated in an automated greenhouse to increase biomass.

To scale up the biomass of each GFP tagged plant leaf material, each homoplasmic line was grown in a temperature- and humidity-controlled greenhouse. Fully grown mature leaves were harvested in late evenings to maximize the accumulation of GFP fusion proteins driven by light-regulated regulatory sequences. To further increase the content of the fusion proteins on a weight basis, frozen leaves were freeze-dried at −40° C. under vacuum. In addition to the concentration effect of proteins, lyophilization increased shelf life of therapeutic proteins expressed in plants more than one year at room temperature [Daniell et al 2015; 2016]. Therefore, in this study, lyophilized and powdered plant cells expressing GFP-fused tag proteins were used for oral delivery to mice.

Expression and Purification of GFP Fused Antimicrobial Peptides from Transplastomic Tobacco.

Tobacco leaves expressing GFP fused antimicrobial peptides RC101 and PG1 were harvested from greenhouse and subsequently lyophilized for protein extraction and purification. The average expression level of GFP-RC101 was found to be 8.8% of total protein in crude extracts while expression of GFP-PG1 was that of 3.8% of total protein based on densitometry. The difference in expression levels was similar to what was reported previously (Lee et al 2011, Gupta et al, 2015).

Figure 8:
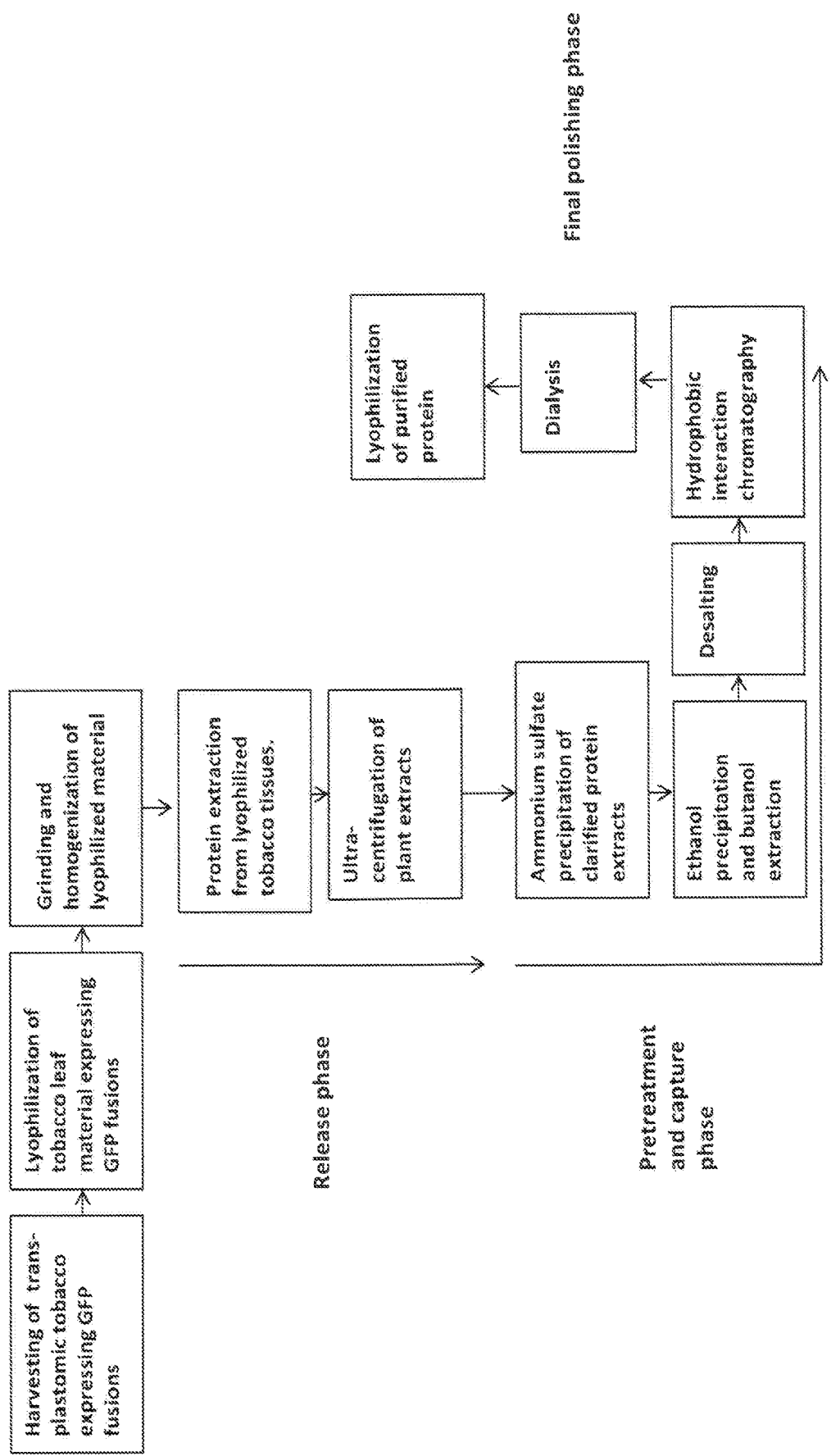
FIG. 8. Downstream processing of GFP fusions from transplastomic tobacco: Flow diagram illustrating the different steps involved in generation of purifed GFP fusions from transplastomic tobacco plants grown in greenhouse.

Purification of GFP fused to different antimicrobial peptides (RC101 and PG1) was done in order to test the microbicidal activity against both planktonic and biofilm forming S. mutans. Lyophilized tobacco material expressing different GFP fusions was used for extractions and subsequent downstream processing (See FIG. 8) to obtain the finished purified product which was subsequently quantified to determine concentration of GFP fused peptides. Quantitation of purified GFP-RC101 and GFP-PG1 was done by both western blot and Native GFP fluorescence method where purified GFP-RC101 show 94% average purity with an average yield of 1624 μg of GFP (116 μg of RC101 peptide) per gm of lyophilized leaf material (FIGS. 1A and 1B). In GFP-PG1 both methods (FIGS. 1C and 1D) show 17% average purity with an average yield of 58.8 μg of GFP (4.2 μg PG1 peptide) per gm of lyophilized leaf material. The difference in purity can be attributed to difference in the type of tags fused to GFP as seen in previous studies (Xiao et al 2015, Skosyrev et al 2003). The fold enrichment of purified GFP-RC101 and GFP-PG1 from plant extracts was 10.6 and 4.5 respectively. The western blots also show GFP standards at 27 kDa which corresponds to the monomer fragment along with a 54 kDa GFP dimer with loadings ranging from 6-8 ng of GFP. In GFP-RC101 western blots, 29 kDa and 58 kDa fragments are clearly visible which correspond to the monomer and dimer forms of the fusion (FIG. 1A). This could be attributed to the ability of GFP to form dimers (Ohashi et al, 2007). Western blots of GFP-PG1 (FIG. 1D) clearly show the 29 kDa monomer along with a 40 kDa fragment could be due to mobility shift caused by GFP-PG1 bound to other non-specific plant proteins which could have been co-purified as described previously (Morassuttia et al 2002). Native fluorescence of GFP-RC101 and GFP-PG1 (FIGS. 1B and 1D) show multimeric bands with some of them visible below the 27 kDa GFP standard size which could be because of GFP being fused to cationic peptides causing a electrophoretic mobility shift with each GFP fragment as described in previous studies (Lee et al, 2011).

Antibacterial Activity of AMPs

We first examined the antimicrobial activity of GFP-PG1 using dose-response time-kill studies as shown in FIG. 2 (A-E). GFP-PG1 displays potent antibacterial activity against *Streptococcus mutans*, a proven biofilm-forming and caries-causing pathogen, rapidly killing the bacterial cells within 1 h at low concentrations (FIG. 2A). GFP-PG1 also killed the early oral colonizers *Streptococcus gordonii* and *Actinomyces naeslundii*, but showed limited antifungal activity against *Candida albicans* at the concentrations tested (FIG. 2E). Time-lapse confocal imaging shows that *S. mutans* viability is affected as early as 10 minutes as shown in FIG. 3A relative to the untreated controls (FIG. 3B). SEM imaging revealed disruption of *S. mutans* membrane surface, causing extrusion of the intracellular content as well as irregular cell morphology, while untreated bacteria showed intact and smooth surfaces without any visible cell lysis or debris (FIG. 3C). Having shown the antimicrobial efficacy of GFP-PG1 against *S. mutans*, we have examined the potential of this antimicrobial peptide to prevent biofilm formation or disrupt pre-formed biofilms.

Inhibition of Biofilm Initiation by AMPs

Figure 4B:
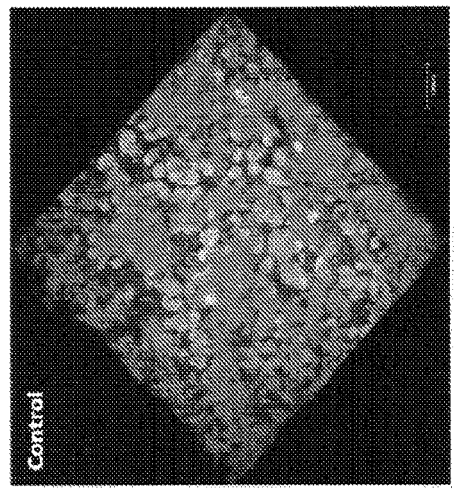
Figure 4C:
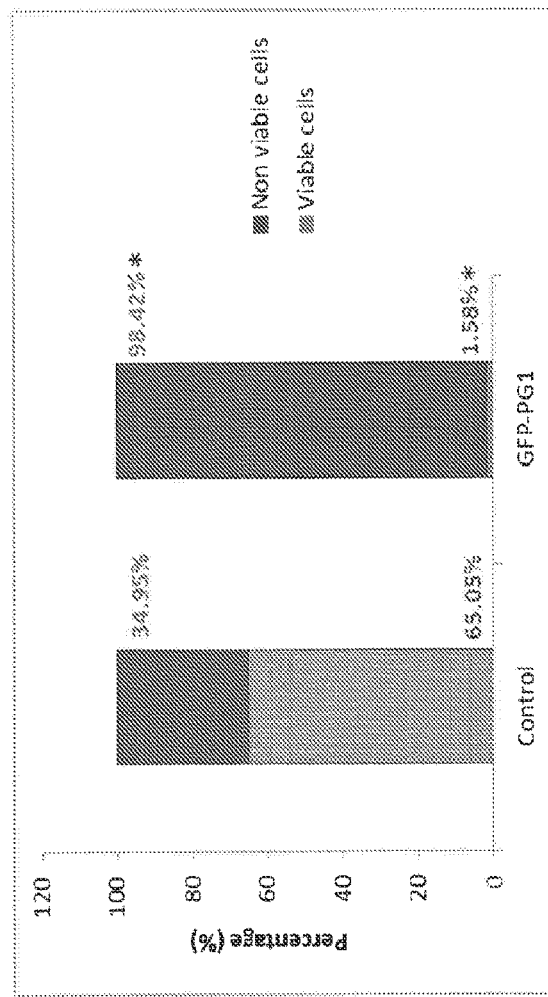

Preventing the formation of pathogenic oral biofilms is challenging because drugs need to exert therapeutic effects following topical applications. To determine whether GFP-PG1 can disrupt the initiation of the biofilm, we treated saliva coated apatitic (sHA) surface (tooth surrogate) with a single topical treatment of GFP-PG1 for 30 min, and then incubated with actively growing *S. mutans* cells in cariogenic (sucrose-rich) conditions. We observed substantial impairment of biofilm formation by *S. mutans* with minimal accumulation of EPS-matrix on the GFP-PG1 treated sHA surface (FIGS. 4B and 4C). The few adherent cell clusters were mostly non-viable compared to control (FIG. 4A), demonstrating potent effects of GFP-PG1 on biofilm initiation despite topical, short-term exposure.

Disruption of Pre-Formed Biofilm by AMP with or without EPS-Degrading Enzymes

Figure 5:
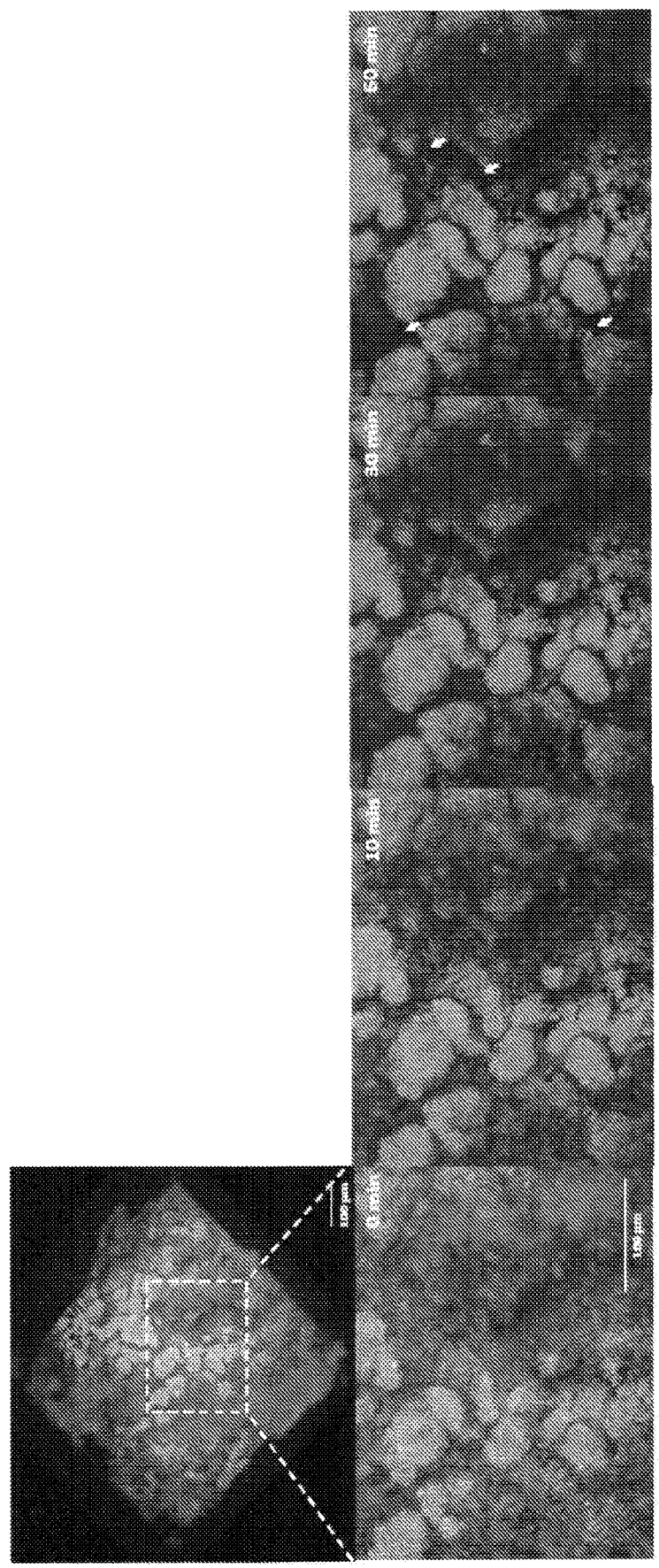
FIG. 5. EPS-degrading enzymes digesting biofilm matrix. Representative time-lapsed images of EPS degradation in S. mutans biofilm treated with combination of dextranase and mutanase. Bacterial cells were stained with SYTO 9 (in green) and EPS were labeled with Alexa Fluor 647 (in red). The white arrows show 'opening' of spaces between the bacterial cell clusters and 'uncovering' cells following enzymatic degradation of EPS.

Disruption of formed biofilms on surfaces is challenging. Disruption of cariogenic biofilms is particularly difficult because drugs often fail to reach clusters of pathogenic bacteria (such as *S. mutans*) because of the surrounding exopolysaccharides (EPS)-rich matrix that enmeshes and protects them [Bowen and Koo, 2011]. EPS-degrading enzymes such as dextranase and mutanase could help digest the matrix of cariogenic biofilms, although they are devoid of antibacterial effects. We first optimized the dextranase and/or mutanase required for EPS-matrix disruption without affecting the cell viability (data not shown). As shown in FIG. 5, the combination of dextranase and mutanase can digest the EPS (in red) and 'open spaces' (see arrows) between the bacterial cell clusters (in green) and 'uncover' cells (see arrows). Thus, the combination of GFP-PG1 and EPS-degrading enzymes synergistically potentiate the overall antibiofilm effects.

Figure 6A:
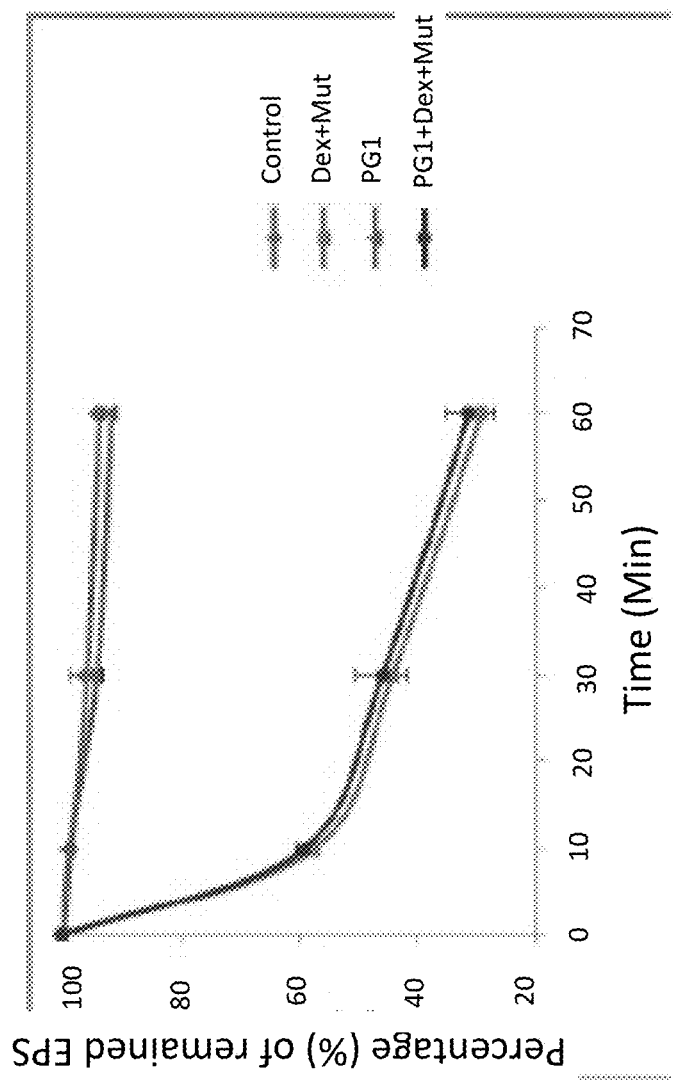
Figure 6B:
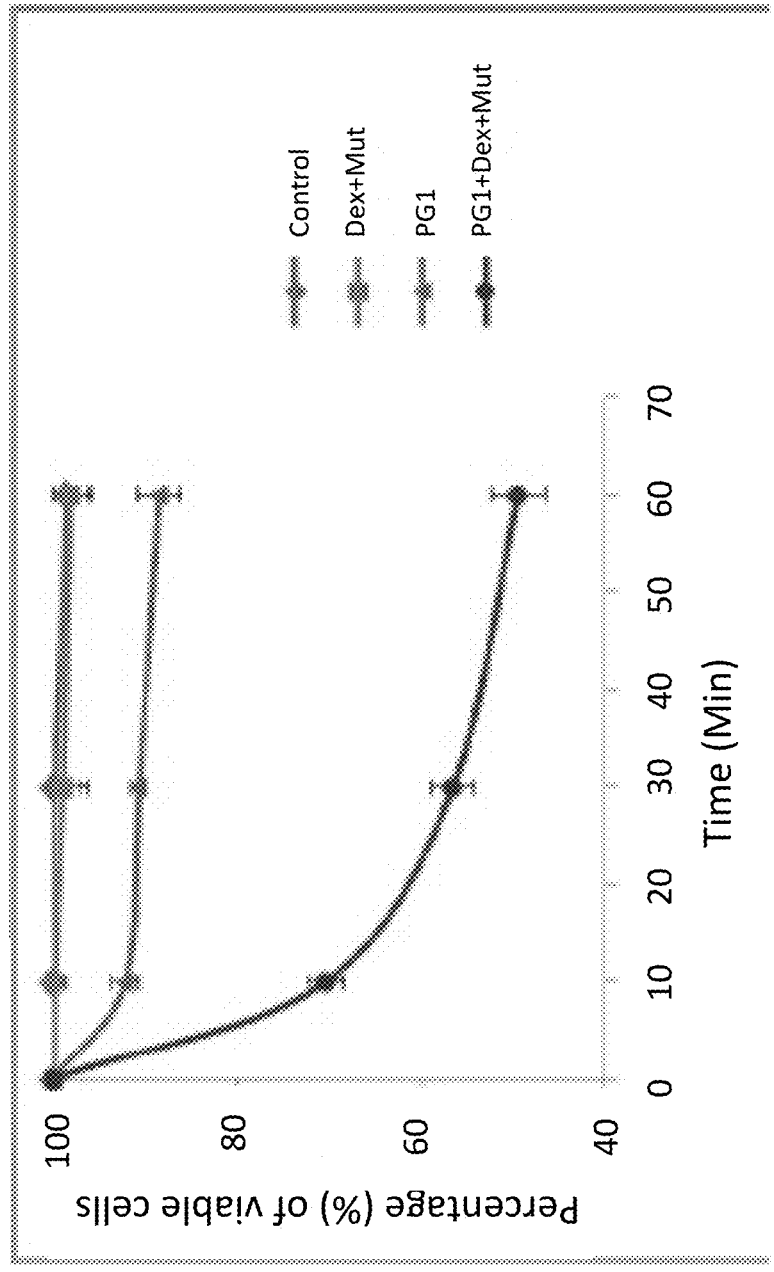
Figure 7:
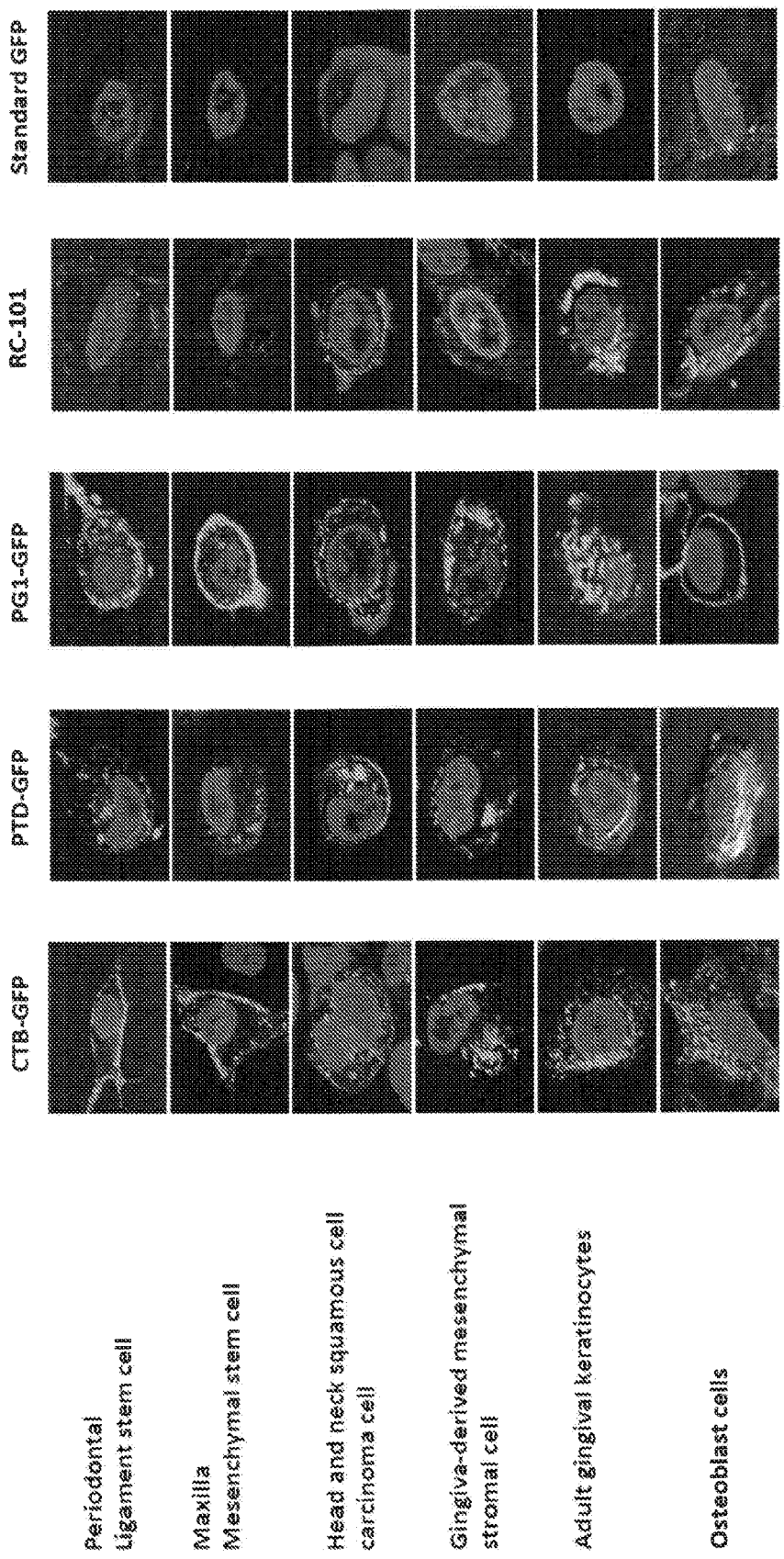
FIG. 7. In vitro uptake of purified fused protein CTB-GFP, PTD-GFP, Protegrin-1-GFP (PG1-GFP) and Retrocyclin101-GFP (RC101-GFP) in different human periodontal cell lines: human periodontal ligament stem cells (HPDLS), maxilla mesenchymal stem cells (MMS), human head and neck squamous cell carcinoma cells (SCC), gingiva-derived mesenchymal stromal cells (GMSC), adult gingival keratinocytes (AGK) and osteoblast cell (OBC) with confocal microscopy. 2×10⁴ cells of human cell lines HPDLS, MMS, SCC, GMSC, AGK and OBC were cultured in 8-well chamber slides (Nunc) at 37° C. for overnight, followed by incubation with purified GFP fusion proteins: CTB-GFP (8.8 µg), PTD-GFP (13 µg), PG1-GFP (1.2 µg), RC101-GFP (17.3 µg) in 100 µl PBS supplemented with 1% FBS, respectively, at 37° C. for 1 hour. After fixing with 2% paraformaldehyde at RT for 10 min and washing with PBS for three times, the cells were stained with antifade mounting medium with DAPI. For negative control, cells were incubated with commercial GFP (2 µg) in PBS with 1% FBS and processed in the same condition. All fixed cells were imaged using confocal microscope. The green fluorescence shows GFP expression; the blue fluorescence shows DAPI labeled cell nuclei. The images were observed under 100× objective, and at least 10-15 GFP-positive cells or images were observed in each cell line. Scale bar represent 10 µm. All images studies have been analyzed in triplicate.

To explore this concept, *Streptococcus mutans* biofilms were pre-formed on sHA surface, and treated topically with GFP-PG1 and EPS-degrading enzymes (Dex/Mut) either alone or in combination. Time-lapsed confocal imaging and quantitative computational analyses were conducted to analyze EPS-matrix degradation and live/dead bacterial cells within biofilms (FIG. 6A). The enzymes-peptide combination resulted in more than 60% degradation of the EPS-matrix, while increasing the bacterial killing when compared to either GFP-PG or Dex/Mut alone. These findings were further validated via standard culturing assays by determining colony forming units. The antibacterial activity of PG against *S. mutans* biofilms combined with Dex/Mut was significantly enhanced than either one alone. Topical exposure of Dex/Mut alone showed no effects on biofilm cell viability, whereas GFP-PG-1 alone showed limited killing activity (FIG. 6B). Together, the data demonstrate potential of this combined approach to synergistically enhance antimicrobial efficacy of GFP-PG-1 against established biofilms (FIG. 6C).

Uptake of GFP Fused with Different Tags by Human Periodontal Cells.

Purified GFP fusion proteins when incubated with human cultured cells, including HPDLS, MMS, SCC-1, GMSC, AGK and osteoblast cells (OBC) revealed interesting results. Although only one representative image of each cell line is presented, uptake studies were performed in triplicate and at least 10-15 images were recorded under confocal microscopy. Without a fusion tag, GFP did not enter any tested human cell line. Both CTB-GFP and PTD-GFP effectively penetrated all tested cell types, although their localization patterns differed. Upon incubation with CTB-GFP, GFP signals localized primarily to the periphery of HPDLSC and MMSC, uniformly small cytoplasmic puncta in SSC-1, AGK, OBC and large cytoplasmic foci in GMSC. PTD-GFP was observed as small cytoplasmic foci in MMSC, variably sized cytoplasmic puncta in HPDLSC, GMSC, AGK, OBC and both the cytoplasm and the periphery of SCC-1 cells. PG1-GFP is the most efficient tag in entering all tested human cells because GFP could be localized at tenfold lower concentrations than any other fusion proteins. PG1-GFP showed exclusively cytoplasmic localization in HPDLSC, SCC-1, GMSC and AGK cells and localized to both the periphery and cytosol in MMSC, but it is only localized to the periphery of OBC. RC101-GFP was localized in SCC-1, GMSC, AGK and OBC, but its localization in HPDLSC was negligible and was undetectable in MMSC cells.

Discussion and Conclusions

The assembly of cariogenic oral biofilms is a prime example of how pathogenic bacteria accumulate on a surface (teeth), as an extracellular EPS matrix develops. Prevention of cariogenic biofilm formation requires disruption of bacterial accumulation on the tooth surface with a topical treatment. Chlorhexidine (CHX) is considered 'gold standard' for topical antimicrobial therapy (Flemmig and Beikler 2011; Marsh et al 2011; Caufield et al 2001). CHX effectively suppresses mutans streptococci levels in saliva, but it has adverse side effects including tooth staining and calculus formation, and is not recommended for daily preventive or therapeutic use (Autio-Gold 2008). As an alternative, several antimicrobial peptides (AMP) have been developed and tested against oral bacteria, and have shown potential effects against biofilms (albeit with reduced effects vs planktonic cells) (as reviewed by Silva et al., 2012) Unfortunately, most of these studies tested antibiofilm efficacy using continuous, prolonged biofilm exposure to AMPs (several hours) rather than topical treatment regimen as used clinically. Furthermore, synthetic AMPs are expensive to produce making them unaffordable for dental applications. Here, we show a plant-produced AMP, which demonstrates potent effects in controlling biofilm formation with a single, short-term topical treatment of a tooth-surrogate surface.

Developed cariogenic biofilms are characterized by bacteria embedded in EPS matrix, making biofilm treatment and removal extremely difficult (Paes Leme et al 2006; Koo et al 2013). EPS-rich matrix promotes microbial adhesion, cohesion and protection as well as hindering diffusion (Koo et al 2013; Flemming and Wingender 2010. EPS matrix creates spatial and microenvironmental heterogeneity in biofilms, modulating the growth and protection of pathogens against antimicrobials locally as well as a highly adhesive scaffold that ensures firm attachment of biofilms on tooth surfaces (Flemming and Wingender 2010; Peterson et al. 2015). CHX is far less effective against formed cariogenic biofilms (Hope and Wilson, 2004; Van Strydonck et al 2012; Xiao et al., 2012). The EPS are comprised primarily of a mixture of insoluble (with high content of $\alpha$1,3 linked glucose) and soluble (mostly $\alpha$1,6 linked glucose) glucans (Bowen and Koo 2011). Thus, the possibility of using EPS-matrix degrading dextranase or mutanase (from fungi) to disrupt biofilm and prevent dental caries has been explored and included in commercially available over-the-counter mouthwashes (e.g. Biotene PBF). However, topical applications of enzyme alone have generated moderate anti-biofilm/anti-caries effects clinically (Hull 1980), possibly due to lack of antibacterial action and reduced enzymatic activity in the mouth (Balakrishnan et al 2000). Interestingly, a recent in vitro study has shown that a chimeric glucanase comprised of fused dextranase and mutanase is more effective in disrupting plaque-biofilms than either enzymes alone (Jiao et al 2014). However, an approach of combining antimicrobial agents with both EPS-matrix degrading enzymes into a single therapeutic system has not yet been developed, likely due to difficulties associated with cost and formulations. In this study we demonstrate that PG1 together with matrix-degrading enzymes act synergistically and effectively to disrupt cariogenic biofilms. This feasible and efficacious topical antibiofilm approach is capable of simultaneously degrading the biofilm matrix scaffold and killing embedded bacteria using antimicrobial peptides combined with EPS-digesting enzymes.

Retention of high level antimicrobial activity by protegrin along with GFP fusion opens the door for a number of clinical applications to enhance oral health, beyond disruption of biofilms. In addition to biofilm disruption, enhancing wound healing in the gum tissues is an important clinical need. We recently reported that both protegrin and retrocyclin can enter human mast cells and induce degranulation, an important step in the wound healing process (Gupta et al 2015). Therefore, antimicrobial peptides protegrin and retrocyclin play an important role in killing bacteria in biofilms and initiate wound healing through degranulation of mast cells. In addition, it is important to effectively deliver growth hormones or other proteins to enhance cell adhesion, stimulate osteogenesis, angiogenesis, bone regeneration, differentiation of osteoblasts or endothelial cells. Previously identified cell penetrating peptides have several limitations. CTB enters all cell types via the ubiquitous GM1 receptor and this requires pentameric form of CTB. PTD on the other hand does not enter immune cells (Xiao et al 2016).

In this study we tested ability of PG1-GFP or RC101-GFP to enter periodontal and gingival cells. PG1-GFP is the most efficient tag in entering periodontal or gingival human cells because GFP signal could be detected even at ten-fold lower concentrations than any other fusion proteins. Although there were some variations in intracellular localization, PG1-GFP effectively entered HPDLSC, SCC-1, GMSC, AGK, MMSC and OBC. In contrast RC101-GFP entered SCC-1, GMSC, AGK and OBC but its localization in HPDLSC and MMSC cells were poor or undetectable. Therefore, this study has identified a novel role for protegrin in delivering drugs to osteoblasts, periodontal ligament cells, gingival epithelial cells or fibroblasts to enhance oral health. It is feasible to release protein drugs synthesized in plant cells by mechanical grinding and protein drugs bioencapsulated in lyophilized plant cells embedded in chewing gums provides an ideal mode of drug delivery for their slow and sustained release for longer duration. This overcomes a major limitation of current oral rinse formulations—short duration of contact of antimicrobials on the gum/dental surface.

Beyond topical applications, protein drugs fused with protegrin expressed in plant cells can be orally delivered to deeper layers of gum tissues in a non-invasive manner and increase patient compliance. Protein drugs bioencapsulated in plants can be stored for many years at room temperature without losing their efficacy (Su et al 2015; Daniell et al 2016). The high cost of current protein drugs is due to their production in prohibitively expensive fermenters, purification, cold transportation/storage, short shelf life and sterile delivery methods. All these challenges could be eliminated using this novel drug delivery concept to enhance oral health. Recent FDA approval of plant cells for production of protein drugs (Walsh 2014) augurs well for clinical advancement of this novel concept.

REFERENCES

Agrawal P, Verma D, Daniell H. 2011. Expression of *Trichoderma reesei* β-mannanase in tobacco chloroplasts and its utilization in lignocellulosic woody biomass hydrolysis. PLoS One. 6:e29302.

Ajdić D, McShan W M, McLaughlin R E, Savic G, Chang J, Carson M B, Primeaux C, Tian R, Kenton S, Jia H, Lin S, Qian Y, Li S, Zhu H, Najar F, Lai H, White J, Roe B A, Ferretti J J. 2002. Genome sequence of *Streptococcus mutans* UA159, a cariogenic dental pathogen. Proc Natl Acad Sci USA 99:14434-14439.

Autio-Gold J. 2008. The role of chlorhexidine in caries prevention. Oper Dent. 33(6):710-6.

Banas J A, Vickerman M M. 2003. Glucan-binding proteins of the oral streptococci. Crit Rev Oral Biol Med. 14(2): 89-99.

Balakrishnan M, Simmonds R S, Tagg J R. 2000. Dental caries is a preventable infectious disease. Aust Dent J. 45:235-45.

Bowen W H. 1972. The effect of dextranase on caries activity in monkeys (macaca irus). Caries Res. 6:75-6.

Bowen W H and Koo H. 2011. Biology of *Streptococcus mutans*-Derived glucosyltransferases: Role in extracellular matrix formation of cariogenic biofilms. Caries Res 45:69-86.

Burne R A. 1998. Oral streptococci . . . products of their environment. J Dent Res. 77(3):445-52.

Caufield P W, Dasanayake A P, Li Y. 2001. The antimicrobial approach to caries management. J Dent Educ 65:1091-5.

Chen J, Falla T J, Liu H, Hurst M A, Fujii C A, Mosca D A, Embree J R, Loury D J, Radel P A, Cheng Chang C, Gu L, Fiddes J C. 2000. Development of protegrins for the treatment and prevention of oral mucositis: structure-activity relationships of synthetic protegrin analogues. Biopolymers. 55:88-98.

da Silva B R, de Freitas V A, Nascimento-Neto L G, Carneiro V A, Arruda F V, de Aguiar A S, Cavada B S, Teixeira E H. 2012. Antimicrobial peptide control of pathogenic microorganisms of the oral cavity: a review of the literature. Peptides 36: 315-321.

Daniell H, Lin C S, Yu M, Chang W J. 2016. Chloroplast genomes: diversity, evolution and applications in genetic engineering. Genome Biology, in press DeGray G, Rajasekaran K, Smith F, Sanford J, Daniell H. 2001. Expression of an antimicrobial peptide via the chloroplast genome to control phytopathogenic bacteria and fungi. Plant Physiol. 127(3):852-62.

Dige I, Raarup M K, Nyengaard J R, Kilian M, Nyvad B. 2009. *Actinomyces naeslundii* in initial dental biofilm formation. Microbiology 155:2116-2126.

Dye B A, Hsu K L, Afful J. 2015. Prevalence and Measurement of Dental Caries in Young Children. Pediatr Dent 37: 200-216.

Flemmig T F, Beikler T. 2011. Control of oral biofilms. Periodontol 2000. 55:9-15.

Flemming H C, Wingender J. 2010. The biofilm matrix. Nat Rev Microbiol. 8:623-33.

Giles F J, Miller C B, Hurd D D, Wingard J R, Fleming T R, Sonis S T, Bradford W Z, Pulliam J G, Anaissie E J, Beveridge R A, Brunvand M M, Martin P J; PROMPT-CT Trial Investigators. 2003. A phase III, randomized, double-blind, placebo-controlled, multinational trial of iseganan for the prevention of oral mucositis in patients receiving stomatotoxic chemotherapy (PROMPT-CT trial). Leuk Lymphoma. 44:1165-72.

Guggenheim B, Regolati B, Schmid R, Mühlemann HR. 1980. Effects of the topical application of mutanase on rat caries. Caries Res. 14:128-35.

Guo L, McLean J S, Yang Y, Eckert R, Kaplan C W, Kyme P, Sheikh O, Varnum B, Lux R, Shi W, He X. 2015. Precision-guided antimicrobial peptide as a targeted modulator of human microbial ecology. Proc Natl Acad Sci USA 112: 7569-7574.

Gupta, Kshitij, Akhil Kotian, Hariharan Subramanian, Henry Daniell, and Hydar Ali. "Activation of Human Mast Cells by Retrocyclin and Protegrin Highlight Their Immunomodulatory and Antimicrobial Properties." Oncotarget 6, no. 30 (Oct. 6, 2015): 28573-87. doi: 10.18632/oncotarget.5611.

Hajishengallis E, Parsaei M, Klein M I, Koo H. 2015. Advances in the microbial etiology and pathogenesis of early childhood caries. Molecular Oral Microbiology doi: 10.1111/omi.12152.

Hall-Stoodley L, Costerton J W, Stoodley P. 2004. Bacterial biofilms: from the natural environment to infectious diseases. Nat Rev Microbiol 2: 95-108.

Hayacibara M F, Koo H, Vacca-Smith A M, Kopec L K, Scott-Anne K, Cury J A, Bowen W H. 2004. The influence of mutanase and dextranase on the production and structure of glucans synthesized by streptococcal glucosyltransferases. Carbohydrate Research 339: 2127-2137.

Hope C K and Wilson M. 2004. Analysis of the effects of chlorhexidine on oral biofilm vitality and structure based on viability profiling and an indicator of membrane integrity. Antimicrob Agents Chemother 48:1461-8.

Hull P S. 1980. Chemical inhibition of plaque. J Clin Periodontol. 7:431-42.

Jin S, Daniell H. 2015. The Engineered Chloroplast Genome Just Got Smarter. Trends Plant Sci 20:622-640

Jiao Y L, Wang S J, Lv M S, Jiao B H, Li W J, Fang Y W, Liu S. 2014. Characterization of a marine-derived dextranase and its application to the prevention of dental caries. J Ind Microbiol Biotechnol. 41:17-26.

Jones C G. 1997. Chlorhexidine: is it still the gold standard? Periodontol 2000 15: 55-62. Jin S, Kanagaraj A, Verma D, Lange T, Daniell H. 2011. Release of hormones from conjugates: chloroplast expression of β-glucosidase results in elevated phytohormone levels associated with significant increase in biomass and protection from aphids or whiteflies conferred by sucrose esters. Plant Physiol. 155:222-35.

Kassebaum N J, Bernab6 E, Dahiya M, Bhandari B, Murray C J, Marcenes W. 2015. Global burden of untreated caries: A systematic review and metaregression. J Dent Res. 94:650-658.

Kohli N, Westerveld D R, Ayache A C, Verma A, Shil P, Prasad T, Zhu P, Chan S L, Li Q, Daniell H. 2014. Oral delivery of bioencapsulated proteins across blood-brain and blood-retinal barriers. Mol Ther. 22:535-46.

Klein M I, Scott-Anne K M, Gregoire S, Rosalen P L, Koo H. Molecular approaches for viable bacterial population and transcriptional analyses in a rodent model of dental caries. Molecular Oral Microbiology 27: 350-361.

Klein M I, DeBaz L, Agidi S, Lee H, Xie G, Lin A H M, Hamaker B R, Lemos J A, Koo H. 2010. Dynamics of *Streptococcus mutans* transcriptome in response to starch and sucrose during biofilm development. PLoS One: e1347840.

Koo H, Falsetta M L, Klein M I. 2013. The exopolysaccharide matrix: a virulence determinant of cariogenic biofilm. J Dent Res. 92:1065-73.

Koo H, Xiao J, Klein M I, Jeon J G. 2010. Exopolysaccharides produced by *Streptococcus mutans* glucosyltransferases modulate the establishment of microcolonies within multispecies biofilms. J Bacteriol 192:3024-3032.

Kwon K C, Verma D, Singh N D, Herzog R, Daniell H. 2013. Oral delivery of human biopharmaceuticals, autoantigens and vaccine antigens bioencapsulated in plant cells. Adv Drug Deliv Rev. 65(6):782-99.

Kwon K C, Nityanandam R, New J S, Daniell H. 2013. Oral delivery of bioencapsulated exendin-4 expressed in chloroplasts lowers blood glucose level in mice and stimulates insulin secretion in beta-TC6 cells. Plant Biotechnol J. 11:77-86.

Odd F C. 1988. *Candida* and candidosis. $2^{nd}$ ed. Bailliere Tindall, London, United Kingdom.

Peterson B W, He Y, Ren Y, Zerdoum A, Libera M R, Sharma P K, van Winkelhoff A J, Neut D, Stoodley P, van der Mei H C, Busscher H J. 2015. Viscoelasticity of biofilms and their recalcitrance to mechanical and chemical challenges. FEMS Microbiol Rev 39: 234-245.

Lakshmi P S, Verma D, Yang X, Lloyd B, Daniell H. 2013. Low cost tuberculosis vaccine antigens in capsules: expression in chloroplasts, bio-encapsulation, stability and functional evaluation in vitro. PLoS One. 8:e54708.

Lai J R, Huck B R, Weisblum B, Gellman S H. 2002. Design of non-cysteine-containing antimicrobial beta-hairpins: structure-activity relationship studies with linear protegrin-1 analogues. Biochemistry. 41:12835-42.

Lee S B, Li B, Jin S, Daniell H. 2011. Expression and characterization of antimicrobial peptides Retrocyclin-101 and Protegrin-1 in chloroplasts to control viral and bacterial infections. Plant Biotechnol J. 9:100-15.

Ma Z, Wei D, Yan P, Zhu X, Shan A, Bi Z. 2015. Characterization of cell selectivity, physiological stability and endotoxin neutralization capabilities of α-helix-based peptide amphiphiles. Biomaterials. 52:517-30.

Marsh P D, Moter A, Devine D A. 2011. Dental plaque biofilms: communities, conflict and control. Periodontology 2000. 55:16-35.

Morassutti, Carla, Francesca De Amicis, Barbara Skerlavaj, Margherita Zanetti, and Stefano Marchetti. Production of a Recombinant Antimicrobial Peptide in Transgenic Plants Using a Modified VMA Intein Expression System. FEBS Letters 519: 141-46.

Ohashi, Tomoo, Stephane D. Galiacy, Gina Briscoe, and Harold P. Erickson. An Experimental Study of GFP-Based FRET, with Application to Intrinsically Unstructured Proteins. Protein Science: A Publication of the Protein Society 16, no. 7 (July 2007): 1429-38. doi:10.1110/ps.072845607.

Otsuka R, Imai S, Murata T, Nomura Y, Okamoto M, Tsumori H, Kakuta E, Hanada N, Momoi Y. 2015. Application of chimeric glucanase comprising mutanase and dextranase for prevention of dental biofilm formation. Microbiol Immunol. 59:28-36.

Paes Leme A F, Koo H, Bellato C M, Bedi G, Cury J A. 2006. The role of sucrose in cariogenic dental biofilm formation-new insight. J Dent Res. 85:878-87.

Sassi A B, Bunge K E, Hood B L, Conrads T P, Cole A M, Gupta P, Rohan L C. 2011. Preformulation and stability in biological fluids of the retrocyclin RC-101, a potential anti-HIV topical microbicide. AIDS Res Ther. 8:27.

Sassi A B, Cost M R, Cole A L, Cole A M, Patton D L, Gupta P, Rohan L C. 2011. Formulation development of retrocyclin 1 analog RC-101 as an anti-HIV vaginal microbicide product. Antimicrob Agents Chemother. 55:2282-9.

Skosyrev, Vitaly S., Natalja V. Rudenko, Alexander V. Yakhnin, Vasily E. Zagranichny, Lubov I. Popova, Mikhail V. Zakharov, Andrey Yu Gorokhovatsky, and Leonid M. Vinokurov. EGFP as a Fusion Partner for the Expression and Organic Extraction of Small Polypeptides. Protein Expression and Purification 27, no. 1 (January 2003): 55-62.

Trotti A, Garden A, Warde P, Symonds P, Langer C, Redman R, Pajak T F, Fleming T R, Henke M, Bourhis J, Rosenthal D I, Junor E, Cmelak A, Sheehan F, Pulliam J, Devitt-Risse P, Fuchs H, Chambers M, O'Sullivan B, Ang K K. 2004. A multinational, randomized phase III trial of iseganan HCl oral solution for reducing the severity of oral mucositis in patients receiving radiotherapy for head-and-neck malignancy. Int J Radiat Oncol Biol Phys. 58:674-81.

Van Strydonck D A, Slot D E, Van der Velden U, Van der Weijden F. 2012. Effect of a chlorhexidine mouthrinse on plaque, gingival inflammation and staining in gingivitis patients: a systematic review. J Clin Periodontol. 39:1042-55.

Verma D, Kanagaraj A, Jin S, Kolattukudy P E, Daniell H. 2010. Chloroplast-derived enzyme cocktails hydrolyse lignocellulosic biomass and release fermentable sugars. Plant Biotechnol J. 8:332-50.

Walsh G. 2014. Biopharmaceutical benchmarks 2014. Nat Biotechnol. 32:992-1000.

Wang W, Cole A M, Hong T, Waring A J, Lehrer R I. 2003. Retrocyclin, an antiretroviral theta-defensin, is a lectin. J Immunol. 170(9):4708-16.

Xiao, Yuhong, Kwang-Chul Kwon, Brad E. Hoffman, Aditya Kamesh, Noah T. Jones, Roland W. Herzog, and Henry Daniell. Low Cost Delivery of Proteins Bioencapsulated in Plant Cells to Human Non-Immune or Immune Modulatory Cells. Biomaterials 80 (February 2016): 68-79. doi: 10.1016/j.biomaterials.2015.11.051.

Xiao, J. et al. 2012. The exopolysaccharide matrix modulates the interaction between 3D architecture and virulence of a mixed-species oral biofilm. PLoS Pathog 8, e1002623.

Yakhnin, A. V., L. M. Vinokurov, A. K. Surin, and Y. B. Alakhov. Green Fluorescent Protein Purification by Organic Extraction. Protein Expression and Purification 14, no. 3 (December 1998): 382-86. doi:10.1006/prep.1998.0981.

Example II

Creation of Chloroplast Vectors Expressing AMP, Biofilm Degrading Enymes and Fusion Proteins Thereof Effective treatment of biofilm-associated infections is problematic as antimicrobials often fail to reach clusters of microbes present within the surrounding extracellular matrix that enmeshes and protects them. Furthermore, development of novel therapies against biofilm-related oral diseases and maintenance of oral health needs to be cost-effective and readily accessible.

To ensure a continued supply of reagents, dextranase/mutanase and protegrin/retrocyclin are expressed independently and as fusion proteins in tobacco and other plant chloroplasts, such as lettuce. Proteins will be produced and used in low cost purification strategies. Tobacco plants produce a million seeds, and thus, it is feasible to scale up production easily. Each acre of tobacco will produce up to 40 metric tons of biomass, facilitating low cost large scale production of AMP, enzymes and fusion constructs encoding the same. In another approach, the proteins are produced in an edible plant such as lettuce.

Several dextranases (Dex) and mutanases (Mut) have been isolated from fungi and bacteria and characterized for their enzymatic activity. Optimal dextranase and mutanase enzymes should have enzymatic properties suitable for human oral environment. Based on short duration of oral treatments, strong binding/retention property to plaque-biofilms and catalytic activity to both types of EPS (dextrans and mutans) are highly desirable. The enzymes added in commercial dextranase-containing mouthwashes (e.g. Biotene) are largely derived from fungi (*Penicillium* sp. and *Chaetomium erraticum*). However, fungal dextranases show higher temperature optima (50-60° C.) than bacterial dextranases (35-40° C.). Furthermore, bacterial dextranases are more stable and effective at oral temperature (~37° C.) and are suitable for dental caries-prevention. Recently, a dextranase from *Arthrobacter* sp strain Arth410 showed superior dextran degradation properties at optimal temperatures (35-45° C.) and pH values (pH 5-7) found in mouth and in cariogenic biofilms when compared to fungal dextranases. In addition, topical applications of bacterial dextranase are more effective in reducing dental caries in vivo than fungal dextranse. Likewise, a bacterial mutanase from *Paenibacillus* sp. strain RM1 shows that biofilm was effectively degraded by 6 hr incubation even after removal of the mutanase, preceded by first incubation with the biofilms for 3 min. Also, when compared to other microbial species, RM1 mutanase shows enhanced biofilm-degrading property. Notably, fungal enzymes require glycosylation, which precludes their expression in chloroplasts. In addition, immunogenicity of glycoproteins in human system may raise additional regulatory concerns. Therefore, the present invention involves use of bacterial dextranase and mutanase for expression in chloroplasts.

Figure 9A:
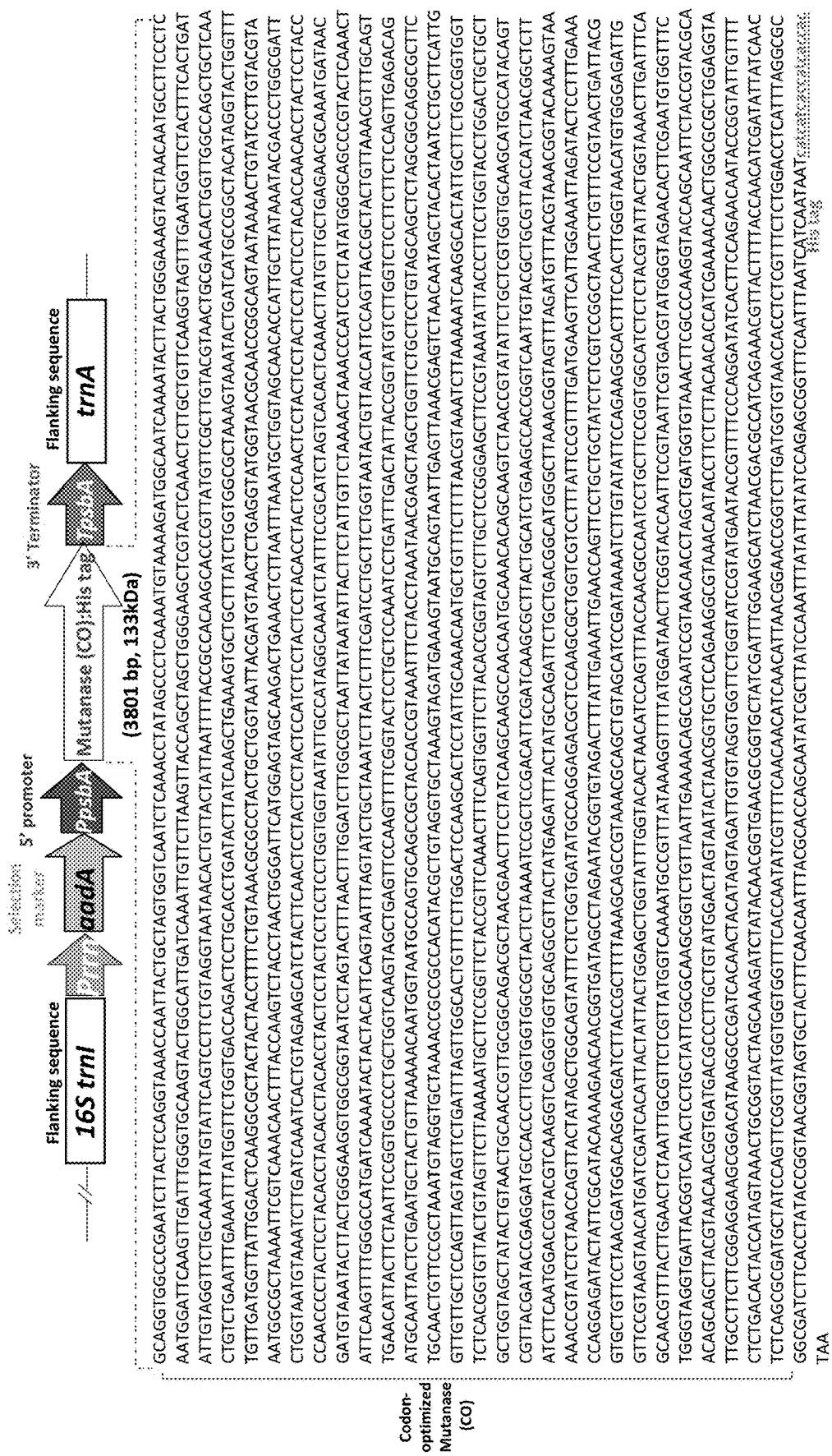

In order to increase the production of Arth410 dextranase and RM1 mutanase protein in chloroplasts, both sequences have been codon optimized for chloroplast expression. See FIGS. 9A and 9B.

Retrocyclin and Protegrin.

Figure 10:
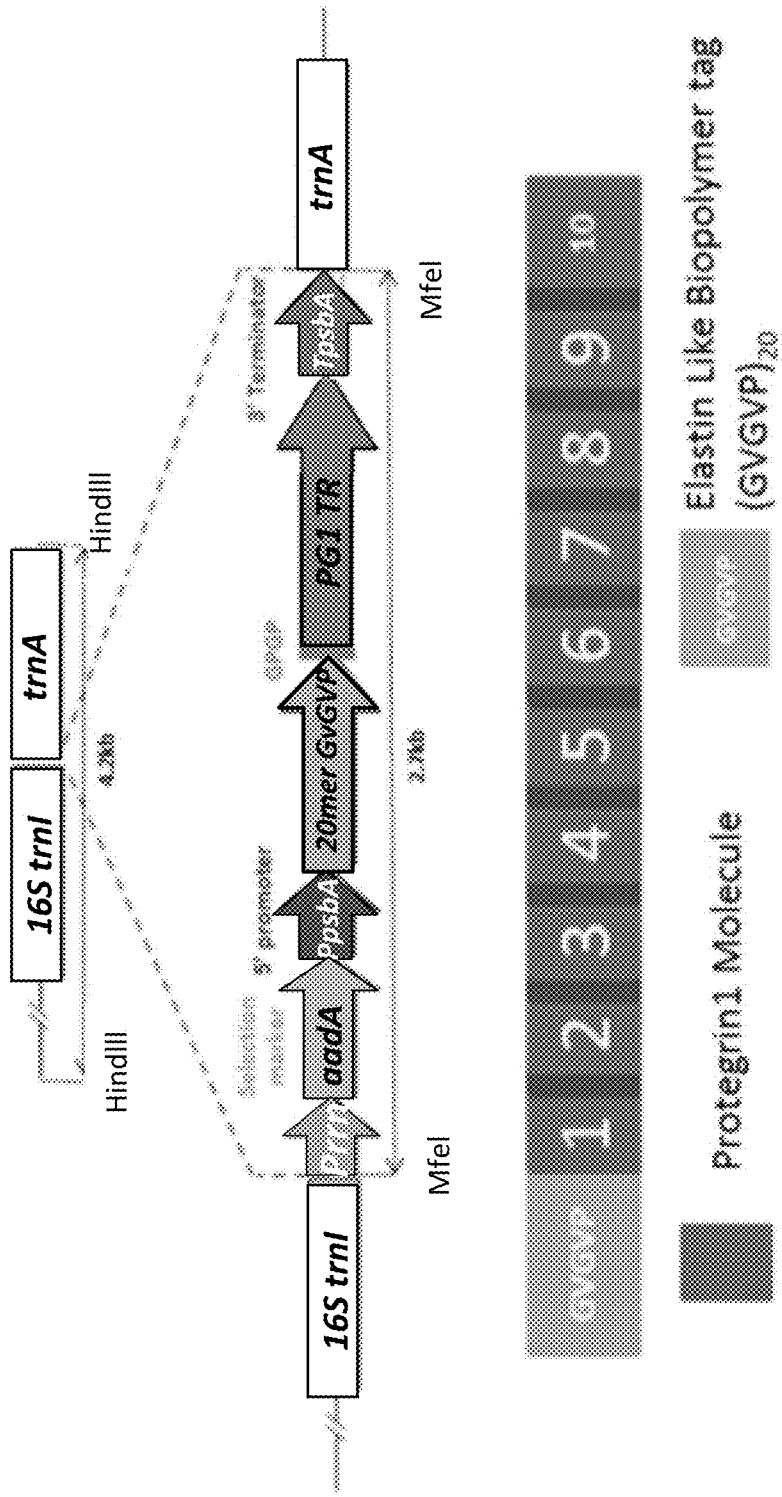
FIG. 10. A schematic diagram of a chloroplast vector expressing tandem repeats of AMPs fused with GVGVP (SEQ ID NO: 11) for use alone or for expressing fusion proteins comprising the EPS proteins in FIG. 9.

In order to maximize synthesis and reduce toxicity of AMPs, ten tandem repeats of PG1 or RC101, separated by protease cleavage sites as shown in FIG. 10 are employed. For each copy of expressed gene, ten functional copies of PG1 or RC101 will be made. For this purpose we have chosen the Tobacco Etch Virus (TEV) protease, which has high specificity and a short cleavage site of seven amino acids. Alternatively, furin cleavage sites can also be employed. This vector can also be engineered to include a nucleic acid encoding a biofilm degrading enzyme. The coding region can be expressed under the promoter utilized to express the AMP or can be ligated into the vector operably linked to a second promoter region. The biofilm degrading enzyme coding sequence may also contain TEV protease cleavage sites to facilitate release of the enzyme. This approach provides a safer and cleaner option than chemical cleavage methods. Most importantly, individual PG1 peptides in the fusion protein will not form secondary structures before cleavage, thereby avoiding accumulation of functional peptides which can be lethal to the host production systems. Antimicrobial activity of the cleaved PG1/RC101, biofilm degrading enzymes or fusion proteins thereof can be used to degrade biofilms using the methods disclosed in Example I.

As mentioned above, the sequences encoding the AMP/biofilm degrading enzymes are optionally codon-optimized prior to insertion into chloroplast transformation vectors, such as pLD. Chloroplast transformation relies upon a double homologous recombination event. Therefore, chloroplast vectors comprise homologous regions to the chloroplast genome which flank the expression cassette encoding the heterologous proteins of interest, which facilitate insertion of the transgene cassettes into the intergenic spacer region of the chloroplast genome, without disrupting any functional genes. Although any intergenic spacer region could be used to insert transgenes, the most commonly used site of transgene integration is the transcriptionally active intergenic region between the trnI-trnA genes (in the rrn operon), located within the IR regions of the chloroplast genome (FIG. 10). Because of similar protein synthetic machinery between *E. coli* and chloroplasts, efficiency of codon-optimization can also be assessed in *E. coli* and then plants can be created. Both systems could be used for expression of AMPs, biofilm degrading enzymes or fusion proteins thereof, as well as for purification and evaluation of AMPs or enzymatic activities.

Purification Strategies

A hydrophobic interaction column (HIC; TOSOH Butyl Toyopearl 650m) can be used to purify PG1 fused with Green Florescent Protein (GFP). The GFP selectively binds to the HIC and facilitates Rc101/PG1 to >90% purity.

Figure 11:
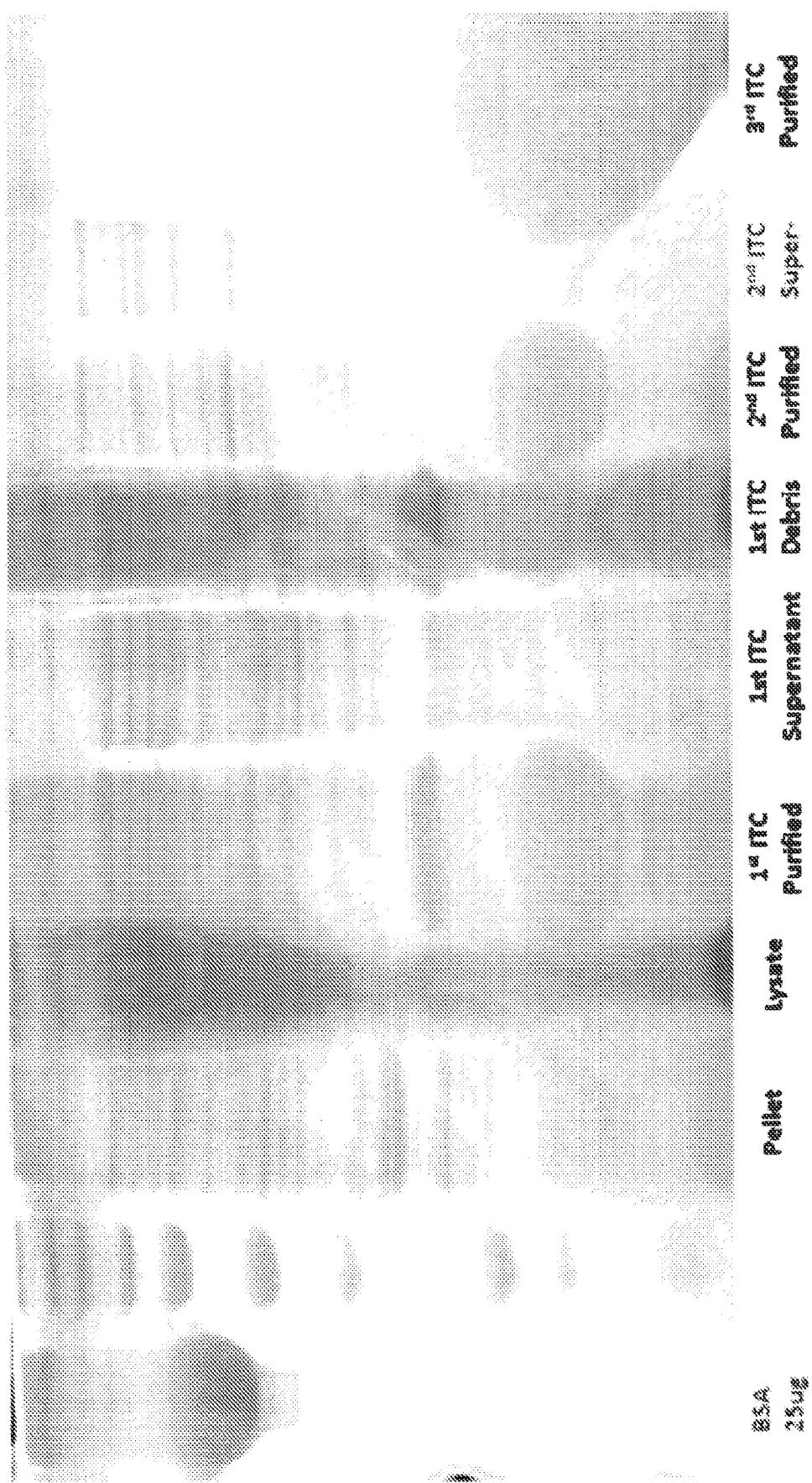
FIG. 11. Novel purification strategy: inverse temperature cycling purification process demonstrates high yield.

Despite using the expensive HIC chromatography method, recovery is very poor (<20%). To address this problem and enhance yield, 10 tandem repeats of PG1 with an elastin like biopolymer (GVGVP (SEQ ID NO: 11); FIG. 10) are engineered into the vector. This biopolymer, has a unique thermal property of precipitating out of solution upon increasing temperature above its inverse transition temperature (Tt). GVGVP (SEQ ID NO: 11) remains in soluble monomeric state below Tt and form insoluble aggregates above it. This phase transition from soluble to insoluble state is reversible by changing the temperature of the solution and this facilitates protein purification. Subsequently fused protein is re-solubilized by cooling below Tt and to remove any insoluble contaminants that have co-precipitated as shown in FIG. 11. The process of heating (37° C.) and cooling (4° C.) is known as Inverse Transition Cycling (ITC) and performing 3-5 rounds of ITC results in highly purified proteins (>98% purity, FIG. 11).

In an alternative approach, a signal peptide is fused with dextranase or mutanase for expression in *E. coli*, where the signal peptide will result in secretion of the enzymes into the extracellular media. In addition, secretory proteins should pass through two membrane systems of *E. coli*, during which they pass through the periplasmic environment where disulfide isomerases, foldases and chaperones are present. Therefore, correct folding and disulfide bond formation of secretory proteins are facilitated by the enzymes, resulting in enhancement of biological activity of proteins (ideal for AMPs). Another merit of this production strategy is the low level of proteolytic activity in the culture medium which serves to enhance the stability of the recombinant protein. The signal sequence of the secreted protein is cleaved during the export process, creating an authentic N-terminus to the native protein. There are several molecules useful for translocating proteins to extracellular media, such as TAT, SRP, or SecB-dependent pathways. However, rather than working independently, the different pathways closely interact with each other. Both SRP and SecB-dependent pathways can work together in targeting of a single protein. Also, under Sec-deficient conditions, translocation of Sec pathway substrates can be rescued by TAT systems.

Among numerous signal sequences, outer membrane protein A (OmpA) and Seq X (derived from lac Z) signal peptide demonstrate superior export functions and are capable of exporting fused protein into extracellular medium at up to 4 g/L and 1 g/L, respectively. Therefore, these signal sequences are used for efficient exporting of Arth 410 Dex and RM1 Mut to extracellular milieu. Accumulation of the dextranase and mutanase exported into media will be determined by protein quantitation and enzyme assays.

Successful expression of these proteins in *E. coli* has been achieved. See Western blot results shown in FIG. 12. Chloroplast vectors harboring these sequences will be bombarded into tobacco or lettuce leaves to create plants capable of large scale production of extranase/mutanase/AMP proteins. After harvesting large scale biomass, leaves will be lyophilized and stored at room temperature. In another approach, clinically-proven anti-caries compounds such as (fluoride 250 ppm) and a broad-spectrum bactericidal, chlorhexidine 0.12% can be included to assess whether these agents increase efficacy.

The AMP-enzyme combination effectively disrupts cariogenic biofilm formation and the onset of cavitation in vivo. Furthermore, AMP-enzyme fusion protein appears to be superior to current chemical modalities for antimicrobial therapy and caries prevention.

Figure 13:
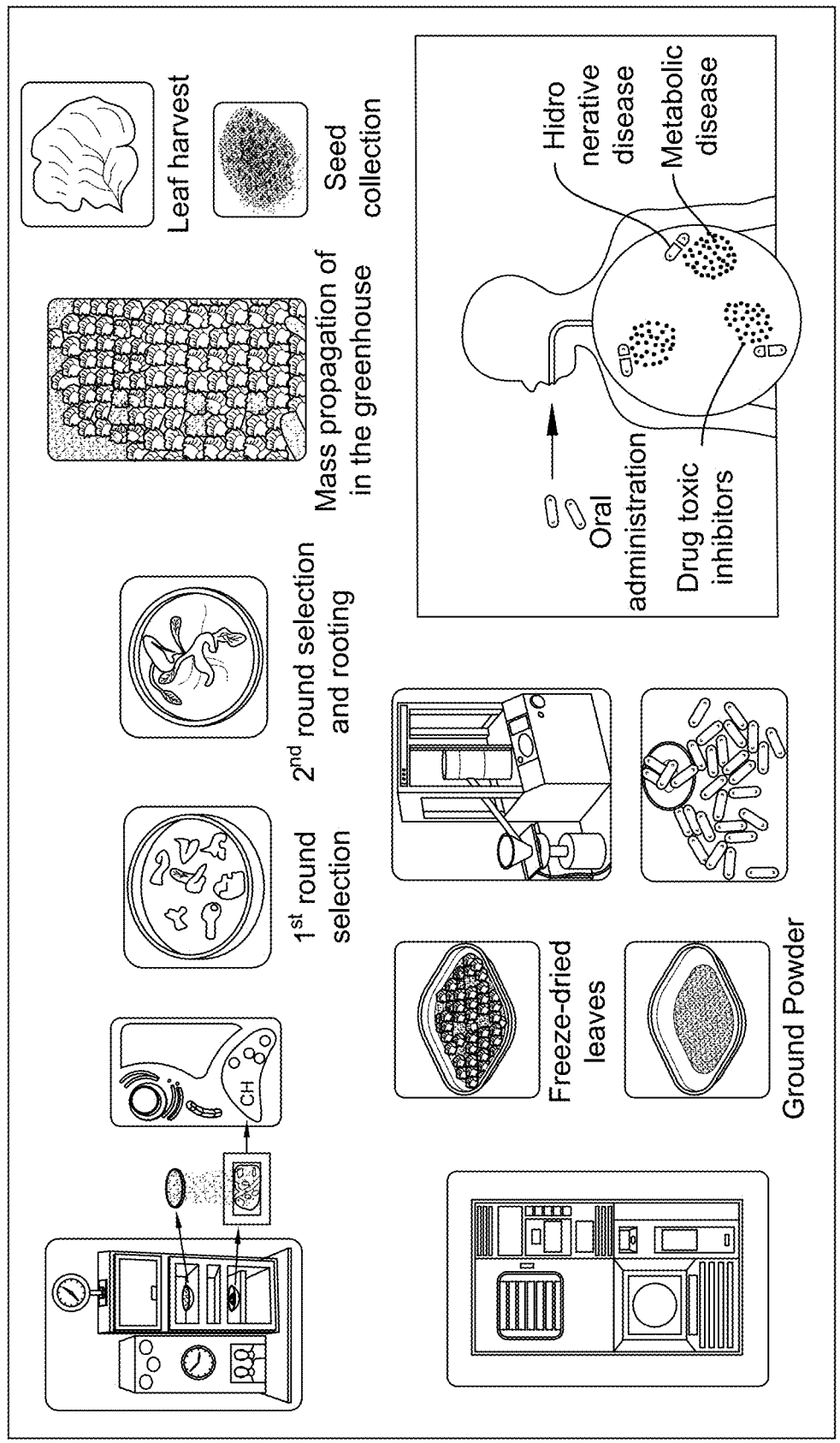
FIG. 13. A flow diagram of the steps for engineering lettuce plants for AMP/biofilm degrading enzyme production.

As mentioned previously, effective AMP-enzyme (independently or in combination) can be expressed in lettuce chloroplasts under the control of endogenous lettuce regulatory elements, for large scale GLP production and stability assessment. A key advantage is the lower production cost by elimination of prohibitively expensive purification processes. Freeze-dried leaf material expressing AMP/enzymes can be stored at ambient temperatures for several months or years while maintaining their integrity and functionality. See FIG. 13. In addition to long-term storage, increase of protein drug concentration and decrease of microbial contamination are other advantages. Lettuce leaves, after lyophilization showed 20-25 fold increase in protein drug concentration when compared to fresh leaves, thereby reducing the amount of materials used for oral or topical delivery. Following lyophilization, the plant material can be incorporated into a chewing gum to deliver the biofilm degrading compositions contained therein.

Figure 12A:
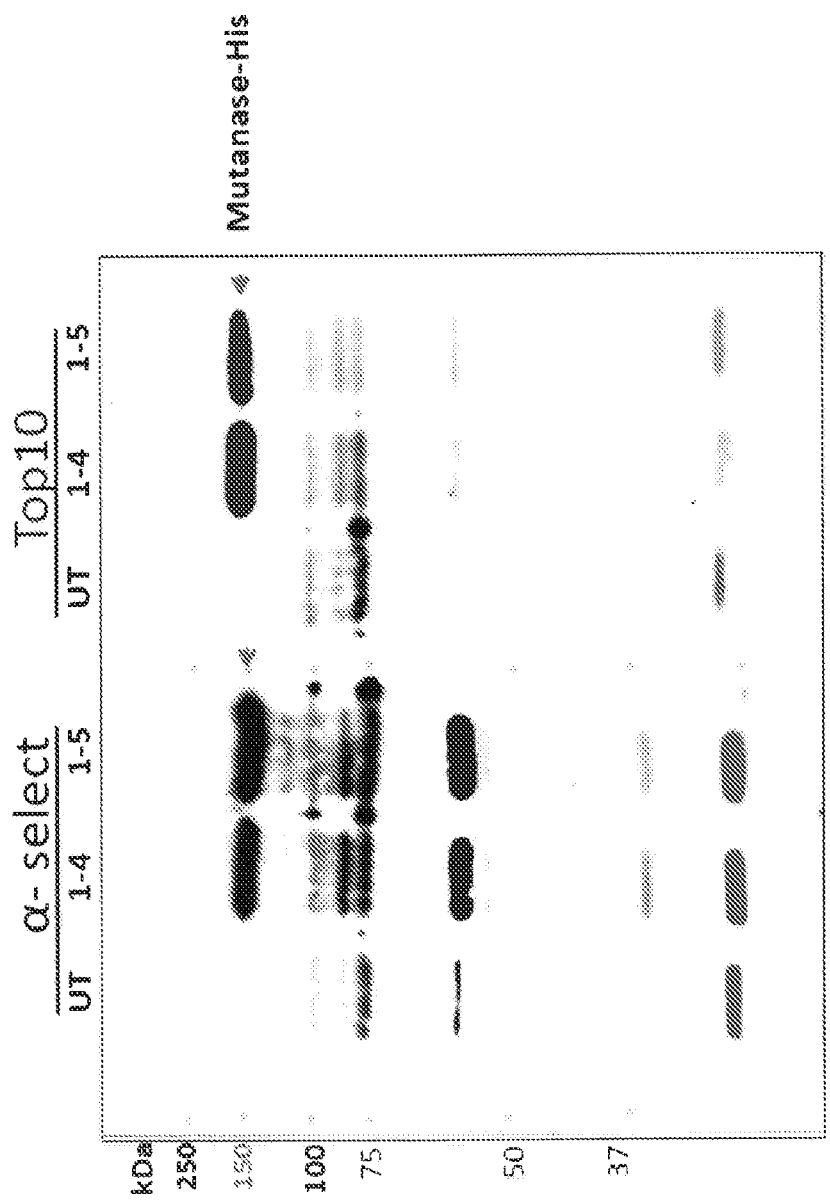
FIGS. 12A-12B: Expression of functional codon optimized mutanase in *E. coli*.
Figure 12C:
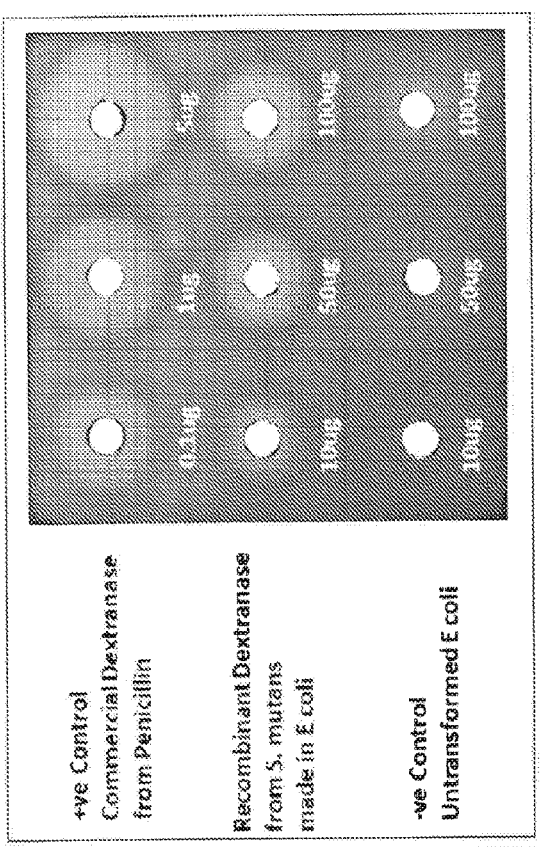
FIG. 12C represents a gel diffusion assay comparing the degradation activity of recombinant dextranase present in the crude lysate (Total Protein loading) from the transformed *E. coli* against blue dextran as compared to commercially purified enzyme from Penicillin.
Figure 12B:
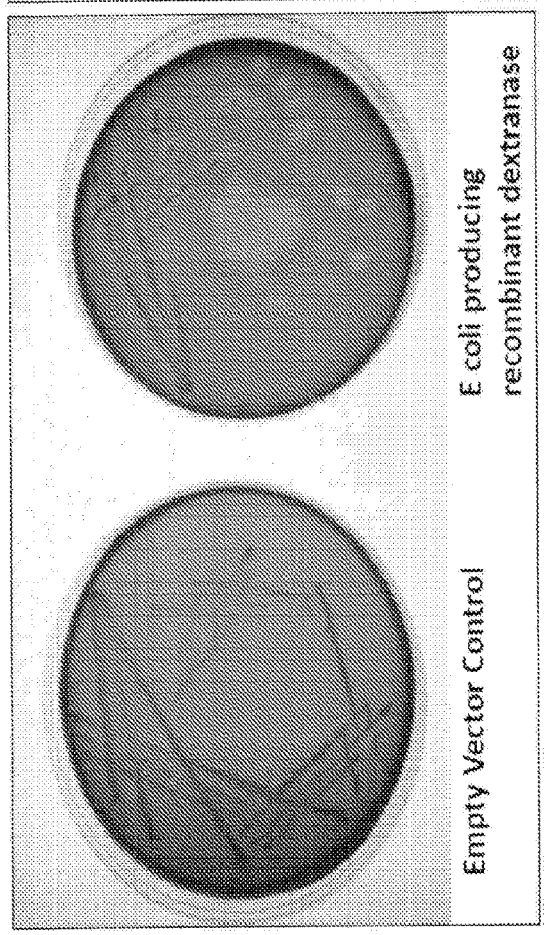

The steps for producing the AMP/enzymes or fusions thereof are shown in FIG. 12. The lettuce chloroplast vectors useful for expressing the proteins of the invention have been previously described in U.S. patent application Ser. No. 12/059,376, which is incorporated herein by reference. Expression levels of up to 70% of total protein in case of therapeutic proteins like proinsulin in lettuce chloroplasts can be achieved using this system.

AMP-enzyme(s) expressed in the edible plants are preferably orally delivered (topically) when used for treatment of oral diseases and the prevention and inhibition of dental carie formation. For enhanced lysis of plant cells within the oral cavity, AMP/enzyme expressing plant cells are optionally mixed with plant cells expressing cell wall degrading enzymes, described in U.S. patent application Ser. No. 12/396,382, also incorporated herein by reference.

Figure 16:
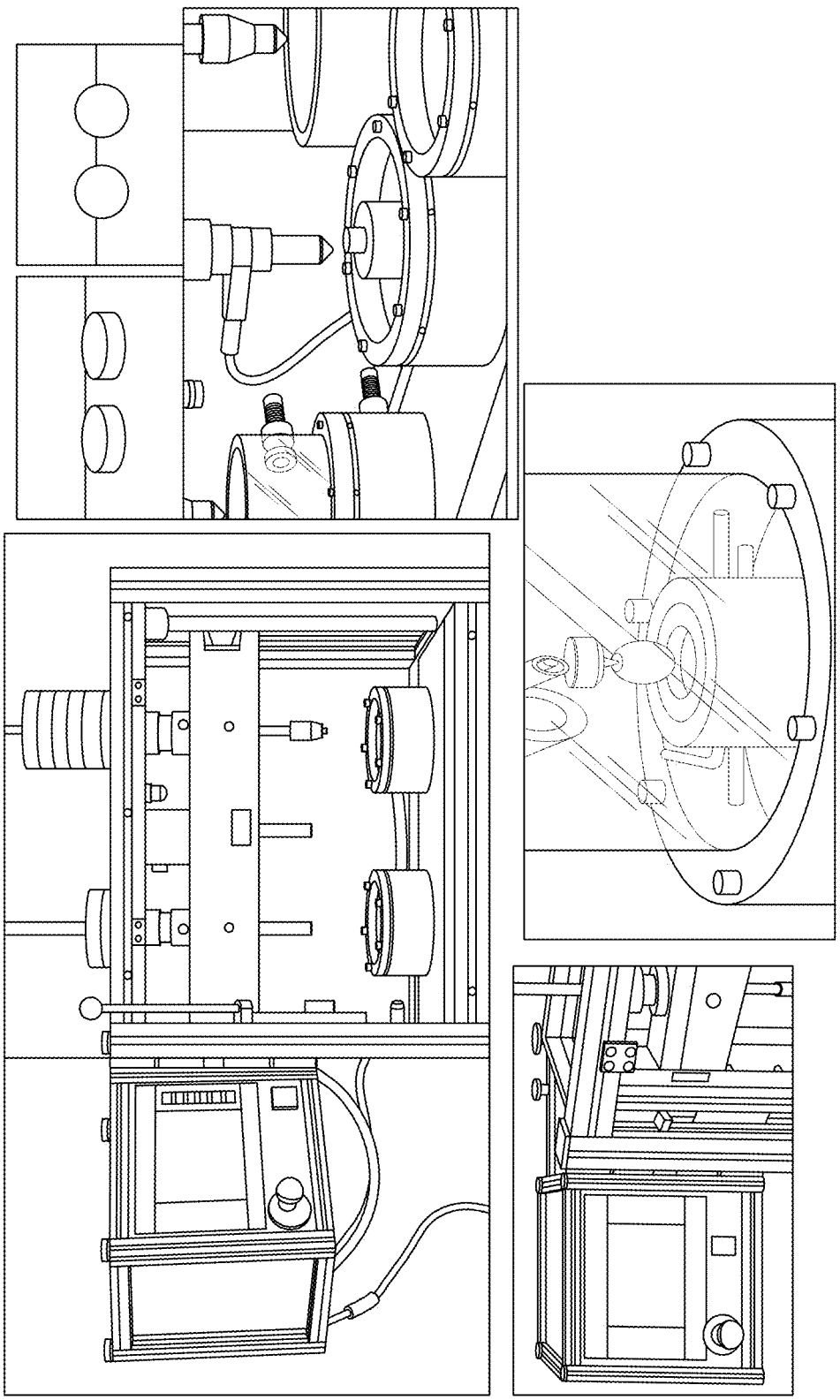
FIG. 16. A chewing simulator is shown which uses artificial saliva for assessing release kinetics of biofilm degrading agents from the gum tablets of the invention.
Figure 17:
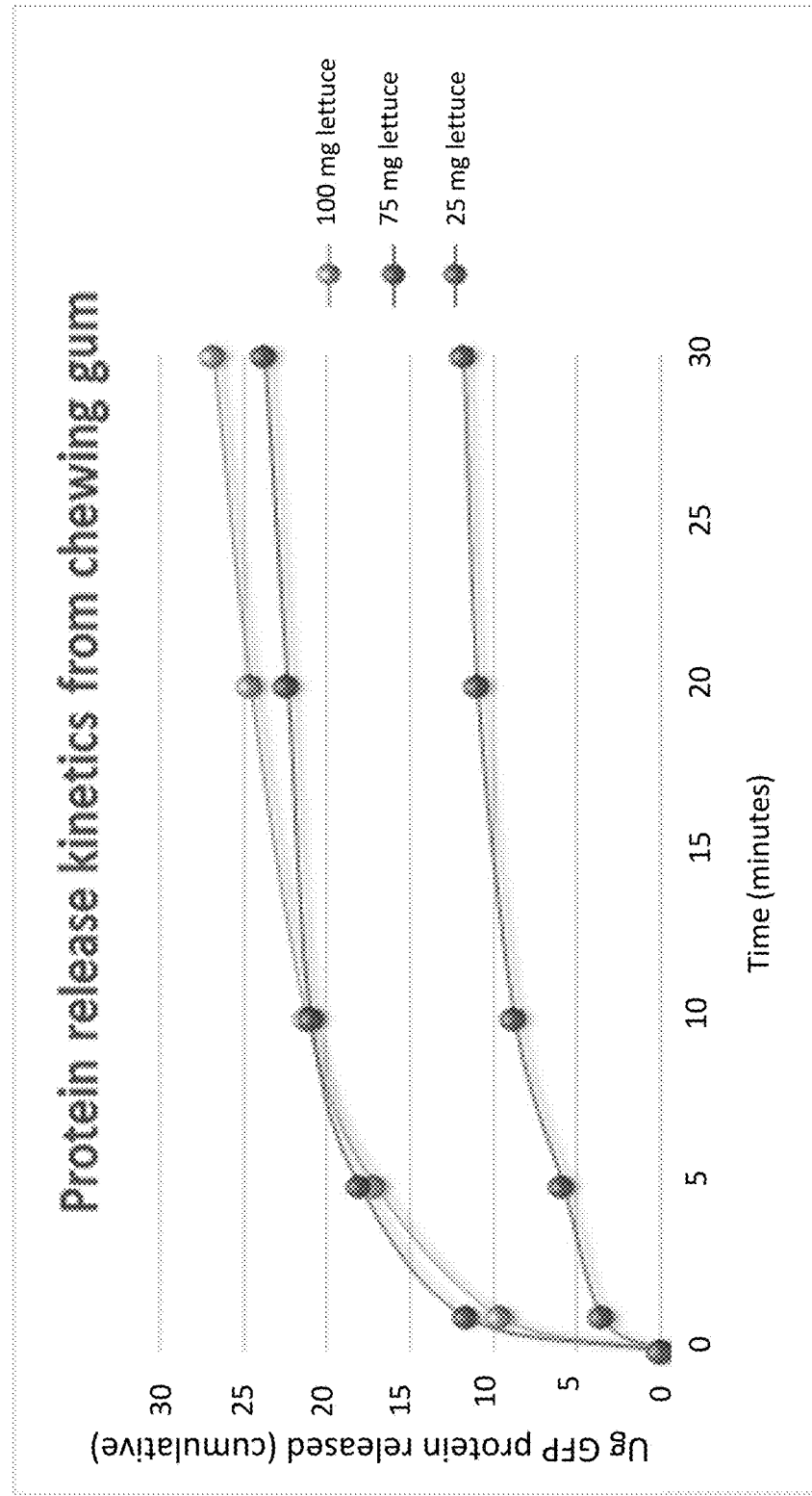
FIG. 17. A graph showing quantification of GFP released from chewing gum. Gum tablets comprising increasing concentrations of GFP expressed in lettuce leaves were assessed in a chewing simulator in the presence of artificial saliva to determine GFP release kinetics.

Chewing gum tablet preparation is shown in FIG. 14. Using GFP as an example of the protein of interest, this data shows the amounts of GFP that can be incorporated in to a chewing gum tablet. GFP levels were assessed both via fluorescence and by western blot. The results are shown in FIG. 15. The present inventors employed the chewing simulator shown in FIG. 16 and artificial saliva to assess GFP release kinetics from the gum tablets comprising GFP. FIG. 17 shows a graph illustrating the release kinetics over time from gum tablets comprising different amounts of GFP present in recombinant lettuce.

Figure 18:
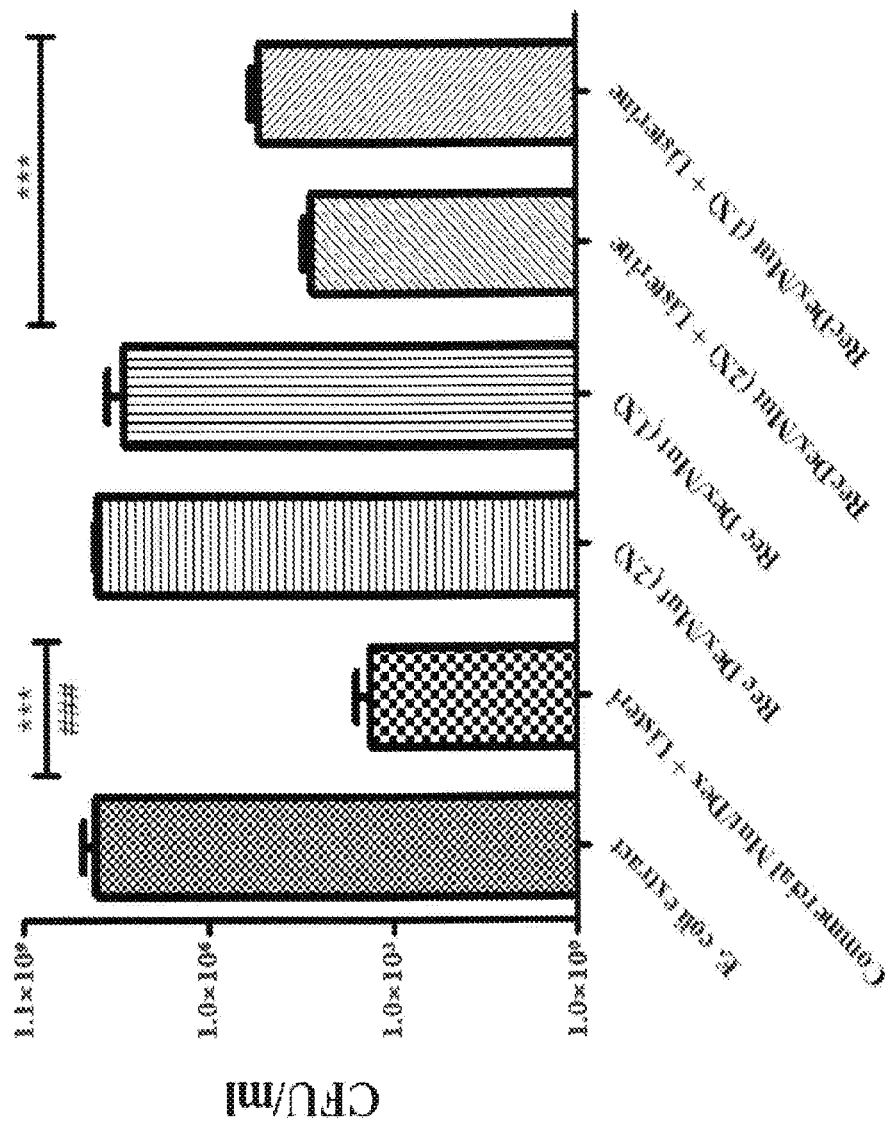
FIG. 18. A graph demonstrating that crude extracts comprising enzymes expressed from chloroplast vectors are as efficacious for inhibiting CFU formation as commercial enzymes, when mixed with Listerine®. Enzymatic degradation of in vitro *S. mutans* biofilms using *E. coli* derived Mutanase and Dextranase (ratio 1:5) supplemented with Listerine®. Commercial Mutanase (from *Bacillus* sp., Amano) and Dextranase (from *Penicillium* sp., Sigma) was used as positive control while the crude *E. coli* extract served as negative control. CFU/ml is expressed as mean.+−.standard deviation (n=2). ***, P<0.001 versus *E. coli* extract.

It is clear from these data that gum tablets comprising the AMP-enzyme fusion proteins of the invention will deliver the active material for a suitable time period to achieve bacterial kill and plaque or biofilm degradation. However, oral rinses such as Listerine® (i.e., 0.064% thymol, 0.06% methyl salicylate, 0.042% menthol, 0.092% eucalyptol, ethanol, water, benzoic acid, poloxamer 407, sodium benzoate and caramel) can also be employed to deliver the AMP-enzyme fusion proteins or combinations of the invention. FIG. 18 demonstrates that crude extracts comprising the enzymes of the invention mixed with Listerine® are as effective as commercially produced and purified enzymes that are quite costly to prepare. The data reveal that the dual-enzyme at various combinations (both different ratio and amounts) markedly reduced the biomass of *S. mutans* biofilm, in a dose-dependent manner. Among different combinations, 25U Dex and 5U Mut (5:1, Dex:Mut ratio) was the most effective, resulting on more than 80% of the total biomass degradation within 120 minutes. Further experiments confirmed that 5:1 Dex/Mut activity ratio displayed the highest effectiveness for both EPS degradation and bacterial killing by Listerine®. Excitingly, the dual-enzyme pre-treatment dramatically enhanced the efficacy of Listerine®-mediated bacterial killing (>3 log reduction vs vehicle pre-treatment and Listerine®). The inclusion of a third enzyme further enhanced the overall anti-biofilm activity. Furthermore, results from the mixed-species model indicated that the dual-enzyme combination was capable of not only enhancing the overall antibacterial activity, but also inducing targeted reduction of *S. mutans* dominance (while increasing the proportion of commensal/probiotic *S. oralis*) when Listerine® was used after enzymes pre-treatment. Accordingly, the enzyme+Listerine® strategy should selectively target the pathogen *S. mutans*, while increasing the proportion of commensal *S. oralis*, thereby preventing microecological imbalance within mixed-species biofilm.

AMPS have the ability to stimulate innate immunity and wound healing, in addition to antimicrobial activity. Harnessing this novel mast cell host defense feature of AMPs in addition to their antimicrobial properties expands their clinical applications. Biofilm-associated caries is the most challenging model for development of topical therapeutics. When developed, such topical drug delivery can be easily adapted to other biofilms, as matrix formation hinders drug efficacy in many other biofilm-associated diseases. Matrix is inherent in all biofilms thus the application goes beyond the biofilm in the mouth. The biofilm inhibiting compositions described herein can also be employed in coating stents, artificial joints, implants, valves and other medical devices inserted into the human body for the treatment of disease.

As discussed above, the AMP/enzymes, or leaves expressing the same can be incorporated into a chewing gum for effective topical application of the same for the treatment of oral disease. The compositions may also be incorporated into an oral rinse, such as Listerine®. As mentioned previously, other anti dental carrie agents such as fluoride or CHX may included in such gums or oral rinses.

CONCLUSION

It is respectfully requested that the amendments presented herewith be entered in this application, since the amendments are primarily formal, rather than substantive in nature. This amendment is believed to clearly place the pending claims in condition for allowance. In any event, the claims as presently amended are believed to eliminate certain issues and better define other issues which would be raised on appeal, should an appeal be necessary in this case.

In view of the amendments presented herewith, and the foregoing remarks, it is respectfully urged that the rejections set forth in the previously Official Actions be withdrawn and that this application be passed to issue.

In the event the Examiner is not persuaded as to the allowability of any claim, and it appears that any outstanding issues may be resolved through a telephone interview, the Examiner is requested to call the undersigned at the phone number given below.

The references below in Table 2 describe a number of different mutanases from a variety of biological sources. Each of these references incorporated herein by reference.

| Reference | Year | Mutanase resource |
|---|---|---|
| 1 Otsuka R, Imai S, Murata T, et al. (2014) Application of chimeric glucanase comprising mutanase and dextranase for prevention of dental biofilm formation. Microbiology and Immunology n/a-n/a | 2014 | *Paenibacillus humicus* NA1123 |
| 2 Wiater A, Pleszczynska M, Rogalski J, Szajnecka L & Szczodrak J (2013) Purification and properties of an alpha-(1 --> 3)-glucanase (EC 3.2.1.84) from Trichoderma harzianum and its use for reduction of artificial dental plaque accumulation. Acta Biochim Pol 60: 123-128. | 2013 | *Trichoderma harzianum* CCM F-340 |
| 3 Wiater A, Janczarek M, Choma A, Prochniak K, Komaniecka I & Szczodrak J (2013) Water-soluble (1 → 3), (1 → 4)-α-d-glucan from mango as a novel inducer of cariogenic biofilm-degrading enzyme. International Journal of Biological Macromolecules 58: 199-205. | 2013 | *Trichoderma harzianum* strain CCM F-340 |
| 4 Tsumori H, Shimamura A, Sakurai Y & Yamakami K (2012) Combination of Mutanase and Dextranase Effectively Suppressed Formation of Insoluble Glucan Biofilm by Cariogenic Streptococci. Interface Oral Health Science 2011, (Sasaki K, Suzuki O & Takahashi N, ed.ˆeds.), p.ˆpp. 215-217. Springer Japan. | 2012 | *Paenibacillus humicus* |
| 5 Xiao J, Klein MI, Falsetta ML, et al. (2012) The Exopolysaccharide Matrix Modulates the Interaction between 3D Architecture and Virulence of a Mixed-Species Oral Biofilm. PLoS Pathog 8: e1002623. | 2012 | *Trichoderma harzianum* |
| 6 Tsumori H, Shimamura A, Sakurai Y & Yamakami K (2011) Mutanase of <i>Paenibacillus humicus</i> from Fermented Food Has a Potential for Hydrolysis of Biofilms Synthesized by <i>Streptococcus mutans</i>. Journal of Health Science 57: 420-424. | 2011 | *Paenibacillus humicus* |
| 7 Wiater A, Szczodrak J & Pleszczynska M (2008) Mutanase induction in Trichoderma harzianum by cell wall of *Laetiporus sulphureus* and its application for mutan removal from oral biofilms. J Microbiol Biotechnol 18: 1335-1341. | 2008 | *Trichoderma harzianum* |
| 8 Shimotsuura I, Kigawa H, Ohdera M, Kuramitsu H K & Nakashima S (2008) Biochemical and Molecular Characterization of a Novel Type of Mutanase from *Paenibacillus* sp. Strain RM1: Identification of Its Mutan-Binding Domain, Essential for Degradation of *Streptococcus mutans* Biofilms. Applied and Environmental Microbiology 74: 2759-2765 | 2008 | *Paenibacillus* sp. strain RM1 |
| 9 Shimotsuura I, Kigawa H, Ohdera M, Kuramitsu H K & Nakashima S (2008) Biochemical and Molecular Characterization of a Novel Type of Mutanase from *Paenibacillus* sp. Strain RM1: Identification of Its Mutan-Binding Domain, Essential for Degradation of Streptococcus mutans Biofilms. Applied and Environmental Microbiology 74: 2759-2765. | 2008 | *Paenibacillus* sp. strain RM1 |
| 10 Wiater A, Szczodrak J; Pleszczyska M; Prochniak K(2005) Production and use of mutanase from *Trichoderma harzianum* for effective degradation of streptococcal mutans. Braz. J. Microbiol. vol. 36 no. 2 | 2005 | *Trichoderma harzianum* CCM F-340 |
| 11 Hayacibara M F, Koo H, Vacca Smith A M, Kopec L K, Scott-Anne K, Cury J A & Bowen W H (2004) The influence of mutanase and dextranase on the production and structure of glucans synthesized by streptococcal glucosyltransferases. Carbohydrate Research 339: 2127-2137 | 2004 | *Trichoderma harzianum* |

| Reference | Year | Mutanase resource |
|---|---|---|
| 12 Kopec LK, Vacca Smith A M, Wunder D, Ng-Evans L & Bowen W H (2001) Properties of *Streptococcus sanguinis* glucans formed under various conditions. Caries Res 35: 67-74. | 2001 | *Trichoderma harzianum* |
| 13 Kopec LK, Vacca-Smith A M & Bowen W H (1997) Structural aspects of glucans formed in solution and on the surface of hydroxyapatite. Glycobiology 7: 929-934. | 1997 | *Trichoderma harzianum* CCM F-341 |
| 14 Vacca-Smith A M, Venkitaraman A R, Quivey R G, Jr. & Bowen W H (1996) Interactions of streptococcal glucosyltransferases with alpha-amylase and starch on the surface of saliva-coated hydroxyapatite. Arch Oral Biol 41: 291-298. | 1996 | *Trichoderma harzianum* |
| 15 Quivey R G, Jr. & Kriger P S (1993) Raffinose-induced mutanase production from *Trichoderma harzianum*. FEMS Microbiol Lett 112: 307-312. | 1993 | *Trichoderma harzianum* |
| 16 Inoue M, Yakushiji T, Mizuno J, Yamamoto Y & Tanii S (1990) Inhibition of dental plaque formation by mouthwash containing an endo-alpha-1, 3 glucanase. Clin Prev Dent 12: 10-14. | 1990 | *Pseudomonas* sp. strain |
| 17 Inoue M, Yakushiji T, Katsuki M, Kudo N & Koga T (1988) Reduction of the adherence of Streptococcus sobrinus insoluble α-d-glucan by endo-(1→3)-α-d-glucanase. Carbohydrate Research 182: 277-286. | 1988 | *Pseudomonas* sp. |
| 18 Kelstrup J, Holm-Pedersen P & Poulsen S (1978) Reduction of the formation of dental plaque and gingivitis in humans by crude mutanase. European Journal of Oral Sciences 86: 93-102. | 1978 | *Trichoderma harzianum* |
| 19 Kelstrup J, Holm-Pedersen P & Poulsen S (1978) Reduction of the formation of dental plaque and gingivitis in humans by crude mutanase. Scand J Dent Res 86: 93-102. | 1978 | *Trichoderma harzianum* |
| 20 Guggenheim B, Regolati B & Mühlemann H R (1972) Caries and Plaque Inhibition by Mutanase in Rats. Caries Research 6: 289-297. | 1972 | *Trichoderma harzianum* OMZ 779 |

Additional biofilm degrading enzyme encoding sequences useful in the practice of the invention, include without limitation, I) *Paenibacillus humicus* NA1123

See also the world wide web at .ncbi.nlm.nih.gov/nuccore/AB489092

Genbank AB489092

Length:1,146

Mass (Da):119,007

Reference: Otsuka R, et al. Microbiol Immunol. 2015 January; 59(1):28-36.

2. The Protein Sequence of Mutanase from *Paenibacillus humicus* NA1123

```
>gi|257153265|dbj|BAI23187.1|putative mutanase
[Paenibacillus humicus]
                                           (SEQ ID NO: 12)
MRIRTKYMNWMLVLVLIAAGFFQAAGPIAPATAAGGANLTLGKTVTASGQ

SQTYSPDNVKDSNQGTYWESTNNAFPQWIQVDLGASTSIDQIVLKLPSGW

ETRTQTLSIQGSANGSTFTNIVGSAGYTFNPSVAGNSVTINFSAASARYV

RLNFTANTGWPAGQLSELEIYGATAPTPTPTPTPTPTPTPTPTPTVTP

APSATPTPTPPAGSNIAVGKSITASSSTQTYVAANANDNNTSTYWEGGSN

PSTLTLDFGSNQSITSVVLKLNPASEWGTRTQTIQVLGADQNAGSFSNLV

SAQSYTFNPATGNTVTIPVSATVKRLQLNITANSGAPAGQIAEFQVFGTP

APNPDLTITGMSWTPSSPVESGDITLNAVVKNIGTAAAGATTVNFYLNNE

LAGTAPVGALAAGASANVSINAGAKAAATYAVSAKVDESNAVIEQNEGNN

SYSNPTNLVVAPVSSSDLVAVTSWSPGTPSQGAAVAFTVALKNQGTLASA

GGAHPVTVVLKNAAGATLQTFTGTYTGSLAAGASANISVGSWTAASGTYT

VSTTVAADGNEIPAKQSNNTSSASLTVYSARGASMPYSRYDTEDAVLGGG

AVLRTAPTFDQSLIASEASGQKYAALPSNGSSLQWTVRQGQGGAGVTMRF

TMPDTSDGMGQNGSLDVYVNGTKAKTVSLTSYYSWQYFSGDMPADAPGGG

RPLFRFDEVHFKLDTALKPGDTIRVQKGGDSLEYGVDFIEIEPIPAAVAR

PANSVSVTEYGAVANDGKDDLAAFKAAVTAAVAAGKSLYIPEGTFHLSSM

WEIGSATSMIDNFTVTGAGIWYTNIQFTNPNASGGGISLRIKGKLDFSNI

YMNSNLRSRYGQNAVYKGFMDNFGTNSIIHDVWVEHFECGMWVGDYAHTP

AIYASGLVVENSRIRNNLADGINFSQGTSNSTVRNSSIRNNGDDGLAVWT

SNTNGAPAGVNNTFSYNTIENNWRAAAIAFFGGSGHKADHNYIIDCVGGS

GIRMNTVFPGYHFQNNTGITFSDTTIINSGTSQDLYNGERGAIDLEASND

AIKNVTFTNIDIINAQRDGVQIGYGGGFENIVFNNITIDGTGRDGISTSR

FSGPHLGAAIYTYTGNGSATFNNLVTRNIAYAGGNYIQSGFNLTIK
```

3. Sequence of mRNA from *Paenibacillus humicus* NA1123

```
>gi|257153264|dbj|AB489092.1|Paenibacillus humicus
mut gene for putative mutanase, complete cds
                                           (SEQ ID NO: 13)
  1 aaaggaggat cgccaaccaa tcatcccagc aaagaaggtg atggcagccc aagaattgaa 61 agcgctttga atttggaata tacggatttg gccgacctgc tgattcagtc gtattcaagc 121 gattatgccg cgaaccaatc gaacccgagg aggactataa tgcgtatccg cactaaatat 181 atgaactgga tgttggtgct cgtcctgatc gccgccggct tcttccaggc tgccggcccc 241 atcgctcccg ccaccgctgc aggaggcgcg aatctgacgc tcggcaaaac cgtcaccgcc 301 agcggccagt cgcagacgta cagccccgac aatgtcaagg acagcaatca gggaacttac
```

-continued

```
 361 tgggaaagca cgaacaacgc cttcccgcag tggatccaag tcgaccttgg cgccagcacg 421 agcatcgacc agatcgtgct caagcttccg tccggatggg agactcgtac gcaaacgctc 481 tcgatacagg gcagcgcgaa cggctcgacg ttcacgaaca tcgtcggatc ggccgggtat 541 acattcaatc catccgtcgc cggcaacagc gtcacgatca acttcagcgc tgccagcgcc 601 cgctacgtcc gcctgaattt cacggccaat acgggctggc cagcaggcca gctgtcggag 661 cttgagatct acggagcgac ggcgccaacg cctactccca cgcctactcc aacaccaacg 721 ccaacgccaa caccaacgcc aaccccctaca gtaacccctg cgccttcggc cacgccgact 781 ccgactcctc cggcaggcag caacatcgcc gtagggaaat cgattacagc ctcttccagc 841 acgcagacct acgtagctgc aaatgcaaat gacaacaata catccaccta ttgggaggga 901 ggaagcaacc cgagcacgct gactctcgat ttcggttcca accagagcat cacttccgtc 961 gtcctcaagc tgaatccggc ttcggaatgg gggactcgca cgcaaacgat ccaagttctt 1021 ggagcggatc agaacgccgg ctccttcagc aatctcgtct ctgcccagtc ctatacgttc 1081 aatcccgcaa ccggcaatac ggtgacgatt ccggtctccg cgacggtcaa cgcctccag 1141 ctgaacatta cggcgaactc cggcgcccct gccggccaga ttgccgagtt ccaagtgttc 1201 ggcacgccag cgcctaatcc ggacttgacc attaccggca tgtcctggac tccgtcttct 1261 ccggtcgaga gcggcgacat tacgctgaac gccgtcgtca agaacatcgg aactgcagct 1321 gcaggcgcca cgacggtcaa tttctacctg aacaacgaac tcgccggcac cgctccggta 1381 ggcgcgcttg cggcaggagc ttctgcaaat gtatcgatca atgcaggcgc caaagcagcc 1441 gcaacgtatg cggtaagcgc caaagtcgac gagagcaacg ccgtcatcga gcagaatgaa 1501 ggcaacaaca gctactcgaa cccgactaac ctcgtcgtag cgccggtgtc cagctccgac 1561 ctcgtcgccg tgacgtcatg gtcgccgggc acgccgtcgc agggagcggc ggtcgcattt 1621 accgtcgcgc ttaaaaatca gggtacgctg gcttccgccg gcggagccca tcccgtaacc 1681 gtcgttctga aaaacgctgc cggagcgacg ctgcaaacct tcacgggcac ctacacaggt 1741 tccctggcag caggcgcatc cgcgaatatc agcgtgggca gctggacggc agcgagcggc 1801 acctataccg tctcgacgac ggtagccgct gacggcaatg aaattccggc caagcaaagc 1861 aacaatacga gcagcgcgag cctcacggtc tactcggcgc gcggcgccag catgccgtac 1921 agccgttacg acacggagga tgcggtgctc ggcggcggag ctgtcctgag aacggcgccg 1981 acgttcgatc agtcgctcat cgcttccgaa gcatcggac agaaatacgc cgcacttccg 2041 tccaacggct ccagcctgca gtggaccgtc cgtcaaggcc agggcggtgc aggcgtcacg 2101 atgcgcttca cgatgcccga cacgagcgac ggcatgggcc agaacggctc gctcgacgtc 2161 tatgtcaacg gaaccaaagc caaaacggtg tcgctgacct cttattacag ctggcagtat 2221 ttctccggcg acatgccggc tgacgctccg ggcggcggca ggccgctctt ccgcttcgac 2281 gaagtccact tcaagctgga tacggcgttg aagccgggag acacgatccg cgtccagaag 2341 ggcggtgaca gcctggagta cggcgtcgac ttcatcgaga tcgagccgat tcggcagcg 2401 gttgcccgtc cggccaactc ggtgtccgtc accgaatacg cgcgctgtcgc caatgacggc 2461 aaggatgatc tcgccgcctt caaggctgcc gtgaccgcag cggtagcggc cggaaaatcc 2521 ctctacatcc cggaaggcac cttccacctg agcagcatgt gggagatcgg ctcggccacc 2581 agcatgatcg acaacttcac ggtcacgggt gccggcatct ggtatacgaa catccagttc 2641 acgaatccca atgcatcggg cggcggcatc tccctgagaa tcaaaggaaa gcttgatttc 2701 agcaacatct acatgaactc caacctgcgt tcccgttacg ggcagaacgc cgtctacaaa 2761 ggctttatgg acaatttcgg cactaattcg atcatccatg acgtctgggt cgagcatttc
```

```
2821 gaatgcggca tgtgggtcgg cgactacgcc catactcctg cgatctatgc gagcgggctc 2881 gtcgtggaaa acagccgcat ccgcaacaat cttgccgacg gcatcaactt ctcgcaggga 2941 acgagcaact cgaccgtccg caacagcagc atccgcaaca acggcgatga cggcctcgcc 3001 gtctggacga gcaacacgaa cggcgctccg gccggcgtga acaacacctt ctcctacaac 3061 acgatcgaga caactggcg cgcggcggcc atcgccttct tcggcggcag cggccacaag 3121 gctgaccaca actacatcat cgactgtgtc ggcggctccg gcatccggat gaatacggtg 3181 ttcccaggct accacttcca gaacaacacc ggcatcacct tctcggatac gacgatcatc 3241 aacagcggca ccagccagga tctgtacaac ggcgagcgcg gagcgattga tctggaagct 3301 tccaacgacg cgatcaaaaa cgtcaccttc accaacatcg acatcatcaa tgcccagcgc 3361 gacggcgttc agatcggcta tggcggcggc ttcgagaaca tcgtgttcaa caacatcacg 3421 atcgacggca ccggccgcga cgggatatcg acatcccgct tctcgggacc tcatcttggc 3481 gcagccatct atacgtacac gggcaacggc tcggcgacgt tcaacaacct ggtgacccgg 3541 aacatcgcct atgcaggcgg caactacatc cagagcgggt tcaacctgac gatcaaatag 3601 gctgcaaaaa aaaggaagct cctcggagct tccttttttt
```

II) *Paenibacillus curdlanolyticus* MP-1
1. General Information of of Mutanase from *Paenibacillus curdlanolyticus* MP-1
 See the world wide web at .ncbi.nlm.nih.gov/nuccore/HQ640944
Genbank HQ640944; Length:1,261; Mass (Da): 131,631
Reference: Pleszczyilska M, et al. Protein Expr Purif. 2012 November; 86(1):68-74.
2. The Protein Sequence of Mutanase from *Paenibacillus curdlanolyticus* MP-1

```
>gi|315201261|gb|ADT91063.1|alpha-1,3-glucanase
[Paenibacillus curdlanolyticus]
                                        (SEQ ID NO: 14)
MRNKYVTWTLALTMLFSSFFLAVGPNKVVHAAGGTNLALGKNVTASGQSQ

TYSPNNVKDSNQSTYWESTNNAFPQWIQVDLGATTSIDQIVLKLPAGWGT

RTQTLAVQGSTDGSSFTNIVGSAGYVFNPAVANNAVTINFSAASTRYVRL

NVTANTAWPAAQLSEFEIYGAGGTTTPPTTPAGTYEAESAALSGGAKVNT

DHTGYTGTGFVDGYWTQGATTTFTANVSAAGNYDVTLKYANASGSAKTLS

VYVNGTKIRQTTLASLANWDTWGTKVETLSLNAGNNTIAYKYEASDSGNV

NIDSIAVAPSTSTPVDPEPPITPPTGSNIAIGKAISASSNTQAFVAANAN

DNDTNTYWEGGAASSTLTLDLGANQNVTSIVLKLNPSSAWSTRTQTIQVL

GHNQSTTTFSNLVSSQSYTFNPATGNSVTIPVTATVKRLQLSITANSGSG

AGQIAEFQVYGTPAPNPDLTITGMSWTPASPIETDAVTLNATVKNSGNAD

APATTVNFYLNNELVGSSPVGALAAGASSTVSLNVGTKTAATYAVSAKVD

ESNSIIEQNDANNSYTNASSLVVAPVASSDLVGATTWTPSTPVAGNAIGF

MVNLKNQGTIASASGAHGITVVVKNAAGAALQSFSGTYSGAIAAGASVNV

TLPGTWTAVNGSYTVTTTVAVDANELTNKQGNNVSTSNLVVYAQRGASMP

YSRYDTEDATRGGGATLQTAPTFNQAQIASEASGQSYIALPSNGSSAQWT

VRQGQGGAGVTMRFTMPDSTDGMGLNGSLDVYVNGVKVKTVSLTSYYSWQ

YFSGDMPGDAPSAGRPLFRFDEVHWKLDTPLQPGDTIKIQKGNGDSLEYG

IDFLEIEPVPTAIAKPANSLSVTEYGAVANDGQDDLAAFKATVTAAVAAG

KSVYIPAGTFNLSSMWEIGSANNMINNITITGAGYWHTNIQFTNPNAAGG

GISLRISGQLDFSNVYMNSNLRSRYGQNAIYKGFMDNFGTNSKIHDVWVE

HFECGMWVGDYAHTPAIYATGLVVENSRIRNNLADGINYSQGTSNSIVRN

SSIRNNGDDGLAVWTSNTNGAPAGVNNTFSYNTIENNWRAGGIAFFGGGG

HKADHNLIVDTVGGSGIRMNTVFPGYHFQNNTGITFSDNTLINTGTSQDL

YNGERGAIDLEASNDAIKNVTFTNIDIINTQRDAIQFGYGGGFENIVFNN

ININGTLDGVTTSRFAGPHKGAAIYTYTGNGSATFNNLTTSNVAYPGLN

FIQQGFNLVIQ
```

3. Sequence of mRNA from *Paenibacillus curdlanolyticus* MP-1

```
                                        (SEQ ID NO: 15)
  1 atgcgcaaca agtatgtcac atggacgctc gccctgacga tgctatttc gagcttcttc 61 cttgcagtag gtcccaacaa ggtcgttcac gcagcaggcg gaacgaattt agcgctcggc 121 aaaaacgtta cggcaagcgg ccaatcgcaa acgtatagtc ccaacaatgt aaaagacagc 181 aatcaatcga cgtactggga aagcacgaac aatgcattcc cgcaatggat tcaagtagac 241 ttaggcgcaa cgacgagcat tgaccaaatc gtactgaagc tgcccgctgg atggggtacg
```

-continued

```
 301 cgtacgcaaa cgttagctgt tcaaggaagc acggacggtt cctcgttcac gaatatcgtg
 361 ggctccgcag gctatgtatt taatcctgct gttgccaata acgccgttac gattaacttc
 421 tctgctgcaa gcacgcgtta tgttcgtctg aacgtaacag cgaacacggc ttggccagca
 481 gcgcagctgt ccgaattcga gatttatggc gctggcggca cgacgacgcc tccaacaacg
 541 ccagcaggca catatgaagc tgaatccgca gcattgtccg gcggtgcgaa agtgaacacg
 601 gatcataccg gctacacggg tacgggcttt gttgacggct actggacaca aggcgcgaca
 661 acgacgttca cggctaacgt gtccgcagct ggcaactatg acgttacatt gaaatatgcc
 721 aacgcaagcg gcagtgccaa gacgctaagc gtttacgtca acggcacgaa gattcgccag
 781 acgacgctgg caagcctggc aaactgggac acttggggca cgaaggttga gacgctgagc
 841 ttgaatgccg gcaataatac gattgcatac aagtatgagg ctagcgactc gggcaacgtg
 901 aatatcgact ccattgccgt ggcgccatcg acttcgacac cggtagatcc agaaccgccg
 961 atcacgccgc caacgggcag caatatcgca atcggcaaag cgatcagcgc atcttcgaat
1021 acgcaagcat tcgtagctgc caacgcgaac gataacgata cgaacacgta ctgggaaggc
1081 ggagctgcat cgagcacgct gacgctggat cttggcgcga accaaaatgt aacctcgatc
1141 gtgctgaagc tgaatccttc ttcggcatgg agcacgcgta cgcaaacgat ccaagtgctt
1201 ggccacaacc aaagcacgac gacgttcagc aatctggtat cttcgcaatc gtatacgttc
1261 aatcctgcaa cgggcaactc cgtgacgatt ccggttacgg caacagttaa gcgcttgcag
1321 ctgagcatta cggcgaactc gggttccggc gctggtcaaa ttgcggaatt ccaagtgtat
1381 ggaacgccgg caccaaaccc agacctgacg atcacaggca tgtcctggac gcctgcttcg
1441 ccaattgaaa cggatgcagt tacgctgaat gcaacggtta aaaacagcgg aaatgcagac
1501 gctcctgcaa cgacggtaaa cttctacctg aacaatgagc tcgtaggctc ctcgccagtt
1561 ggcgcacttg ctgcaggcgc ttcctcgacg gtttcgctga atgttggtac gaaaacggct
1621 gcaacttatg cagttagcgc gaaagtcgat gagagcaatt cgattatcga gcaaaatgat
1681 gcgaacaaca gttatacgaa cgcatcctcg ctcgtcgtcg ctcctgtcgc aagctctgac
1741 ttggttggcg cgacgacgtg gacgcctagc acgccggttg ccggcaatgc aattggcttc
1801 atggtaaatc ttaaaaacca aggaacgatt gcatctgcaa gcggcgcgca tggcattaca
1861 gttgtcgtga aaaatgccgc aggcgctgcg ctccaatcgt tcagcggcac ctacagcgga
1921 gcaatcgcag ctggcgcatc cgttaacgta accctgccag gtacgtggac ggctgtgaat
1981 ggcagctaca cggtaacgac aacggttgct gtcgatgcta acgagctgac gaacaaacaa
2041 gggaacaacg taagcacttc gaacctcgtt gtttatgcac aacgtggcgc aagcatgcct
2101 tacagccgtt atgacacgga agacgctaca cgtggcggcg gtgcaacgct gcaaaccgca
2161 ccaaccttca accaagcgca aatcgcttcg gaagcatccg gacaaagcta tatcgcgctg
2221 ccttcgaacg gctcctccgc acaatggacg gtccgtcaag gacaaggcgg agctggcgtt
2281 acgatgcgct tcacgatgcc ggattcgact gacggtatgg gtttgaacgg ttcgctcgac
2341 gtttatgtca acggcgttaa agtaaaaacg gtatcgctca cgtcctacta cagctggcag
2401 tatttctcgg gcgatatgcc tggcgatgcg ccgtccgctg gccgtccgtt gttccgcttt
2461 gacgaagtac actggaagct tgacacgcct cttcaaccag gcgacacgat caaaatccaa
2521 aaaggcaacg gagatagcct ggaatacggc attgacttcc tcgaaatcga gccggttcca
2581 acagcaatcg ctaaacctgc caactcgctt tccgttacgg agtatggcgc tgtagcaaac
2641 gatggccaag acgaccttgc cgcattcaaa gcaacggtta cggctgcagt tgctgctggc
2701 aaatccgttt acattcctgc tggcacgttc aatctgagca gcatgtggga aatcggatcg
```

-continued

```
2761 gctaacaaca tgatcaacaa cattacgatt acaggcgcag gctactggca tacgaacatt
2821 caattcacga atccgaatgc agcaggcggc ggcatttcgc tccggatttc cggacagctt
2881 gatttcagca atgtttacat gaactccaac ctgcgttcgc gttatggtca aaatgcgatt
2941 tacaaaggct tcatggacaa cttcggcaca aactccaaaa tccatgacgt atgggttgag
3001 cacttcgagt gcggcatgtg ggtaggcgat tacgcgcata cgccagcgat ctatgcaacg
3061 ggtcttgtcg ttgaaaacag ccggattcgc aacaaccttg cagacggcat caactactcg
3121 caaggcacga gcaattcgat cgtacgcaac agcagtatcc gcaataacgg tgatgacggt
3181 ctggcggttt ggacgagtaa cacgaatggc gcgccagcag gcgtgaacaa cacgttctcg
3241 tacaacacga tcgaaaacaa ctggcgtgca ggcggtatcg cattcttcgg cggcggcggc
3301 cacaaggctg accacaacct gatcgttgat acggttggcg gctccggcat ccggatgaac
3361 acggtattcc caggctacca cttccaaaac aacacgggta ttacgttctc cgacaacacg
3421 ctgatcaaca caggcacaag ccaagatttg tacaacggcg agcgcggtgc gatcgatctc
3481 gaagcatcga acgatgcaat caagaacgtc acgttcacga acatcgacat catcaacacc
3541 cagcgcgatg cgatacaatt cggctacggc ggcggattcg agaacatcgt atttaacaac
3601 attaacatta acggtacggg gcttgacggc gttacaacct cacggtttgc tggaccgcat
3661 aaaggtgctg caatctacac gtacacgggc aatggctctg caacgttcaa taacctgacg
3721 acgagcaacg tggcatatcc aggcttgaat ttcattcagc aaggctttaa tctggtgatc
3781 cagtag
```

III) *Paenibacillus* sp. strain RM1.
1. General Information of Mutanase
Genbank E16590; Length: 1,291; Mass (Da): 135 kD Reference: Shimotsuura I, et al. Appl Environ Microbiol. 2008 May; 74(9):2759-65.2. The protein sequence of mutanase from *Paenibacillus* sp. strain RM1

```
              ↓
  1 MRCKFVAWSL VTAMLMASLL TAVGPFGPAS AAGGPNLTPG KPITASGQSQ
 51 TYSPQNVKDG NQNTYWESTN NAFPQWIQVD LGASTGIDQI VLKLPASWEA
101 RTQTLAVQGS LNGSTFTDIV GSANYVFSPS VGNNTVTINF TATSTRYVRL
151 YVTANTGWPA AQLSEFEIYG SGDQTPAPDT YQAESAALSG GAKVNTDHAG
201 YIGTGFVDGY WTQGATTTFS VNAPTAGNYD VRLRYGNATG SNKTVSLYVN
251 GAKTRQTTLP SLPNWDSWSS KTETLNLNAG SNTIAYKYDP GDSGNVNLDQ
301 ITVEASTS TP TPTPSPTPTP TPTPTPTPTP TPTPTPTPTP TPTPTPTPTP
351 TPPH GGNIAI GKSISASSHT QTYVAENAND NDVNTYWEGG GNPSTLTLDL
401 GANYNITSIV LKLNPSSIWA ARTQTIQVLG HDQNTTTFSN LVSAKSYSFD
451 PASGNTVTIP VTATVKRLQL NITSNSGAPA GQVAEFQVFG TPAPNPDLTI
501 TGMSWSPSSP VETDAITLNA TVKNNGNASA AATTVNFYLN NELAGSAPVA
551 ALAAGASATV PLNVGAKTAA TYAVGAKVDE SNAVIELNES NNSYTNPASL
601 VVAPVSSSDL VGTVSWTPST PIANNAVSFN VNLKNQGTIA SAGGSHGVTV
651 VLKNASGSTV QTFSGSYTGS LAPGASVNIT LPGTWTAAAG SYTVTATVAA
701 DANELPIKQA NNANTASLTV YSARGASMPY SRYDTEDATL GGGATLKSAP
751 TFDQALTASE ATGQLYAALP SNGSYLQWTV RQGQGGAGVT MRFTMPDSAD
801 GMGLNGSLDV YVNGTKVKTV SLTSYYSWQY FSGDMPGDAP SAGRPLFRFD
851 EVHWKLDTPL KPGDTIRIQK NNGDSLEYGV DFIEIEPVPA AISRPANSVS
```

```
 901 VTDYGAVPND GQDDLTAFKA AVNAAVASDK ILYIPEGTFH LGNMWEIGSV
 951 SNMIDHITIT GAGTWYTNIQ FTNANPASGG ISLRITGKLD FSNVYLNSNL
1001 RSRYGQNAVY KGFMDNFGTN SVIRDVWVEH FECGFWVGDY GHTPAIRASG
1051 LLIENSRIRN NLADGVNFAQ GTSNSTVRNS SLRNNGDDAL AVWTSNTNGA
1101 PEGVNNTFSY NTIENNWRAG GIAFFGGSGH KADHNYIVDC VGGSGIRMNT
1151 VFPGYHFQNN TGIVPSDTTI VNCGTSKDLY NGERGAIDLE AGNDAIRNVT
1201 FTNIDIINSQ RDAIQFGYGG GFTNIVFNNI NINGTGLDGV TTSRFSGPHL
1251 GAAIFTYTGN GSATFNNLRT SNIAYPNLYY IQSGPNLIIN N
```

15

Deduced amino acid sequence of mutanase RM1. The signal peptide region is underlined, and the linker region is boxed. The arrow indicates the cleavage site for the N-terminal domain of the protein. The DNA sequence was registered as GenBank accession number E16590. (SEQ ID NO: 16)

3. Sequence of mRNA from *Paenibacillus* sp. Strain RM1

(SEQ ID NO: 17)

```
   1 cccgggtacc agacctatcg ggaaaaacgc gagcggccct tcgcgcctta tgcgctacgg
  61 acggtgctgg cgggcggttt gtttttcatc atcattcccc tgatgatcta cacggcatcg
 121 tatatcccgt ttttgctcgt gccgggtccc ggacacgggt tgaaagacgt cgtctccgcc
 181 cagaagttca tgttcaatta tcatagccgg cttaacgcca cccacccatt ctcgtcgctg
 241 tggtgggagt ggcctctcat ccgcaagccg atctggtatt acggagccgc ggaattggcg
 301 ccgggaaaaa tggcgagcat cgtgggcatg ggcaatccgg cggtgtggtg gacgggaacg
 361 attgcggtaa tcgcggccct tcgctcggcc tggaagaagc gggaccggag catgaccgtc
 421 gtcttcgttg gaatcgcctc gtcttatctt ccgtgggttt tcgtatccag actcaccttt
 481 atttatcact ttttcgcttg cgttccgttt ctcgttcttt gcatcgttta ttggattcga
 541 aaaatggaat agcgtaagcc gggatatcgg attgcgacgc tcctttacgc aggcgcggtt
 601 ctggtgctgt tcattttgtt ttacccgatt ttgtcgggga ccgaaataga cgtttcttac
 661 gcggaccgcg ttctgaagtg gttcggcggg tggattttc acgggtaagc gagcgttgga
 721 agcaaggaag ggaaggaaga cgagcgtctc cttcccgaaa tccatccaat atcttgaaat
 781 tgcatacatt tttcgtaaga ttgcttctta tctgtctccc tcccctgttc ttataatggg
 841 ggtatcccaa cgaaaggagg gtttgtaagc gctgtcagcs tgtttgccga aagttctcgc
 901 atttgctgac ctacactttg aggaggagga atttaatgcg ctgcaaattt gtcgcatggt
 961 cgcttgttac agccatgctg atggccagtt tgctgacggc tgtaggaccg ttcgccccg
1021 cttccgccgc gggaggaccg aatctgacgc cgggcaaacc cattacggcg agcggccaat
1081 cccaaaccta cagccctcag aacgtaaaag acggcaatca aaatacgtat tgggaaagca
1141 cgaacaacgc gttcccgcaa tggattcaag tggatttggg cgcaagcacg ggcatcgacc
1201 aaattgtgct gaagctgccc gcaagctggg aagcgcgcac gcaaacgctg gccgttcaag
1261 gcagcttgaa cggttcgacg ttcacggaca ttgtcggctc cgccaattat gtattcagtc
1321 cgtctgtcgg gaacaacacg gttacgatca actttaccgc gaccagcacg cgctacgtgc
1381 gcttgtatgt aacggccaac acgggctggc cggcggcgca gctgtccgaa ttcgaaattt
1441 acggctccgg cgaccagacg ccggcgcctg atacgtatca agccgaatcc gcggctctgt
1501 ccggcggcgc gaaagtcaac acggaccatg ccggatatat cggcacgggc tttgttgacg
1561 gttactggac gcaaggcgcg acgacgacct tttcggtcaa cgcgccgacg gcgggcaact
1621 acgatgtaac gctgaggtac ggcaacgcaa ccggcagcaa caaaacggta agcctctacg
```

-continued

```
1681 tcaatggagc gaagattcgc cagaccacgc tgcccagcct gcctaactgg gattcatgga 1741 gcagcaagac ggagacgctt aacctgaatg caggcagcaa caccattgcg tacaaatacg 1801 acccgggcga ttccggcaac gtcaatcttg accaaatcac ggtcgaagcg tcgacttcaa 1861 cgcctactcc tactccatcc cctactccta cacctacgcc aacgccgacg cctacgccta 1921 cgcctacacc cacacctact ccgaccccga cgcctacgcc tacacctaca cctacaccta 1981 cgccgacgcc tcctccgggc ggcaacatcc ccatcggcaa atcgatttcc gcatcctccc 2041 acacgcagac gtacgttgcg gagaacgcga acgataacga tgtcaacacg tactgggaag 2101 gcggcggcaa tccgagcacg ctgacgctcg atctcggagc gaactacaat attacgtcca 2161 tcgtgctgaa gctgaacccg tcctcgatat gggctgcgcg tacgcaaacg attcaagtgc 2221 tcggacacga tcagaacacg acgaccttca gcaatctggt ctcggcgaaa tcgtactcgt 2281 tcgatccggc ctccggcaat actgtgacca ttccggttac ggcgacggtg aaacgtttgc 2341 agttgaacat tacgtcgaac tccggcgccc cggccggaca agtcgccgag ttccaggtgt 2401 tcggcacgcc tgcgccgaat ccggacctga cgattaccgg catgtcctgg tcgccttctt 2461 ctccggttga gaccgacgcc attacgctaa acgcaacggt gaagaacaac gggaatgcca 2521 gcgccgcggc gaccaccgtc aatttctacc tgaacaacga gctggcgggt tccgcgccgg 2581 tagccgcgct ggcggcaggc gcttcggcaa cggtgccgct gaatgtcggc gcgaaaaccg 2641 ccgcgacata cgcggtcggc gccaaagtag acgagagcaa cgcggtcatc gagctgaacg 2701 agtcgaacaa cagctacacg aatccggctt cactcgttgt ggcccccgtt ccagctcgg 2761 atctggtggg cacggtttcg tggacgccga gcactccgat tgccaacaat gccgtttctt 2821 ttaacgtaaa tcttaaaaat caaggaacga ttgcttccgc cggcgggtct cacggcgtga 2881 cggtcgtgct taaaaatgct tccggttcga ccgttcaaac gttcagcggt tcctataccg 2941 gcagcctggc tccgggagcg tccgtcaaca tcacccttcc ggggacctgg acggcggcag 3001 ccggcagcta cacggtaacg gccaccgttg cggcagacgc caacgaactt ccgatcaagc 3061 aagccaacaa cgcgaacacc gcaagcctga ccgtatattc cgcccgcggc gcgagcatgc 3121 cgtacagccg gtatgacacc gaggacgcca ccctcggcgg cggcgccacg ctgaagtccg 3181 cgccgacatt cgatcaggcg cttacggcat cggaagccac cggccaactc tatgcggcgc 3241 tgccctcgaa cggctcctat cttcaatgga ccgtcagaca gggtcagggc ggcgcaggcg 3301 tgacgatgag atttacgatg cccgactcgg cggacggcat gggattaaac ggttcgctag 3361 acgtttacgt caacggcacc aaagtcaaaa ccgtatcgct gacctcctac tacagctggc 3421 agtatttctc gggcgatatg cccggagacg ctcccagcgc gggccgtccg ctcttccgct 3481 ttgacgaagt gcactggaag ctggatactc cgctcaaacc cggagacacg attcgcatcc 3541 agaagaacaa cggcgacagc ctggaatacg gtgtcgactt tattgaaatc gaaccggttc 3601 cggctgcgat ctcccgtccg gccaactcgg tttccgtaac ggattacggc gctgtgccga 3661 acgacggaca ggacgatctc accgcccttta aagccgccgt aaacgcggcg gtcgcatccg 3721 acaagatctt gtacattccg gaaggaacgt tccacctcgg caacatgtgg gagatcggtt 3781 ccgtcagcaa catgatcgat cacattacga ttacgggagc cggtatctgg tatacgaaca 3841 tccagtttac caacgccaat ccggcgtccg gcggcatctc gctccggatt acgggcaagc 3901 ttgatttcag caacgtgtac ctcaactcca atttgcggtc gcggtatggt caaaatgcgg 3961 tttacaaagg ctttatggac aacttcggga ccaattccgt catccgcgac gtctgggtcg 4021 agcacttcga atgcggcttc tgggtcgggg actacgggca tacgccggcg atccgcgcga 4081 gcgggctgct gattgaaaac agccgaatcc gcaacaacct ggccgatggc gtcaacttcg
```

-continued

```
4141 cccaagggac cagcaattcg accgtacgca acagcagcct gcgcaacaac ggcgacgacg 4201 cccttgccgt atggacgagt aatacgaacg gcgcgcccga aggcgtaaac aataccttct 4261 cgtacaacac catcgaaaac aactggcgcg cgggaggcat cgccttcttc ggaggaagcg 4321 gacacaaggc cgaccacaac tacatcgtcg actgcgtcgg cggttccggc atccggatga 4381 acaccgtgtt ccccggatac cacttccaga acaataccgg cattgtgttc tcggacacga 4441 ccatcgtcaa ctgcggcacg agcaaagacc tatacaacgg cgaacgcggc gccatcgatc 4501 tggaagcttc gaacgacgcc atccggaacg tgacgtttac caacatcgat attatcaact 4561 ctcagcgcga tgcgatccag ttcggttacg gcggcggctt caccaacatc gtgttcaaca 4621 acatcaacat taacggaacc ggtcttgacg gcgtaaccac ctcgcggttc tcgggaccgc 4681 atctgggcgc ggcgatcttc acctataccg gcaacggctc cgccacgttc aacaatctga 4741 ggaccagcaa tatcgcttac cccaatctgt attacatcca gagcgggttc aatctgatca 4801 tcaataatta gatatctggg cccgtctgcg ggggaggaac tcttcggagc tcgaattcgt 4861 aatcatggtc atagctgttt cctgtgtgaa attgttatcc gctcacaatt ccacacaaca 4921 tacgagccgg aagcataaag tgtaaagcct ggggtgccta atgagtgagc taactcacat 4981 taattgcgtt gcgctcactg cccgctttcc agtcgggaaa ctgtcgtgcc agctgcatta 5041 atgaatcggc caacgcgcgg ggagaggcsg tttkcgtatt gggcgccctt
```

IV) *Trichoderma harzianum* (CCM F-470)
1. General Information of of Mutanase from *Trichoderma harzianum*
  Also see the world wide web at .uniprot.org/uniprot/Q8WZM7Length:635
Mass (Da):67,726
Last modified:Mar. 1, 2002-v1
Checksum:iBBOD864E2F432C58
2. The Protein Sequence of Mutanase from *Trichoderma harzianum*
  See the world wide web at .uniprot.org/uniprot/Q8WZM7.fasta

```
>tr|Q8WZM7|Q8WZM7_TRIHA Alpha-1,3-glucanase
OS = Trichoderma harzianum GN = p3 PE = 2 SV = 1
                                          (SEQ ID NO: 18)
MLGVFRRLRLGALAAAALSSLGSAAPANVAIRSLEERASSADRLVFCHFM
IGIVGDRGSSADYDDDMQRAKAAGIDAFALNIGVDGYTDQQLGYAYDSAD
RNGMKVFISFDFNWWSPGNAVGVGQKIAQYANRPAQLYVDNRPFASSFAG
DGLDVNALRSAAGSNVYFVPNFHPGQSSPSNIDGALNWMAWDNDGNNKAP
KPGQTVTVADGDNAYKNWLGGKPYLAPVSTWVFNHFGPEVSYSKNWVFPS
GPLIYNRWQQVLQQGFPRVEIVTWNDYGESHYVGPLKSKQFHDGNSKWVN
DMPHDGFLDLSKPFIAAYKNRDTDISKYVQNEQLVYWYRRNLKALDCDAT
DTTSNRPANNGSGNYFEGRPDGWQTMDDTVYVAALLKTAGSVTVTSGGTT
QTFQANAGANLFQIPASIGQQKFALTRNGQTVFSGTSLMDITNVCSCGIY
NFNPYVGTIPAGFDDPLQADGLFSLTIGLHVTTCQAKPSLGTNPPVTSGP
VSSLPASSTTRASSPPPVSSTRVSSPPVSSPPVSRTSSAPPPPGNSTPPS
GQVCVAGTVADGESGNYIGLCQFSCNYGYCPPGPCKCTAFGAPISPPASN
GRNGCPLPGEGDGYLGLCSFSCNHNYCPPTACQYC
```

3. Sequence of mRNA (*Trichoderma harzianum*)
  See the world wide web at .ebi.ac.uk/ena/data/view/AJ243799&display=fasta

```
>ENA|AJ243799|AJ243799.1 Trichoderma harzianum
mRNA for alpha-1,3-glucanase (p3 gene)
                                          (SEQ ID NO: 19)
ATGTTGGGCGTTTTCCGCCGCCTCAGGCTCGGCGCCCTTGCCGCCGCAGC
TCTGTCTTCTCTCGGCAGTGCCGCTCCCGCCAATGTTGCTATTCGGTCTC
TCGAGGAACGTGCTTCTTCTGCTGACCGTCTCGTATTCTGTCATTTCATG
ATTGGGATCGTGGGTGACCGTGGCAGCTCGGCAGATTATGATGACGATAT
GCAACGTGCCAAAGCCGCTGGCATTGACGCCTTCGCCCTGAACATCGGCG
TTGACGGCTATACCGACCAGCAGCTCGGCTATGCCTATGACTCTGCCGAT
CGTAATGGCATGAAAGTCTTCATTTCATTTGATTTCAACTGGTGGAGCCC
CGGCAATGCAGTTGGTGTTGGCCAGAAGATTGCGCAGTATGCCAACCGCC
CTGCCCAGCTGTATGTCGACAACCGGCCATTCGCCTCTTCCTTCGCCGGT
GACGGTCTGGATGTAAATGCGTTGCGCTCTGCTGCAGGCTCCAACGTTTA
CTTTGTGCCCAACTTCCACCCTGGTCAATCTTCCCCCTCCAACATTGATG
GCGCCCTTAACTGGATGGCCTGGGATAATGATGGAAACAACAAGGCACCC
AAGCCGGGCCAGACTGTCACAGTGGCAGACGGTGACAACGCTTATAAGAA
TTGGTTGGGTGGCAAGCCTTACCTGGCGCCTGTCTCAACTTGGGTTTTCA
ACCATTTCGGGCCCGAAGTTTCATATTCCAAGAACTGGGTTTTCCCAAGT
GGGCCTCTGATCTATAACCGGTGGCAACAAGTCTTGCAGCAAGGGTTCCC
AAGGGTTGAGATCGTTACCTGGAATGACTACGGGGAATCTCACTACGTCG
GTCCCCTGAAGTCTAAGCAATTTCATGATGGGAACTCCAAATGGGTCAAT
GATATGCCCCACGATGGATTCCTGGATCTTTCGAAGCCGTTCATAGCCGC
```

-continued
```
ATATAAAAACAGGGATACCGACATCTCCAAGTATGTTCAAAATGAGCAGC

TTGTTTACTGGTACCGCCGCAACTTAAAGGCACTGGACTGTGACGCCACC

GACACAACCTCTAACCGCCCGGCTAACAATGGAAGCGGCAATTACTTTGA

GGGACGCCCCGATGGTTGGCAAACTATGGATGATACGGTTTACGTGGCGG

CACTTCTCAAGACTGCCGGTAGCGTCACGGTCACGTCTGGTGGCACCACT

CAAACGTTCCAGGCCAACGCCGGAGCCAATCTCTTCCAAATCCCGGCCAG

CATCGGCCAGCAAAGTTTGCTCTGACTCGTAACGGTCAGACCGTCTTTA

GCGGAACCTCATTGATGGATATCACCAACGTTTGCTCTTGCGGTATCTAC

AACTTCAACCCATATGTTGGCACCATTCCTGCCGGCTTTGACGACCCTCT

TCAGGCTGACGGTCTTTTCTCTTTGACCATCGGATTGCACGTCACAACTT

GTCAGGCCAAGCCATCTCTTGGAACTAACCCTCCTGTCACTTCCGGCCCT

GTGTCCTCGCTTCCAGCTTCCTCCACCACCCGCGCATCCTCGCCGCCTCC

TGTTTCTTCAACTCGTGTCTCTTCTCCCCCTGTCTCTTCCCCTCCAGTTT

CTCGCACCTCTTCTGCCCCTCCCCCTCCGGGCAACAGCACGCCGCCATCG

GGTCAGGTTTGCGTTGCCGGCACCGTTGCCGACGGCGAGTCTGGCAACTA

CATCGGCCTGTGCCAATTCAGCTGCAACTACGGTTACTGCCCACCAGGAC

CGTGTAAGTGCACCGCCTTTGGTGCTCCCATCTCGCCACCGGCATCCAAC

GGCCGCAACGGCTGCCCTCTGCCGGGAGAAGGCGATGGTTATCTGGGCCT

GTGCAGTTTCAGTTGTAACCATAATTACTGCCCGCCAACGGCATGTCAAT

ACTGCTAGGAGGGATCAATCTCAGTATGAGTATATGGAGGCTGCTGAAGG

ACCAATTAGCTGTTCTTATCGGCAGACGAAACCCATAGAGTAAGAAGTTA

AATAAAATGCAATTAATGTGTTTTCAAAAAAAAAAAAAAA
```
(There is a polyA tail since *Trichoderma harzianum* is fungi)

V) *Trichoderma harzianum*

1. General Information of of Mutanase from *Trichoderma harzianum*

Also see the world wide at .uniprot.org/uniprot/Q8WZM7;

2. The Protein Sequence of Mutanase from *Trichoderma harzianum*

See the world wide web at: .uniprot.org/uniprot/Q8WZM7.fasta)

```
>tr|Q8WZM7|Q8WZM7_TRIHA Alpha-1,3-glucanase
OS = Trichoderma harzianum GN = p3 PE = 2 SV = 1
                                      (SEQ ID NO: 20)
MLGVFRRLRLGALAAAALSSLGSAAPANVAIRSLEERASSADRLVFCHFM

IGIVGDRGSSADYDDDMQRAKAAGIDAFALNIGVDGYTDQQLGYAYDSAD

RNGMKVFISFDFNWWSPGNAVGVGQKIAQYANRPAQLYVDNRPFASSFAG

DGLDVNALRSAAGSNVYFVPNFHPGQSSPSNIDGALNWMAWDNDGNNKAP

KPGQTVTVADGDNAYKNWLGGKPYLAPVSTWVFNHFGPEVSYSKNWVFPS

GPLIYNRWQQVLQQGFPPRVEIVTWNDYGESHYVGPLKSKQFHDGNSKWVN

DMPHDGFLDLSKPFIAAYKNRDTDISKYVQNEQLVYWYRRNLKALDCDAT

DTTSNRPANNGSGNYFEGRPDGWQTMDDTVYVAALLKTAGSVTVTSGGTT

QTFQANAGANLFQIPASIGQQKFALTRNGQTVFSGTSLMDITNVCSCGIY

NFNPYVGTIPAGFDDPLQADGLFSLTIGLHVTTCQAKPSLGTNPPVTSGP

VSSLPASSTTRASSPPPVSSTRVSSPPVSSPPVSRTSSAPPPPGNSTPPS

GQVCVAGTVADGESGNYIGLCQFSCNYGYCPPGPCKCTAFGAPISPPASN

GRNGCPLPGEGDGYLGLCSFSCNHNYCPPTACQYC
```

3. Sequence of mRNA (*Trichoderma harzianum* Further Information can be Found at the world wide web at .ebi.ac.uk/ena/data/view/AJ243799&display=fasta)

```
>ENA|AJ243799|AJ243799.1 Trichoderma harzianum
mRNA for alpha-1,3-glucanase (p3 gene)
                                      (SEQ ID NO: 21)
ATGTTGGGCGTTTTCCGCCGCCTCAGGCTCGGCGCCCTTGCCGCCGCAGC

TCTGTCTTCTCTCGGCAGTGCCGCTCCCGCCAATGTTGCTATTCGGTCTC

TCGAGGAACGTGCTTCTTCTGCTGACCGTCTCGTATTCTGTCATTTCATG

ATTGGGATCGTGGGTGACCGTGGCAGCTCGGCAGATTATGATGACGATAT

GCAACGTGCCAAAGCCGCTGGCATTGACGCCTTCGCCCTGAACATCGGCG

TTGACGGCTATACCGACCAGCAGCTCGGCTATGCCTATGACTCTGCCGAT

CGTAATGGCATGAAAGTCTTCATTTCATTTGATTTCAACTGGTGGAGCCC

CGGCAATGCAGTTGGTGTTGGCCAGAAGATTGCGCAGTATGCCAACCGCC

CTGCCCAGCTGTATGTCGACAACCGGCCATTCGCCTCTTCCTTCGCCGGT

GACGGTCTGGATGTAAATGCGTTGCGCTCTGCTGCAGGCTCCAACGTTTA

CTTTGTGCCCAACTTCCACCCTGGTCAATCTTCCCCCTCCAACATTGATG

GCGCCCTTAACTGGATGGCCTGGGATAATGATGGAAACAACAAGGCACCC

AAGCCGGGCCAGACTGTCACAGTGGCAGACGGTGACAACGCTTATAAGAA

TTGGTTGGGTGGCAAGCCTTACCTGGCGCCTGTCTCAACTTGGGTTTTCA

ACCATTTCGGGCCCGAAGTTTCATATTCCAAGAACTGGGTTTTCCCAAGT

GGGCCTCTGATCTATAACCGGTGGCAACAAGTCTTGCAGCAAGGGTTCCC

AAGGGGTTGAGATCGTTACCTGGAATGACTACGGGGAATCTCACTACGTCG

GTCCCCTGAAGTCTAAGCAATTTCATGATGGGAACTCCAAATGGGTCAAT

GATATGCCCCACGATGGATTCCTGGATCTTTCGAAGCCGTTCATAGCCGC

ATATAAAAACAGGGATACCGACATCTCCAAGTATGTTCAAAATGAGCAGC

TTGTTTACTGGTACCGCCGCAACTTAAAGGCACTGGACTGTGACGCCACC

GACACAACCTCTAACCGCCCGGCTAACAATGGAAGCGGCAATTACTTTGA

GGGACGCCCCGATGGTTGGCAAACTATGGATGATACGGTTTACGTGGCGG

CACTTCTCAAGACTGCCGGTAGCGTCACGGTCACGTCTGGTGGCACCACT

CAAACGTTCCAGGCCAACGCCGGAGCCAATCTCTTCCAAATCCCGGCCAG

CATCGGCCAGCAAAAGTTTGCTCTGACTCGTAACGGTCAGACCGTCTTTA

GCGGAACCTCATTGATGGATATCACCAACGTTTGCTCTTGCGGTATCTAC

AACTTCAACCCATATGTTGGCACCATTCCTGCCGGCTTTGACGACCCTCT

TCAGGCTGACGGTCTTTTCTCTTTGACCATCGGATTGCACGTCACAACTT

GTCAGGCCAAGCCATCTCTTGGAACTAACCCTCCTGTCACTTCCGGCCCT

GTGTCCTCGCTTCCAGCTTCCTCCACCACCCGCGCATCCTCGCCGCCTCC

TGTTTCTTCAACTCGTGTCTCTTCTCCCCCTGTCTCTTCCCCTCCAGTTT

CTCGCACCTCTTCTGCCCCTCCCCCTCCGGGCAACAGCACGCCGCCATCG
```

-continued

```
GGTCAGGTTTGCGTTGCCGGCACCGTTGCCGACGGCGAGTCTGGCAACTA
CATCGGCCTGTGCCAATTCAGCTGCAACTACGGTTACTGCCCACCAGGAC
CGTGTAAGTGCACCGCCTTTGGTGCTCCCATCTCGCCACCGGCATCCAAC
GGCCGCAACGGCTGCCCTCTGCCGGGAGAAGGCGATGGTTATCTGGGCCT
GTGCAGTTTCAGTTGTAACCATAATTACTGCCCGCCAACGGCATGTCAAT
ACTGCTAGGAGGGATCAATCTCAGTATGAGTATATGGAGGCTGCTGAAGG
ACCAATTAGCTGTTCTTATCGGCAGACGAAACCCATAGAGTAAGAAGTTA
AATAAAATGCAATTAATGTGTTTTCAAAAAAAAAAAAAAAA
```

(There is a polyA tail since *Trichoderma harzianum* is fungi)

Dextranase (Dex) gene from *Penicillium minioluteum*
GenBank: L41562.1

See the world wide web at (.ncbi.nlm.nih.gov/nuccore/L41562.1)

The mature protein has 574 amino acids with MW at 67 KD. The optimum reaction condition is pH 5.5 and 40° C. The pH range is 3-6.

Amino Acid Sequence (SEQ ID NO: 22)

MATMLKLLALTLAISESAIGAVMHPPGNSHPGTHMGTTNNTHCGADFCTW
WHDSGEINTQTPVQPGNVRQSHKYSVQVSLAGTNNFHDSFVYESIPRNGN
GRIYAPTDPPNSNTLDSSVDDGISIEPSIGLNMAWSQFEYSHDVDVKILA
TDGSSLGSPSDVVIRPVSISYAISQSDDGGIVIRVPADANGRKFSVEFKT
DLYTFLSDGNEYVTSGGSVVGVEPTNALVIFASPFLPSGMIPHMTPDNTQ
TMTPGPINNGDWGAKSILYFPPGVYWMNQDQSGNSGKLGSNHIRLNSNTY
WVYLAPGAYVKGAIEYFTKQNFYATGHGILSGENYVYQANAGDNYIAVKS
DSTSLRMWWHNNLGGGQTWYCVGPTINAPPFNTMDFNGNSGISSQISDYK
QVGAFFFQTDGPEIYPNSVVHDVFWHVNDDAIKIYYSGASVSRATIWKCH
NDPIIQMGWTSRDISGVTIDTLNVIHTRYIKSETVVPSAIIGASPFYASG
MSPDSRKSISMTVSNVVCEGLCPSLFRITPLQNYKNFVVKNVAFPDGLQT
NSIGTGESIIPAASGLTMGLNISNWTVGGQKVTMENFQANSLGQFNIDGS
YWGEWQIS

DNA Sequence (SEQ ID NO: 23)

```
   1 ggcatagtaa tcccgacagc cgagtatgat ggagcttctt cggataatga tagcgccacc
  61 agaccttgct tgagctggag agctaaaaca ttaaacgcca cacgaccaac actctcatta
 121 gttgcgatag atgatgctcg gagctgttga aactcagaaa ttccttctat gcggggtctc
 181 caagatcgat cctgggggat gtgaatacta cggtggacct aattgacgcc ttgacaggtg
 241 atgttaagcg aaccaaggaa gaataatctg gggctagatg aagatgttga gctgtaaggt
 301 acggtacgtt cctattggct ttatcggagc ttctccgggt tactcagtct ttccgggagc
 361 atgatcattt ttgtattgtc caatagtaag cagaaactga gagccaccac aaactcaaaa
 421 cctcggtagc gaagtttccc ggaaccagtc aggattctca gaaactgtgc tcgtgttgcg
 481 gggaatccgc attctacgtc gtctggagca aggaaatgtt cgtgctggat tgaggaggat
 541 aggtaggttg gagaatctct tcagctaacc aatctataag catgctccgg taacctttag
 601 agtttcacat tcaacgtaat ttccaagata gccagagcgt ccttgaatta ctatgtagaa
 661 atcctaaaat ttcccctgta aaatgcaagt caacgagatg cgtgccctca atgtctctcg
 721 gcgctacccc ggaaatgatg cataaggcca agaatgtcac ccggtaactt tttcttcaga
 781 atatcctaag atttccatca aacacagtcg aataggtcaa tgctcgcgag agactttctg
 841 ccttcactct acgtcctact catagaagtt caacggctca attccggggt aatctagagt
 901 ttggacctca agggagatgt tgcaacaaat tgtactagaa cgatgcgctt gctttccaat
 961 acagtagttg acttcatata gcttccaaca aaagggatgg ggatgaaggc tctatagcga
1021 gaagtctata agaaagtgtc ctcataccctg tatctctcag tcgttcgaga acaatcccgg
1081 aaactatctt atcttgcgag aaagaagaca atatctcaaa cttatggcca caatgctaaa
1141 gctacttgcg ttgacccttg caattagcga gtccgccatt ggagcagtca tgcacccacc
1201 tggcaattct catcccggta cccatatggg cactacgaat aatacccatt gcggcgccga
1261 tttctgtacc tggtggcatg attcagggga gatcaatacg cagacacctg tccaaccagg
1321 gaacgtgcgc caatctcaca agtattccgt gcaagtgagc ctagctggta caaacaattt
1381 tcatgactcc tttgtatatg aatcgatccc ccggaacgga aatggtcgca tctatgctcc
```

-continued

```
1441 caccgatcca cccaacagca acacactaga ttcaagtgtg gatgatggaa tctcgattga 1501 gcctagtatc ggccttaata tggcatggtc ccaattcgag tacagccacg atgtagatgt 1561 aaagatcctg gccactgatg gctcatcgtt gggctcgcca agtgatgttg ttattcgccc 1621 cgtctcaatc tcctatgcga tttctcagtc tgacgatggt gggattgtca tccgggtccc 1681 agccgatgcg aacggccgca aattttcagt tgagttcaaa actgacctgt acacattcct 1741 ctctgatggc aacgagtacg tcacatcggg aggcagcgtc gtcggcgttg agcctaccaa 1801 cgcacttgtg atcttcgcaa gtccgtttct tccttctggc atgattcctc atatgacacc 1861 cgacaacacg cagaccatga cgccaggtcc tatcaataac ggcgactggg gcgccaagtc 1921 aattctttac ttcccaccag gtgtatactg gatgaaccaa gatcaatcgg gcaactcggg 1981 gaagttagga tctaatcata tacgtctaaa ctcgaacact tactgggtct accttgcccc 2041 cggtgcgtac gtgaagggtg ctatagagta ttttaccaag cagaacttct atgcaactgg 2101 tcatggtatc ctatcgggtg aaaactatgt ttaccaagcc aatgccggcg acaactacat 2161 tgcagtcaag agcgattcaa ccagcctccg gatgtggtgg cacaataacc ttggggggtgg 2221 tcaaacatgg tactgcgttg gcccgacgat caatgcgcca ccattcaata ctatggattt 2281 caatggaaat tctggcatct caagtcaaat tagcgactat aagcaggtgg gagccttctt 2341 cttccagacg gatggaccag aaatatatcc caatagtgtc gtgcacgacg tcttctggca 2401 cgtcaatgat gatgcaatca aaatctacta ttcgggagca tctgtatcgc gggcaacgat 2461 ctggaaatgt cacaatgacc caatcatcca gatgggatgg acgtctcggg atatcagtgg 2521 agtgacaatc gacacattaa atgttattca cacccgctac atcaaatcgg agacggtggt 2581 gccttcggct atcattgggg cctctccatt ctatgcaagt gggatgagtc ctgattcaag 2641 aaagtccata tccatgacgg tttcaaacgt tgtttgcgag ggtctttgcc cgtccctatt 2701 ccgcatcaca ccccttcaga actacaaaaa ttttgttgtc aaaaatgtgg ctttcccaga 2761 cgggctacag acgaatagta ttggcacagg agaaagcatt attccagccg catctggtct 2821 aacgatggga ctgaatatct ccaactggac tgttggtgga caaaaagtga ctatggagaa 2881 cttttcaagcc aatagcctgg ggcagttcaa tattgacggc agctattggg gggagtggca 2941 gattagctga attccagctc tcggagcgcg tgagtgcttc tacccgctcc tttacccttg 3001 tcgagagata aaggcataag ttagctcatg tgaaggcgat ttcagttcat tctctctttt 3061 tggagcttat ttcctgttcg accaattgtg acaccaactt gcctttcaaa agacgtggac 3121 gatatgtgta cggtaatcag tcaaatgaac gtcaacattc atttaataag gacatttcca 3181 ggtttcctta ctctgtcgat tatgcctaac tcgggttgat gtcttgtcag gatggaaaat 3241 ctcgttgtgt acttccagtg aaatgggcag ggctaagccc taaaccctaa cgcatacaat 3301 ttgtaggcac ctacccatgt aagttcacac ccagtcgact tataagtcta gatatttatg 3361 ctatgcaggc tctggaatga tttacattcc atgctataca tagttatttg caagaatttg 3421 cagacgagat aaaaatcaat ggacgaataa tcacgcatta ctccacaggc tcatgccacg 3481 gagcaagggt tcccccgaat ctaggccaga ccgggatgat attcaaccga ttctttttgc 3541 agtaactatc tccgtacgag ctgcacgagc taaacggatt atataaaggt gctaactgag 3601 cattggatcc gtcagttata tgaaatgca
```

2. Dextranase (Dex) Gene from *Penicillium aculeatum* (*Talaromyces aculeatus* Strain z01)
GenBank: KF999646.1. See the world wide web at .ncbi.nlm.nih.gov/nuccore/KF999646.1
The optimum pH is around 5. The pH range is 3-6.

Amino Acid Sequence (SEQ ID NO: 24)
MATMLKLLTLALAISESAIGAVLHPPGSSHPSTRTDTTNNTHCGADFCTW
WHDSGEINTQTPVQPGNVRQSHKYSVQVSLAGANNFQDSFVYESIPRNGN
GRIYAPTDPPNSNTLDSSVDDGISIEHSIGLNMAWSQFEYSQDVDIKILA
ADGSSLGSPSDVVIRPVSISYAISQSDDGGIVIRVPADANGRKFSVEFKN
DPYTFLSDGNEYVTSGGSVVGVEPTNALVIFASPFLPSGMIPHMTPDNTQ
TMTPGPINNGDWGSKSILYFPPGVYWMNQDQSGNSGKLGSNHIRLNSNTY
WVYFAPGAYVKGAIEYFTKQNFYATGHGVLSGENYVYQANAGENYVAVKS
DSTSLRMWWHNNLGGGQTWYCVGPTINAPPFNTMDFNGNSGISSQISDYK
QVGAFFFQTDGPEIYPNSVVHDVFWHVNDDAIKIYYSGASVSRATIWKCH
NDPIIQMGWTSRDISGVTIDTLNVIHTRYIKSETVVPSAIIGASPFYASG
MSPDSSKSISMTVSNVVCEGLCPSLFRITPLQNYKNFVVKNVAFPDGLQT
NSIGTGESIIPAASGLTMGLDISNWSVGGQKVTMQNFQANSLGQFDIDGS
YWGEWQIN DNA Sequence (SEQ ID NO: 25)
```
   1 atggccacaa tgctaaagct acttacgttg gcccttgcaa ttagcgagtc tgccattgga
  61 gcagtcctgc acccacctgg cagttctcat cccagtaccc gtacggacac tacgaataat
 121 acccattgcg gtgccgactt ctgtacctgg tggcatgatt caggcgagat caacacacag
 181 acacctgtcc aaccggggaa cgtgcgccaa tctcacaagt attccgtaca agtgagccta
 241 gctggtgcga acaactttca ggactccttt gtatatgaat cgatccctcg gaacggaaat
 301 ggtcgcatct atgctcccac cgatccaccc aacagcaaca cactagattc aagtgttgat
 361 gatggaatct cgattgaaca tagtattggc ctcaatatgg catggtccca attcgagtac
 421 agccaggatg tcgatataaa gatcctggcc gctgatggct catcgttggg ctcaccaagt
 481 gatgttgtta ttcgccccgt ctcaatctcc tatgcaattt ctcaatccga cgatggcgga
 541 attgtcattc gggtcccagc cgatgcgaac ggccgcaaat tttcagtcga gttcaaaaat
 601 gacccgtaca cgttcctctc tgacggcaac gagtacgtca tcgggagg cagcgttgtc
 661 ggcgttgagc ctaccaacgc acttgtgatc ttcgcaagcc cgtttcttcc gtcaggcatg
 721 attcctcata tgacacccga caacacgcag accatgacac caggacctat caataacggc
 781 gactgggggct ccaagtcaat tctttatttc ccaccgggcg tatactggat gaaccaagat
 841 caatcaggca actcggggaa attaggatct aatcatatac gcctgaactc gaacacctac
 901 tgggtctact ttgccccagg tgcgtacgtg aagggtgcta tagagtattt caccaagcag
 961 aacttctatg caactggtca tggtgtccta tcgggtgaaa actatgttta ccaagccaat
1021 gctggcgaaa actacgttgc ggtcaagagc gattcgacta gcctccggat gtggtggcac
1081 aataacctgg gaggtggaca aacatggtac tgcgttgggc ctacgatcaa tgcgccgcca
1141 tttaacacaa tggatttcaa tggaaattcc ggtatctcaa gtcaaattag cgactataag
1201 caggtgggag ctttcttctt tcagacggat ggaccagaaa tttatcccaa tagtgtcgtg
1261 cacgacgtct tctggcatgt caatgatgat gcaatcaaaa tctactattc cggagcatct
1321 gtctcgcggg caacgatctg gaaatgtcac aacgatccaa tcatccagat gggatggacg
1381 tctcgggata tcagtggagt gacaatcgac acattgaatg tcatccacac ccgctacatc
1441 aagtcggaga cggtggtgcc ttcggctatc attggggctt ctccattcta tgcaagtggg
1501 atgagtcctg attcaagcaa gtctatatcc atgacggttt caaacgttgt ctgcgaggga
1561 ctttgcccgt ctctgttccg aatcacacct ttacagaact acaagaattt tgttgtcaaa
1621 aatgtggctt tcccagatgg gctacagacg aatagtattg gcacgggaga aagcattatt
1681 ccagccgcat ctggtctaac gatgggactg gatatctcca actggtctgt tggtggtcag
1741 aaggtgacta tgcagaactt tcaagccaat agtctggggc aattcgacat tgacggcagc
```

-continued

```
1801 tattgggggg agtggcagat taactagctg aataatattg cagctttcag ggcgcatgag 1861 tgcttgtacc cgctccttta cccttgtc
```

3. *Penicillium funiculosum* dexA Gene for Dextranase GenBank: AJ272066.1. See the world wide web at .ncbi.nlm.nih.gov/nuccore/7801166
The optimum pH is around 5.5. The optimum temperature is 60° C. The pH range is 5-7.5. See the world wide web at .sciencedirect.com/science/article/pii/S0032959298001277
Amino Acid Sequence (SEQ ID NO: 26)
MATMLKLLALTLAISESAIGAVMHPPGVSHPGTHTGTTNNTHCGADFCTW
WHDSGEINTQTPVQPGNVRQSHKYSVQVSLAGTNNFHDSFVYESIPRNGN
GRIYAPTDPSNSNTLDSSVDDGISIEPSIGLNMAWSQFEYSQDVDIKILA
TDGSSLGSPSDVVIRPVSISYAISQSNDGGIVIRVPADANGRKFSVEFKN
DLYTFLSDGNEYVTSGGSVVGVEPTNALVIFASPFLPSGMIPHMKPHNTQ
TMTPGPINNGDWGAKSILYFPPGVYWMNQDQSGNSGKLGSNHIRLNSNTY
WVYLAPGAYVKGAIEYFTKQNFYATGHGVLSGENYVYQANAGDNYVAVKS
DSTSLRMWWHNNLGGGQTWYCVGPTINAPPFNTMDFNGNSGISQISDYKQ
VGAFFFQTDGPEIYPNSVVHDVFWHVNDDAIKIYYSGASVSRATIWKCHN
DPIIQMGWTSRDISGVTIDTLNVIHTRYIKSETVVPSAIIGASPFYASGM
SPDSSKSISMTVSNVVCEGLCPSLFRITPLQNYKNFVVKNVAFPDGLQTN
SIGTGESIIPAASGLTMGLNISSWTVGGQKVTMENFQANSLGQFNIDGSY
WGEWQISRISSSQSA DNA Sequence (SEQ ID NO: 27)
```
   1 atggccacaa tgctaaagct acttgcgttg acccttgcaa ttagcgagtc cgccattgga 61 gcagtcatgc acccacctgg cgtttctcat cccggtaccc atacgggcac tacgaataat 121 acccattgcg gcgccgactt ctgtacctgg tggcatgatt cagggagat caacacgcag 181 acacctgtcc aaccagggaa cgtgcgccaa tctcacaagt attccgtgca agtgagtcta 241 gctggtacaa acaactttca tgactccttt gtatatgaat cgatccccg gaacggaaat 301 ggtcgcatct atgctcccac cgatccatcc aacagcaaca cattagattc aagcgtggat 361 gatgaatct cgattgagcc tagtatcggc ctcaatatgg catggtccca attcgagtac 421 agccaggatg tcgatataaa gatcctggca actgatggct catcgttggg ctcaccaagt 481 gatgttgtta ttcgcccgt ctcaatctcc tatgcgattt ctcagtccaa cgatggcggg 541 attgtcatcc gggtcccagc cgatgcgaac ggccgcaaat tttcagtcga attcaaaaat 601 gacctgtaca ctttcctctc tgatggcaac gagtacgtca catcgggagg tagcgtcgtc 661 ggcgttgagc ctaccaacgc acttgtgatc ttcgcaagtc cgtttcttcc ttctggcatg 721 attcctcata tgaaacccca caacacgcag accatgacgc caggtcctat caataacggc 781 gactggggcg ccaagtcaat tctttacttc ccaccaggtg tatactggat gaaccaagat 841 caatcgggca actcgggtaa attaggatct aatcatatac gtctaaactc gaacacttac 901 tgggtctacc ttgccccgg tgcgtacgtg aagggtgcta tagagtattt caccaagcaa 961 aacttctatg caactggtca tggtgtccta tcaggtgaaa actatgttta ccaagccaat 1021 gctggcgaca actatgttgc agtcaagagc gattcgacca gcctccggat gtggtggcac 1081 aataaccttg gggtggtca aacatgtac tgcgttggcc cgacgatcaa tgcgccacca 1141 ttcaacacta tggatttcaa tggaaattct ggcatctcaa gtcaaattag cgactataag 1201 caggtgggag ccttcttctt ccagacggat ggaccagaaa tctatcccaa tagtgtcgtg 1261 cacgacgtct tctggcacgt caatgatgat gcaatcaaaa tctactattc gggagcatct 1321 gtatcgcggg caacgatctg gaaatgtcac aatgacccaa tcatccagat gggatggaca 1381 tctcgggata tcagtggagt gacaatcgac acattaaatg ttattcacac ccgctacatc 1441 aaatcggaga cggtggtgcc ttcggctatc attggggcct ctccattcta tgcaagtggg -continued

```
1501 atgagtcccg attcaagcaa gtccatatcc atgacggttt caaacgttgt ttgcgagggt 1561 ctttgcccgt ccctgttccg catcacaccc ctacagaact acaaaaattt tgttgtcaaa 1621 aatgtggctt tcccagatgg gctacagaca aatagtattg gcacaggaga aagcattatt 1681 ccagccgcat ctggtctaac gatgggacta aatatctcca gctggactgt tggtggacaa 1741 aaagtgacaa tggagaactt tcaagccaat agcctggggc agttcaatat tgacggcagc 1801 tattgggggg agtggcagat tagtcgaatt tccagctctc agagcgcgtg agtgcttcta 1861 cccgctcctt taccctggtc gaaggatcaa ggcataagtt agctcatgtg aaggcgattt 1921 cagttcattc tctctttttt ggagctcatt tccttttcga ccaattgtga caccaaattg 1981 ccatgtgtac tgtaattggt caaatgaacg ttaaccttcg atttaatatg gacatttcca 2041 ggtttcctta ctctgtcgat tatgcctaac tcgggttgat gtcttgtcag gatgaaaatc 2101 tcgttgtcat gtacttcgag tgaaatgggc agggctaacc cctaagccct aacgcccaat 2161 cgacttataa gtctagatgt ttatgctatg caggctctgg aatgatttac attccatgct 2221 ataca
```

While certain of the preferred embodiments of the present invention have been described and specifically exemplified above, it is not intended that the invention be limited to such embodiments. Various modifications may be made thereto without departing from the scope and spirit of the present invention, as set forth in the following claims.

SEQUENCE LISTING

```
<160> NUMBER OF SEQ ID NOS: 28

<210> SEQ ID NO 1
<211> LENGTH: 3801
<212> TYPE: DNA
<213> ORGANISM: Artificial Sequence
<220> FEATURE:
<223> OTHER INFORMATION: codon optimized mutanase

<400> SEQUENCE: 1
gcaggtggcc cgaatcttac tccaggtaaa ccaattactg ctagtggtca atctcaaacc       60
tatagccctc aaaatgtaaa agatggcaat caaaatactt actgggaaag tactaacaat      120
gccttccctc aatggattca agttgatttg ggtgcaagta ctggcattga tcaaattgtt      180
cttaagttac cagctagctg ggaagctcgt actcaaactc ttgctgttca aggtagtttg      240
aatggttcta ctttcactga tattgtaggt tctgcaaatt atgtattcag tccttctgta      300
ggtaataaca ctgttactat taattttacc gccacaagca cccgttatgt tcgcttgtac      360
gtaactgcga acactggttg gccagctgct caactgtctg aatttgaaat ttatggttct      420
ggtgaccaga ctcctgcacc tgatacttat caagctgaaa gtgctgcttt atctggtggc      480
gctaaagtaa atactgatca tgccggctac ataggtactg gttttgttga tggttattgg      540
actcaaggcg ctactactac cttttctgta aacgcgccta ctgctggtaa ttacgatgta      600
actctgaggt atggtaacgc aaccggcagt aataaaactg tatccttgta cgtaaatggc      660
gctaaaattc gtcaaacaac tttaccaagt ctacctaact gggattcatg gagtagcaag      720
actgaaactc ttaatttaaa tgctggtagc aacaccattg cttataaata cgaccctggc      780
gattctggta atgtaaatct tgatcaaatc actgtagaag catctacttc aactcctact      840
cctactccat ctcctactcc tacacctact ccaactccta ctcctactcc tactcctaca      900
ccaacaccta ctcctacccc aacccctact cctacaccta cacctacacc tactcctact      960
cctcctcctg gtggtaatat tgccataggc aaatctattt ccgcatctag tcacactcaa     1020
```

```
acttatgttg ctgagaacgc aaatgataac gatgtaaata cttactggga aggtggcggt    1080
aatcctagta ctttaacttt ggatcttggc gctaattata atattacttc tattgttcta    1140
aaactaaacc catcctctat atgggcagcc cgtactcaaa ctattcaagt tttgggccat    1200
gatcaaaata ctactacatt cagtaattta gtatctgcta atcttactc tttcgatcct     1260 gcttctggta atactgttac cattccagtt accgctactg ttaaacgttt gcagttgaac    1320
attacttcta attccggtgc ccctgctggt caagtagctg agttccaagt tttcggtact    1380
cctgctccaa atcctgattt gactattacc ggtatgtctt ggtctccttc ttctccagtt    1440
gagacagatg caattactct gaatgctact gttaaaaaca atggtaatgc cagtgcagcc    1500
gctaccaccg taaatttcta cctaaataac gagctagctg ttctgctcc tgtagcagct     1560 ctagcggcag cgcttctgc aactgttccg ctaaatgtag gtgctaaaac cgccgccaca     1620
tacgctgtag gtgctaaagt agatgaaagt aatgcagtaa ttgagttaaa cgagtctaac    1680
aatagctaca ctaatcctgc ttcattggtt gttgctccag ttagtagttc tgatttagtt    1740
ggcactgttt cttggactcc aagcactcct attgcaaaca atgctgtttc ttttaacgta    1800
aatcttaaaa atcaaggcac tattgcttct gccggtggtt ctcacggtgt tactgtagtt    1860
cttaaaaatg cttccggttc taccgttcaa actttcagtg gttcttacac cggtagtctt    1920
gctccgggag cttccgtaaa tattacccctt cctggtacct ggactgctgc tgctggtagc    1980
tatactgtaa ctgcaaccgt tgcggcagac gctaacgaac ttcctatcaa gcaagccaac    2040
aatgcaaaca cagcaagtct aaccgtatat tctgctcgtg gtgcaagcat gccatacagt    2100
cgttacgata ccgaggatgc cacccttggt ggtggcgcta ctctaaaatc cgctccgaca    2160
ttcgatcaag cgcttactgc atctgaagcc accggtcaat tgtacgctgc gttaccatct    2220
aacggctctt atcttcaatg gaccgtacgt caaggtcagg gtggtgcagg cgttactatg    2280
agatttacta tgccagattc tgctgacggc atgggcttaa acggtagttt agatgtttac    2340
gtaaacggta caaaagtaaa aaccgtatct ctaaccagtt actatagctg gcagtatttc    2400
tctggtgata tgccaggaga cgctccaagc gctggtcgtc ctttattccg ttttgatgaa    2460
gttcattgga aattagatac tccttttgaaa ccaggagata ctattcgcat acaaaagaac    2520
aacggtgata gcctagaata cggtgtagac tttattgaaa ttgaaccagt tcctgctgct    2580
atctctcgtc cggctaactc tgtttccgta actgattacg gtgctgttcc taacgatgga    2640
caggacgatc ttaccgcttt taaagcagcc gtaaacgcag ctgtagcatc cgataaaatc    2700
ttgtatattc cagaaggcac tttccacttg gtaacatgt gggagattgg ttccgtaagt     2760
aacatgatcg atcacattac tattactgga gctggtattt ggtacactaa catccagttt    2820
accaacgcca atcctgcttc cggtggcatc tctctacgta ttactggtaa acttgatttc    2880
agcaacgttt acttgaactc taatttgcgt tctcgttatg gtcaaaatgc cgtttataaa    2940
ggttttatgg ataacttcgg taccaattcc gtaattcgtg acgtatgggt agaacacttc    3000
gaatgtggtt tctgggtagg tgattacggt catactcctg ctattcgcgc aagcggtctg    3060
ttaattgaaa acagccgaat ccgtaacaac ctagctgatg gtgtaaactt cgcccaaggt    3120
accagcaatt ctaccgtacg caacagcagc ttacgtaaca acggtgatga cgcccttgct    3180
gtatggacta gtaatactaa cggtgctcca gaaggcgtaa acaataccctt ctcttacaac    3240 accatcgaaa acaactggcg cgctggaggt attgccttct tcggaggaag cggacataag    3300
gccgatcaca actacatagt agattgtgta ggtggttctg gtatccgtat gaataccgtt    3360
ttcccaggat atcacttcca gaacaatacc ggtattgttt tctctgacac taccatagta    3420
```

-continued

| | |
|---|---|
| aactgcggta ctagcaaaga tctatacaac ggtgaacgcg gtgctatcga tttggaagca | 3480 |
| tctaacgacg ccatcagaaa cgttactttt accaacatcg atattatcaa ctctcagcgc | 3540 |
| gatgctatcc agttcggtta tggtggtggt ttcaccaata tcgttttcaa caacatcaac | 3600 |
| attaacggaa ccggtcttga tggtgtaacc acctctcgtt tctctggacc tcatttaggc | 3660 |
| gcggcgatct tcacctatac cggtaacggt agtgctactt tcaacaattt acgcaccagc | 3720 |
| aatatcgctt atccaaattt atattatatc cagagcggtt tcaatttaat catcaataat | 3780 |
| catcatcacc atcaccacta a | 3801 |

<210> SEQ ID NO 2
<211> LENGTH: 2553
<212> TYPE: DNA
<213> ORGANISM: Artificial Sequence
<220> FEATURE:
<223> OTHER INFORMATION: codon optimized dextranase

<400> SEQUENCE: 2

| | |
|---|---|
| atggaacagt caaataggca acggctgaac cagctatta ggtcaaatga acggtggat | 60 |
| tcggccatta actcttttca agagacagac cttaaggtgc aagagaaaga ggatgctgcg | 120 |
| gctgcagtac agacagaatc ggcgtcaata gattctaatg aacaggaaca atcggtctct | 180 |
| gcaaatacta acacacaacc tcaagcgaag aaactttcta acaattccca tcaggagcca | 240 |
| atgcaaatgg tatctgccgc caataaagaa agggctgtgc tagaaactgc acagaaccaa | 300 |
| aagaatggca acatgataaa tctgacaaca gataaagcag tctatcaggc gggagaggct | 360 |
| gttcatttga atcttacttt aaacaataca acatctttag cccaaaatat tacagctact | 420 |
| gttgaggttt attcccttga aaataaatta agcacacttc agtatacgaa gtatcttctg | 480 |
| cctaatgaaa gttatacaac tcaaaaaggt gaattcgtta ttcctgcaaa ctccttagct | 540 |
| aataatcgcg gttatctttt gaaggttaac atatcagata gccaaaataa tattttagag | 600 |
| cagggcaatc gggctattgc ggttgaggat gactggcgta cctttccgcg ttatgctgct | 660 |
| attggaggtt ctcaaaaaga caataacagt gtcttgacta agaacttacc agattattat | 720 |
| cgcgaattag agcagatgaa aaatatgaac attaattcct atttcttcta tgatgtttat | 780 |
| aagtctgcta caaatccttt ccctaatgtt cctaagtttg atcagtcttg gaattggtgg | 840 |
| agccattcgc aggttgaaac agatgctgtt aaagccttgg tcaatcgtgt ccatcaaact | 900 |
| ggcgctgttg ccatgctcta taatatgatt ttagcacaga atgctaatga acggctgtt | 960 |
| ttaccagata ctgagtacat ctataattat gagactggtg ttatggtca aaatggtcag | 1020 |
| gtcatgactt actctattga tgataagcca ctgcaatatt attacaatcc tttgagtaaa | 1080 |
| agttggcaaa attatatttc taatgccatg gctcaagcta tgaaaactgg cggttttgat | 1140 |
| ggctggcagg gagatacaat tggagataat cgtgttcttt cccataatca aaaggacagt | 1200 |
| cgagatattg ctcattcctt tatgttatct gatgtctatg ctgaatttct caataaaatg | 1260 |
| aaggaaaaac tgcctcagta ttatttaaca ctcaatgatg ttaatggtga aaatatcagc | 1320 |
| aaactcgcca acagcaaaca agatgtgatt tacaatgaat tatggccttt tggaacttca | 1380 |
| gctttgggga accgtcccca agaaagttat ggtgacttga agctcgtgt tgatcaagtt | 1440 |
| cgccaagcga cagggaaatc tttgattgtc ggagcttata tggaagagcc taaatttgat | 1500 |
| gataatagga ttcctctcaa tggtgcagcg cgtgacgttt agcttcagc aacttaccaa | 1560 |
| acagatgcgg ttctgctgac aactgcggcc attgcggcag caggaggata tcacatgtct | 1620 |

```
ctggctgctc tggctaatcc taatgatggg ggtggtgtcg gtgtcttaga aacagcttat    1680
tatccaacac aaagcctcaa ggtttcgaaa gagctcaatc gtaaaaacta tcattaccaa    1740
caatttatta cggcttatga aaatcttttg cgtgataaag ttgaaaatga ttctgctgaa    1800
cctcagactt tcactgctaa cggtcggcag ctatcgcaag atgctttggg gatcaatggc    1860
gatcaggttt ggacttatgc caaaaaggga aacgatttca gaacgattca attgctcaac    1920
cttatgggaa ttcatctgac tggaaaaat gaagatggtt atgaaaataa taaaacacct    1980
gatgagcaaa ccaatttatt ggttacttat cctttgactg gtgtatctat ggcagaggct    2040
gatcgaatag ctaaacaagt ctatctgacg tcaccagatg attggctgca atctagtatg    2100
atttctctaa cgactcaggt aaaaacgaat gagaatggcg atcctgttct ttatattcaa    2160
gtgccaagac tgacgctttg ggatatgatt tatattaatg aaaccattaa accagaaacg    2220
cctaaagttc cagaacagcc ccaacatcct gctaggacac ttgaaccagc aattccgcaa    2280
actccagaag cagtcagccc tctcccagta gctaataagc aggcagaaga tggaaataaa    2340
aatgagcttg tttcagcttt aaccggtgaa gaaaatgact tgcagctgcc aactctttcc    2400
aaacgatcat tgtcaatctc ccaagcagag ttaccgcaaa caggagataa caatgaaacg    2460
cgctccaatc tcctcaaagt gataggtgct ggtgcgcttc taatcggcgc tgcaggatta    2520
ttaagcttga taaagggtag aaaaaatgat tga                                 2553
```

```
<210> SEQ ID NO 3
<211> LENGTH: 16
<212> TYPE: PRT
<213> ORGANISM: Artificial Sequence
<220> FEATURE:
<223> OTHER INFORMATION: CSPC16

<400> SEQUENCE: 3

Thr Phe Phe Arg Leu Phe Asn Arg Ser Phe Thr Gln Ala Leu Gly Lys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: G2
<220> FEATURE:
<221> NAME/KEY: MOD_RES
<222> LOCATION: (16)..(16)
<223> OTHER INFORMATION: AMIDATION

<400> SEQUENCE: 4

Lys Asn Leu Arg Ile Ile Arg Lys Gly Ile His Ile Ile Lys Lys Tyr
1               5                   10                  15

<210> SEQ ID NO 5
<211> LENGTH: 35
<212> TYPE: PRT
<213> ORGANISM: Artificial Sequence
<220> FEATURE:
<223> OTHER INFORMATION: C16G2
<220> FEATURE:
<221> NAME/KEY: MOD_RES
<222> LOCATION: (35)..(35)
<223> OTHER INFORMATION: AMIDATION

<400> SEQUENCE: 5

Thr Phe Phe Arg Leu Phe Asn Arg Ser Phe Thr Gln Ala Leu Gly Lys
1               5                   10                  15
```

Gly Gly Gly Lys Asn Leu Arg Ile Ile Arg Lys Gly Ile His Ile Ile
            20                  25                  30

Lys Lys Tyr
        35

<210> SEQ ID NO 6
<211> LENGTH: 8
<212> TYPE: PRT
<213> ORGANISM: Artificial Sequence
<220> FEATURE:
<223> OTHER INFORMATION: CSPM8

<400> SEQUENCE: 6

Thr Phe Phe Arg Leu Phe Asn Arg
1               5

<210> SEQ ID NO 7
<211> LENGTH: 27
<212> TYPE: PRT
<213> ORGANISM: Artificial Sequence
<220> FEATURE:
<223> OTHER INFORMATION: M8G2
<220> FEATURE:
<221> NAME/KEY: MOD_RES
<222> LOCATION: (27)..(27)
<223> OTHER INFORMATION: AMIDATION

<400> SEQUENCE: 7

Thr Phe Phe Arg Leu Phe Asn Arg Gly Gly Gly Lys Asn Leu Arg Ile
1               5                   10                  15

Ile Arg Lys Gly Ile His Ile Ile Lys Lys Tyr
            20                  25

<210> SEQ ID NO 8
<211> LENGTH: 11
<212> TYPE: PRT
<213> ORGANISM: Artificial Sequence
<220> FEATURE:
<223> OTHER INFORMATION: S6L3-33

<400> SEQUENCE: 8

Phe Lys Lys Phe Trp Lys Trp Phe Arg Arg Phe
1               5                   10

<210> SEQ ID NO 9
<211> LENGTH: 31
<212> TYPE: PRT
<213> ORGANISM: Artificial Sequence
<220> FEATURE:
<223> OTHER INFORMATION: C16-33

<400> SEQUENCE: 9

Thr Arg Arg Arg Leu Phe Asn Arg Ser Phe Thr Gln Ala Leu Gly Lys
1               5                   10                  15

Ser Gly Gly Gly Phe Lys Lys Phe Trp Lys Trp Phe Arg Arg Phe
            20                  25                  30

<210> SEQ ID NO 10
<211> LENGTH: 23
<212> TYPE: PRT
<213> ORGANISM: Artificial Sequence
<220> FEATURE:
<223> OTHER INFORMATION: M8-33

<400> SEQUENCE: 10

Thr Phe Phe Arg Leu Phe Asn Arg Ser Gly Gly Gly Phe Lys Lys Phe

```
                1               5                   10                  15
Trp Lys Trp Phe Arg Arg Phe
                20

<210> SEQ ID NO 11
<211> LENGTH: 5
<212> TYPE: PRT
<213> ORGANISM: Artificial Sequence
<220> FEATURE:
<223> OTHER INFORMATION: elastin-like biopolymer

<400> SEQUENCE: 11

Gly Val Gly Val Pro
1               5

<210> SEQ ID NO 12
<211> LENGTH: 1146
<212> TYPE: PRT
<213> ORGANISM: Paenibacillus humicus

<400> SEQUENCE: 12

Met Arg Ile Arg Thr Lys Tyr Met Asn Trp Met Leu Val Leu Val Leu
1               5                   10                  15

Ile Ala Ala Gly Phe Phe Gln Ala Ala Gly Pro Ile Ala Pro Ala Thr
                20                  25                  30

Ala Ala Gly Gly Ala Asn Leu Thr Leu Gly Lys Thr Val Thr Ala Ser
            35                  40                  45

Gly Gln Ser Gln Thr Tyr Ser Pro Asp Asn Val Lys Asp Ser Asn Gln
        50                  55                  60

Gly Thr Tyr Trp Glu Ser Thr Asn Asn Ala Phe Pro Gln Trp Ile Gln
65                  70                  75                  80

Val Asp Leu Gly Ala Ser Thr Ser Ile Asp Gln Ile Val Leu Lys Leu
                85                  90                  95

Pro Ser Gly Trp Glu Thr Arg Thr Gln Thr Leu Ser Ile Gln Gly Ser
                100                 105                 110

Ala Asn Gly Ser Thr Phe Thr Asn Ile Val Gly Ser Ala Gly Tyr Thr
            115                 120                 125

Phe Asn Pro Ser Val Ala Gly Asn Ser Val Thr Ile Asn Phe Ser Ala
        130                 135                 140

Ala Ser Ala Arg Tyr Val Arg Leu Asn Phe Thr Ala Asn Thr Gly Trp
145                 150                 155                 160

Pro Ala Gly Gln Leu Ser Glu Leu Glu Ile Tyr Gly Ala Thr Ala Pro
                165                 170                 175

Thr Pro Thr Pro Thr Pro Thr Pro Thr Pro Thr Pro Thr Pro Thr Pro
                180                 185                 190

Thr Pro Thr Pro Thr Val Thr Pro Ala Pro Ser Ala Thr Pro Thr Pro
            195                 200                 205

Thr Pro Pro Ala Gly Ser Asn Ile Ala Val Gly Lys Ser Ile Thr Ala
        210                 215                 220

Ser Ser Ser Thr Gln Thr Tyr Val Ala Ala Asn Ala Asn Asp Asn Asn
225                 230                 235                 240

Thr Ser Thr Tyr Trp Glu Gly Gly Ser Asn Pro Ser Thr Leu Thr Leu
                245                 250                 255

Asp Phe Gly Ser Asn Gln Ser Ile Thr Ser Val Val Leu Lys Leu Asn
            260                 265                 270

Pro Ala Ser Glu Trp Gly Thr Arg Thr Gln Thr Ile Gln Val Leu Gly
        275                 280                 285
```

```
Ala Asp Gln Asn Ala Gly Ser Phe Ser Asn Leu Val Ser Ala Gln Ser
    290                 295                 300
Tyr Thr Phe Asn Pro Ala Thr Gly Asn Thr Val Thr Ile Pro Val Ser
305                 310                 315                 320
Ala Thr Val Lys Arg Leu Gln Leu Asn Ile Thr Ala Asn Ser Gly Ala
                325                 330                 335
Pro Ala Gly Gln Ile Ala Glu Phe Gln Val Phe Gly Thr Pro Ala Pro
            340                 345                 350
Asn Pro Asp Leu Thr Ile Thr Gly Met Ser Trp Thr Pro Ser Ser Pro
        355                 360                 365
Val Glu Ser Gly Asp Ile Thr Leu Asn Ala Val Val Lys Asn Ile Gly
    370                 375                 380
Thr Ala Ala Ala Gly Ala Thr Thr Val Asn Phe Tyr Leu Asn Asn Glu
385                 390                 395                 400
Leu Ala Gly Thr Ala Pro Val Gly Ala Leu Ala Gly Ala Ser Ala
                405                 410                 415
Asn Val Ser Ile Asn Ala Gly Ala Lys Ala Ala Thr Tyr Ala Val
                420                 425                 430
Ser Ala Lys Val Asp Glu Ser Asn Ala Val Ile Glu Gln Asn Glu Gly
                435                 440                 445
Asn Asn Ser Tyr Ser Asn Pro Thr Asn Leu Val Ala Pro Val Ser
450                 455                 460
Ser Ser Asp Leu Val Ala Val Thr Ser Trp Ser Pro Gly Thr Pro Ser
465                 470                 475                 480
Gln Gly Ala Ala Val Ala Phe Thr Val Ala Leu Lys Asn Gln Gly Thr
                485                 490                 495
Leu Ala Ser Ala Gly Gly Ala His Pro Val Thr Val Leu Lys Asn
                500                 505                 510
Ala Ala Gly Ala Thr Leu Gln Thr Phe Thr Gly Thr Tyr Thr Gly Ser
            515                 520                 525
Leu Ala Ala Gly Ala Ser Ala Asn Ile Ser Val Gly Ser Trp Thr Ala
530                 535                 540
Ala Ser Gly Thr Tyr Thr Val Ser Thr Thr Val Ala Ala Asp Gly Asn
545                 550                 555                 560
Glu Ile Pro Ala Lys Gln Ser Asn Asn Thr Ser Ser Ala Ser Leu Thr
                565                 570                 575
Val Tyr Ser Ala Arg Gly Ala Ser Met Pro Tyr Ser Arg Tyr Asp Thr
            580                 585                 590
Glu Asp Ala Val Leu Gly Gly Ala Val Leu Arg Thr Ala Pro Thr
            595                 600                 605
Phe Asp Gln Ser Leu Ile Ala Ser Glu Ala Ser Gly Gln Lys Tyr Ala
        610                 615                 620
Ala Leu Pro Ser Asn Gly Ser Ser Leu Gln Trp Thr Val Arg Gln Gly
625                 630                 635                 640
Gln Gly Gly Ala Gly Val Thr Met Arg Phe Thr Met Pro Asp Thr Ser
                645                 650                 655
Asp Gly Met Gly Gln Asn Gly Ser Leu Asp Val Tyr Val Asn Gly Thr
            660                 665                 670
Lys Ala Lys Thr Val Ser Leu Thr Ser Tyr Tyr Ser Trp Gln Tyr Phe
        675                 680                 685
Ser Gly Asp Met Pro Ala Asp Ala Pro Gly Gly Arg Pro Leu Phe
    690                 695                 700
```

```
Arg Phe Asp Glu Val His Phe Lys Leu Asp Thr Ala Leu Lys Pro Gly
705                 710                 715                 720

Asp Thr Ile Arg Val Gln Lys Gly Gly Asp Ser Leu Glu Tyr Gly Val
            725                 730                 735

Asp Phe Ile Glu Ile Glu Pro Ile Pro Ala Ala Val Ala Arg Pro Ala
            740                 745                 750

Asn Ser Val Ser Val Thr Glu Tyr Gly Ala Val Ala Asn Asp Gly Lys
            755                 760                 765

Asp Asp Leu Ala Ala Phe Lys Ala Ala Val Thr Ala Ala Val Ala Ala
770                 775                 780

Gly Lys Ser Leu Tyr Ile Pro Glu Gly Thr Phe His Leu Ser Ser Met
785                 790                 795                 800

Trp Glu Ile Gly Ser Ala Thr Ser Met Ile Asp Asn Phe Thr Val Thr
                805                 810                 815

Gly Ala Gly Ile Trp Tyr Thr Asn Ile Gln Phe Thr Asn Pro Asn Ala
                820                 825                 830

Ser Gly Gly Gly Ile Ser Leu Arg Ile Lys Gly Lys Leu Asp Phe Ser
                835                 840                 845

Asn Ile Tyr Met Asn Ser Asn Leu Arg Ser Arg Tyr Gly Gln Asn Ala
850                 855                 860

Val Tyr Lys Gly Phe Met Asp Asn Phe Gly Thr Asn Ser Ile Ile His
865                 870                 875                 880

Asp Val Trp Val Glu His Phe Glu Cys Gly Met Trp Val Gly Asp Tyr
                    885                 890                 895

Ala His Thr Pro Ala Ile Tyr Ala Ser Gly Leu Val Val Glu Asn Ser
                900                 905                 910

Arg Ile Arg Asn Asn Leu Ala Asp Gly Ile Asn Phe Ser Gln Gly Thr
            915                 920                 925

Ser Asn Ser Thr Val Arg Asn Ser Ile Arg Asn Asn Gly Asp Asp
930                 935                 940

Gly Leu Ala Val Trp Thr Ser Asn Thr Asn Gly Ala Pro Ala Gly Val
945                 950                 955                 960

Asn Asn Thr Phe Ser Tyr Asn Thr Ile Glu Asn Asn Trp Arg Ala Ala
            965                 970                 975

Ala Ile Ala Phe Phe Gly Gly Ser Gly His Lys Ala Asp His Asn Tyr
            980                 985                 990

Ile Ile Asp Cys Val Gly Gly Ser  Gly Ile Arg Met Asn  Thr Val Phe
            995                 1000                1005

Pro Gly Tyr His Phe Gln Asn Asn  Thr Gly Ile Thr  Phe Ser Asp
    1010                1015                1020

Thr Thr Ile Ile Asn Ser Gly  Thr Ser Gln Asp Leu  Tyr Asn Gly
    1025                1030                1035

Glu Arg Gly Ala Ile Asp Leu  Glu Ala Ser Asn Asp  Ala Ile Lys
    1040                1045                1050

Asn Val Thr Phe Thr Asn Ile  Asp Ile Ile Asn Ala  Gln Arg Asp
    1055                1060                1065

Gly Val Gln Ile Gly Tyr Gly  Gly Phe Glu Asn  Ile Val Phe
    1070                1075                1080

Asn Asn Ile Thr Ile Asp Gly  Thr Gly Arg Asp Gly  Ile Ser Thr
    1085                1090                1095

Ser Arg Phe Ser Gly Pro His  Leu Gly Ala Ala Ile  Tyr Thr Tyr
    1100                1105                1110

Thr Gly Asn Gly Ser Ala Thr  Phe Asn Asn Leu Val  Thr Arg Asn
```

Ile Ala Tyr Ala Gly Gly Asn Tyr Ile Gln Ser Gly Phe Asn Leu
1130               1135                 1140

Thr Ile Lys
1145

<210> SEQ ID NO 13
<211> LENGTH: 3640
<212> TYPE: DNA
<213> ORGANISM: Paenibacillus humicus

<400> SEQUENCE: 13

| | | | | | |
|---|---|---|---|---|---|
| aaaggaggat | cgccaaccaa | tcatcccagc | aaagaaggtg | atggcagccc | aagaattgaa | 60 |
| agcgctttga | atttggaata | tacggatttg | gccgacctgc | tgattcagtc | gtattcaagc | 120 |
| gattatgccg | cgaaccaatc | gaacccgagg | aggactataa | tgcgtatccg | cactaaatat | 180 |
| atgaactgga | tgttggtgct | cgtcctgatc | gccgccggct | tcttccaggc | tgccggcccc | 240 |
| atcgctcccg | ccaccgctgc | aggaggcgcg | aatctgacgc | tcggcaaaac | cgtcaccgcc | 300 |
| agcggccagt | cgcagacgta | cagccccgac | aatgtcaagg | acagcaatca | gggaacttac | 360 |
| tgggaaagca | cgaacaacgc | cttcccgcag | tggatccaag | tcgaccttgg | cgccagcacg | 420 |
| agcatcgacc | agatcgtgct | caagcttccg | tccggatggg | agactcgtac | gcaaacgctc | 480 |
| tcgatacagg | gcagcgcgaa | cggctcgacg | ttcacgaaca | tcgtcggatc | ggccgggtat | 540 |
| acattcaatc | catccgtcgc | cggcaacagc | gtcacgatca | acttcagcgc | tgccagcgcc | 600 |
| cgctacgtcc | gcctgaattt | cacggccaat | acgggctggc | cagcaggcca | gctgtcggag | 660 |
| cttgagatct | acggagcgac | ggcgccaacg | cctactccca | cgcctactcc | aacaccaacg | 720 |
| ccaacgccaa | caccaacgcc | aaccccctaca | gtaaccccctg | cgccttcggc | cacgccgact | 780 |
| ccgactcctc | cggcaggcag | caacatcgcc | gtagggaaat | cgattacagc | ctcttccagc | 840 |
| acgcagacct | acgtagctgc | aaatgcaaat | gacaacaata | catccaccta | ttgggaggga | 900 |
| ggaagcaacc | cgagcacgct | gactctcgat | tcggttccaa | ccagagcat | cacttccgtc | 960 |
| gtcctcaagc | tgaatccggc | ttcggaatgg | gggactcgca | cgcaaacgat | ccaagttctt | 1020 |
| ggagcggatc | agaacgccgg | ctccttcagc | aatctcgtct | ctgcccagtc | ctatacgttc | 1080 |
| aatcccgcaa | ccggcaatac | ggtgacgatt | ccggtctccg | cgacggtcaa | gcgcctccag | 1140 |
| ctgaacatta | cggcgaactc | cggcgcccct | gccggccaga | ttgccgagtt | ccaagtgttc | 1200 |
| ggcacgccag | cgcctaatcc | ggacttgacc | attaccggca | tgtcctggac | tccgtcttct | 1260 |
| ccggtcgaga | gcggcgacat | tacgctgaac | gccgtcgtca | agaacatcgg | aactgcagct | 1320 |
| gcaggcgcca | cgacggtcaa | tttctacctg | aacaacgaac | tcgccggcac | cgctccggta | 1380 |
| ggcgcgcttg | cggcaggagc | ttctgcaaat | gtatcgatca | atgcaggcgc | caaagcagcc | 1440 |
| gcaacgtatg | cggtaagcgc | caaagtcgac | gagagcaacg | ccgtcatcga | gcagaatgaa | 1500 |
| ggcaacaaca | gctactcgaa | cccgactaac | ctcgtcgtag | cgccggtgtc | cagctccgac | 1560 |
| ctcgtcgccg | tgacgtcatg | gtcgccgggc | acgccgtcgc | agggagcggc | ggtcgcattt | 1620 |
| accgtcgcgc | ttaaaaatca | gggtacgctg | gcttccgccg | gcgagcccca | tcccgtaacc | 1680 |
| gtcgttctga | aaaacgctgc | cggagcgacg | ctgcaaacct | tcacgggcac | ctacacaggt | 1740 |
| tccctggcag | caggcgcatc | cgcgaatatc | agcgtgggca | gctggacggc | agcgagcggc | 1800 |
| acctataccg | tctcgacgac | ggtagccgct | gacggcaatg | aaattccggc | caagcaaagc | 1860 |
| aacaatacga | gcagcgcgag | cctcacggtc | tactcggcgc | gcggcgccag | catgccgtac | 1920 |

-continued

```
agccgttacg acacggagga tgcggtgctc ggcggcggag ctgtcctgag aacggcgccg   1980
acgttcgatc agtcgctcat cgcttccgaa gcatcgggac agaaatacgc cgcacttccg   2040
tccaacggct ccagcctgca gtggaccgtc cgtcaaggcc agggcggtgc aggcgtcacg   2100
atgcgcttca cgatgcccga cacgagcgac ggcatgggcc agaacggctc gctcgacgtc   2160
tatgtcaacg gaaccaaagc caaaacggtg tcgctgacct cttattacag ctggcagtat   2220
ttctccggcg acatgccggc tgacgctccg ggcggcggca ggccgctctt ccgcttcgac   2280
gaagtccact tcaagctgga tacggcgttg aagccgggag acacgatccg cgtccagaag   2340
ggcggtgaca gcctggagta cggcgtcgac ttcatcgaga tcgagccgat tccggcagcg   2400
gttgcccgtc cggccaactc ggtgtccgtc accgaatacg gcgctgtcgc caatgacggc   2460
aaggatgatc tcgccgcctt caaggctgcc gtgaccgcag cggtagcggc cggaaaatcc   2520
ctctacatcc cggaaggcac cttccacctg agcagcatgt gggagatcgg ctcggccacc   2580
agcatgatcg acaacttcac ggtcacgggt gccggcatct ggtatacgaa catccagttc   2640
acgaatccca atgcatcggg cggcggcatc tccctgagaa tcaaggaaa gcttgatttc   2700
agcaacatct acatgaactc caacctgcgt tcccgttacg ggcagaacgc cgtctacaaa   2760
ggctttatgg acaatttcgg cactaattcg atcatccatg acgtctgggt cgagcatttc   2820
gaatgcggca tgtgggtcgg cgactacgcc catactcctg cgatctatgc gagcgggctc   2880
gtcgtggaaa acagccgcat ccgcaacaat cttgccgacg catcaacttc tcgcagggca   2940
acgagcaact cgaccgtccg caacagcagc atccgcaaca acggcgatga cggcctcgcc   3000
gtctggacga gcaacacgaa cggcgctccg gccggcgtga caacacctt ctcctacaac   3060
acgatcgaga caactggcg cgcggcggcc atcgccttct cggcggcag cggccacaag   3120
gctgaccaca actacatcat cgactgtgtc ggcggctccg gcatccggat gaatacggtg   3180
ttcccaggct accacttcca gaacaacacc ggcatcacct ctcggatac gacgatcatc   3240
aacagcggca ccagccagga tctgtacaac ggcgagcgcg gagcgattga tctggaagct   3300
tccaacgacg cgatcaaaaa cgtcaccttc accaacatcg acatcatcaa tgcccagcgc   3360
gacggcgttc agatcggcta tggcggcggc ttcgagaaca tcgtgttcaa caacatcacg   3420
atcgacggca ccggccgcga cgggatatcg acatcccgct ctcgggacc tcatcttggc   3480
gcagccatct atacgtacac gggcaacggc tcggcgacgt caacaacct ggtgacccgg   3540
aacatcgcct atgcaggcgg caactacatc cagagcgggt tcaacctgac gatcaaatag   3600
gctgcaaaaa aaaggaagct cctcggagct ccttttttt                          3640
```

<210> SEQ ID NO 14
<211> LENGTH: 1261
<212> TYPE: PRT
<213> ORGANISM: Paenibacillus curdlanolyticus

<400> SEQUENCE: 14

```
Met Arg Asn Lys Tyr Val Thr Trp Thr Leu Ala Leu Thr Met Leu Phe
1               5                   10                  15

Ser Ser Phe Phe Leu Ala Val Gly Pro Asn Lys Val His Ala Ala
            20                  25                  30

Gly Gly Thr Asn Leu Ala Leu Gly Lys Asn Val Thr Ala Ser Gly Gln
        35                  40                  45

Ser Gln Thr Tyr Ser Pro Asn Asn Val Lys Asp Ser Asn Gln Ser Thr
    50                  55                  60
```

```
Tyr Trp Glu Ser Thr Asn Asn Ala Phe Pro Gln Trp Ile Gln Val Asp
 65                  70                  75                  80

Leu Gly Ala Thr Thr Ser Ile Asp Gln Ile Val Leu Lys Leu Pro Ala
                 85                  90                  95

Gly Trp Gly Thr Arg Thr Gln Thr Leu Ala Val Gln Gly Ser Thr Asp
            100                 105                 110

Gly Ser Ser Phe Thr Asn Ile Val Gly Ser Ala Gly Tyr Val Phe Asn
        115                 120                 125

Pro Ala Val Ala Asn Asn Ala Val Thr Ile Asn Phe Ser Ala Ala Ser
130                 135                 140

Thr Arg Tyr Val Arg Leu Asn Val Thr Ala Asn Thr Ala Trp Pro Ala
145                 150                 155                 160

Ala Gln Leu Ser Glu Phe Glu Ile Tyr Gly Ala Gly Thr Thr Thr Thr
                165                 170                 175

Pro Pro Thr Thr Pro Ala Gly Thr Tyr Glu Ala Glu Ser Ala Ala Leu
            180                 185                 190

Ser Gly Gly Ala Lys Val Asn Thr Asp His Thr Gly Tyr Thr Gly Thr
        195                 200                 205

Gly Phe Val Asp Gly Tyr Trp Thr Gln Gly Ala Thr Thr Thr Phe Thr
210                 215                 220

Ala Asn Val Ser Ala Ala Gly Asn Tyr Asp Val Thr Leu Lys Tyr Ala
225                 230                 235                 240

Asn Ala Ser Gly Ser Ala Lys Thr Leu Ser Val Tyr Val Asn Gly Thr
                245                 250                 255

Lys Ile Arg Gln Thr Thr Leu Ala Ser Leu Ala Asn Trp Asp Thr Trp
            260                 265                 270

Gly Thr Lys Val Glu Thr Leu Ser Leu Asn Ala Gly Asn Asn Thr Ile
        275                 280                 285

Ala Tyr Lys Tyr Glu Ala Ser Asp Ser Gly Asn Val Asn Ile Asp Ser
290                 295                 300

Ile Ala Val Ala Pro Ser Thr Ser Thr Pro Val Asp Pro Glu Pro Pro
305                 310                 315                 320

Ile Thr Pro Pro Thr Gly Ser Asn Ile Ala Ile Gly Lys Ala Ile Ser
                325                 330                 335

Ala Ser Ser Asn Thr Gln Ala Phe Val Ala Ala Asn Ala Asn Asp Asn
            340                 345                 350

Asp Thr Asn Thr Tyr Trp Glu Gly Gly Ala Ala Ser Ser Thr Leu Thr
        355                 360                 365

Leu Asp Leu Gly Ala Asn Gln Asn Val Thr Ser Ile Val Leu Lys Leu
370                 375                 380

Asn Pro Ser Ser Ala Trp Ser Thr Arg Thr Gln Thr Ile Gln Val Leu
385                 390                 395                 400

Gly His Asn Gln Ser Thr Thr Phe Ser Asn Leu Val Ser Ser Gln
                405                 410                 415

Ser Tyr Thr Phe Asn Pro Ala Thr Gly Asn Ser Val Thr Ile Pro Val
            420                 425                 430

Thr Ala Thr Val Lys Arg Leu Gln Leu Ser Ile Thr Ala Asn Ser Gly
        435                 440                 445

Ser Gly Ala Gly Gln Ile Ala Glu Phe Gln Val Tyr Gly Thr Pro Ala
450                 455                 460

Pro Asn Pro Asp Leu Thr Ile Thr Gly Met Ser Trp Thr Pro Ala Ser
465                 470                 475                 480

Pro Ile Glu Thr Asp Ala Val Thr Leu Asn Ala Thr Val Lys Asn Ser
```

-continued

```
                485                 490                 495
Gly Asn Ala Asp Ala Pro Ala Thr Thr Val Asn Phe Tyr Leu Asn Asn
                500                 505                 510

Glu Leu Val Gly Ser Ser Pro Val Gly Ala Leu Ala Ala Gly Ala Ser
                515                 520                 525

Ser Thr Val Ser Leu Asn Val Gly Thr Lys Thr Ala Ala Thr Tyr Ala
            530                 535                 540

Val Ser Ala Lys Val Asp Glu Ser Asn Ser Ile Ile Glu Gln Asn Asp
545                 550                 555                 560

Ala Asn Asn Ser Tyr Thr Asn Ala Ser Ser Leu Val Val Ala Pro Val
                565                 570                 575

Ala Ser Ser Asp Leu Val Gly Ala Thr Thr Trp Thr Pro Ser Thr Pro
                580                 585                 590

Val Ala Gly Asn Ala Ile Gly Phe Met Val Asn Leu Lys Asn Gln Gly
                595                 600                 605

Thr Ile Ala Ser Ala Ser Gly Ala His Gly Ile Thr Val Val Lys
            610                 615                 620

Asn Ala Ala Gly Ala Ala Leu Gln Ser Phe Ser Gly Thr Tyr Ser Gly
625                 630                 635                 640

Ala Ile Ala Ala Gly Ala Ser Val Asn Val Thr Leu Pro Gly Thr Trp
                645                 650                 655

Thr Ala Val Asn Gly Ser Tyr Thr Val Thr Thr Val Ala Val Asp
            660                 665                 670

Ala Asn Glu Leu Thr Asn Lys Gln Gly Asn Asn Val Ser Thr Ser Asn
                675                 680                 685

Leu Val Val Tyr Ala Gln Arg Gly Ala Ser Met Pro Tyr Ser Arg Tyr
            690                 695                 700

Asp Thr Glu Asp Ala Thr Arg Gly Gly Ala Thr Leu Gln Thr Ala
705                 710                 715                 720

Pro Thr Phe Asn Gln Ala Gln Ile Ala Ser Glu Ala Ser Gly Gln Ser
                725                 730                 735

Tyr Ile Ala Leu Pro Ser Asn Gly Ser Ser Ala Gln Trp Thr Val Arg
            740                 745                 750

Gln Gly Gln Gly Gly Ala Gly Val Thr Met Arg Phe Thr Met Pro Asp
            755                 760                 765

Ser Thr Asp Gly Met Gly Leu Asn Gly Ser Leu Asp Val Tyr Val Asn
            770                 775                 780

Gly Val Lys Val Lys Thr Val Ser Leu Thr Ser Tyr Tyr Ser Trp Gln
785                 790                 795                 800

Tyr Phe Ser Gly Asp Met Pro Gly Asp Ala Pro Ser Ala Gly Arg Pro
                805                 810                 815

Leu Phe Arg Phe Asp Glu Val His Trp Lys Leu Asp Thr Pro Leu Gln
                820                 825                 830

Pro Gly Asp Thr Ile Lys Ile Gln Lys Gly Asn Gly Asp Ser Leu Glu
                835                 840                 845

Tyr Gly Ile Asp Phe Leu Glu Ile Glu Pro Val Pro Thr Ala Ile Ala
            850                 855                 860

Lys Pro Ala Asn Ser Leu Ser Val Thr Glu Tyr Gly Ala Val Ala Asn
865                 870                 875                 880

Asp Gly Gln Asp Asp Leu Ala Ala Phe Lys Ala Thr Val Thr Ala Ala
                885                 890                 895

Val Ala Ala Gly Lys Ser Val Tyr Ile Pro Ala Gly Thr Phe Asn Leu
                900                 905                 910
```

Ser Ser Met Trp Glu Ile Gly Ser Ala Asn Asn Met Ile Asn Asn Ile
        915                 920                 925

Thr Ile Thr Gly Ala Gly Tyr Trp His Thr Asn Ile Gln Phe Thr Asn
    930                 935                 940

Pro Asn Ala Ala Gly Gly Gly Ile Ser Leu Arg Ile Ser Gly Gln Leu
945                 950                 955                 960

Asp Phe Ser Asn Val Tyr Met Asn Ser Asn Leu Arg Ser Arg Tyr Gly
                965                 970                 975

Gln Asn Ala Ile Tyr Lys Gly Phe Met Asp Asn Phe Gly Thr Asn Ser
            980                 985                 990

Lys Ile His Asp Val Trp Val Glu His Phe Glu Cys Gly Met Trp Val
        995                 1000                1005

Gly Asp Tyr Ala His Thr Pro Ala Ile Tyr Ala Thr Gly Leu Val
    1010                1015                1020

Val Glu Asn Ser Arg Ile Arg Asn Asn Leu Ala Asp Gly Ile Asn
    1025                1030                1035

Tyr Ser Gln Gly Thr Ser Asn Ser Ile Val Arg Asn Ser Ser Ile
    1040                1045                1050

Arg Asn Asn Gly Asp Asp Gly Leu Ala Val Trp Thr Ser Asn Thr
    1055                1060                1065

Asn Gly Ala Pro Ala Gly Val Asn Asn Thr Phe Ser Tyr Asn Thr
    1070                1075                1080

Ile Glu Asn Asn Trp Arg Ala Gly Gly Ile Ala Phe Phe Gly Gly
    1085                1090                1095

Gly Gly His Lys Ala Asp His Asn Leu Ile Val Asp Thr Val Gly
    1100                1105                1110

Gly Ser Gly Ile Arg Met Asn Thr Val Phe Pro Gly Tyr His Phe
    1115                1120                1125

Gln Asn Asn Thr Gly Ile Thr Phe Ser Asp Asn Thr Leu Ile Asn
    1130                1135                1140

Thr Gly Thr Ser Gln Asp Leu Tyr Asn Gly Glu Arg Gly Ala Ile
    1145                1150                1155

Asp Leu Glu Ala Ser Asn Asp Ala Ile Lys Asn Val Thr Phe Thr
    1160                1165                1170

Asn Ile Asp Ile Ile Asn Thr Gln Arg Asp Ala Ile Gln Phe Gly
    1175                1180                1185

Tyr Gly Gly Gly Phe Glu Asn Ile Val Phe Asn Asn Ile Asn Ile
    1190                1195                1200

Asn Gly Thr Gly Leu Asp Gly Val Thr Thr Ser Arg Phe Ala Gly
    1205                1210                1215

Pro His Lys Gly Ala Ala Ile Tyr Thr Tyr Thr Gly Asn Gly Ser
    1220                1225                1230

Ala Thr Phe Asn Asn Leu Thr Thr Ser Asn Val Ala Tyr Pro Gly
    1235                1240                1245

Leu Asn Phe Ile Gln Gln Gly Phe Asn Leu Val Ile Gln
    1250                1255                1260

<210> SEQ ID NO 15
<211> LENGTH: 3786
<212> TYPE: DNA
<213> ORGANISM: Paenibacillus curdlanolyticus

<400> SEQUENCE: 15
atgcgcaaca agtatgtcac atggacgctc gccctgacga tgctatttc gagcttcttc      60

```
cttgcagtag gtcccaacaa ggtcgttcac gcagcaggcg gaacgaattt agcgctcggc    120
aaaaacgtta cggcaagcgg ccaatcgcaa acgtatagtc ccaacaatgt aaaagacagc    180
aatcaatcga cgtactggga aagcacgaac aatgcattcc cgcaatggat tcaagtagac    240
ttaggcgcaa cgacgagcat tgaccaaatc gtactgaagc tgcccgctgg atggggtacg    300
cgtacgcaaa cgttagctgt tcaaggaagc acggacggtt cctcgttcac gaatatcgtg    360
ggctccgcag gctatgtatt taatcctgct gttgccaata acgccgttac gattaacttc    420
tctgctgcaa gcacgcgtta tgttcgtctg aacgtaacag cgaacacggc ttggccagca    480
gcgcagctgt ccgaattcga gatttatggc gctggcggca cgacgacgcc tccaacaacg    540
ccagcaggca catatgaagc tgaatccgca gcattgtccg gcggtgcgaa agtgaacacg    600
gatcataccg gctacacggg tacgggcttt gttgacggct actggacaca aggcgcgaca    660
acgacgttca cggctaacgt gtccgcagct ggcaactatg acgttacatt gaaatatgcc    720
aacgcaagcg gcagtgccaa gacgctaagc gtttacgtca acggcacgaa gattcgccag    780
acgacgctgg caagcctggc aaactgggac acttggggca cgaaggttga cgcgctgagc    840
ttgaatgccg gcaataatac gattgcatac aagtatgagg ctagcgactc gggcaacgtg    900
aatatcgact ccattgccgt ggcgccatcg acttcgacac cggtagatcc agaaccgccg    960
atcacgccgc caacgggcag caatatcgca atcggcaaag cgatcagcgc atcttcgaat    1020
acgcaagcat tcgtagctgc caacgcgaac gataacgata cgaacacgta ctgggaaggc    1080
ggagctgcat cgagcacgct gacgctggat cttggcgcga accaaaatgt aacctcgatc    1140
gtgctgaagc tgaatccttc ttcggcatgg agcacgcgta cgcaaacgat ccaagtgctt    1200
ggccacaacc aaagcacgac gacgttcagc aatctggtat cttcgcaatc gtatacgttc    1260
aatcctgcaa cgggcaactc cgtgacgatt ccggttacgg caacagttaa gcgcttgcag    1320
ctgagcatta cggcgaactc gggttccggc gctggtcaaa ttgcggaatt ccaagtgtat    1380
ggaacgccgg caccaaaccc agacctgacg atcacaggca tgtcctggac gcctgcttcg    1440
ccaattgaaa cggatgcagt tacgctgaat gcaacggtta aaaacagcgg aaatgcagac    1500
gctcctgcaa cgacggtaaa cttctacctg aacaatgagc tcgtaggctc ctcgccagtt    1560
ggcgcacttg ctgcaggcgc ttcctcgacg gtttcgctga atgttggtac gaaaacggct    1620
gcaacttatg cagttagcgc gaaagtcgat gagagcaatt cgattatcga gcaaaatgat    1680
gcgaacaaca gttatacgaa cgcatcctcg ctcgtcgtcg ctcctgtcgc aagctctgac    1740
ttggttggcg cgacgacgtg gacgcctagc acgccggttg ccggcaatgc aattggcttc    1800
atggtaaatc ttaaaaacca aggaacgatt gcatctgcaa gcggcgcgca tggcattaca    1860
gttgtcgtga aaaatgccgc aggcgctgcg ctccaatcgt tcagcggcac ctacagcgga    1920
gcaatcgcag ctggcgcatc cgttaacgta accctgccag gtacgtggac ggctgtgaat    1980
ggcagctaca cggtaacgac aacggttgct gtcgatgcta acgagctgac gaacaaacaa    2040
gggaacaacg taagcacttc gaacctcgtt gtttatgcac aacgtggcgc aagcatgcct    2100
tacagccgtt atgacacgga agacgctaca cgtggcggcg gtgcaacgct gcaaaccgca    2160
ccaaccttca accaagcgca aatcgcttcg gaagcatccg gacaaagcta tatcgcgctg    2220
ccttcgaacg gctcctccgc acaatggacg gtccgtcaag gacaaggcgg agctggcgtt    2280
acgatgcgct tcacgatgcc ggattcgact gacggtatgg gtttgaacgg ttcgctcgac    2340
gtttatgtca acggcgttaa agtaaaaacg gtatcgctca cgtcctacta cagctggcag    2400
```

-continued

```
tatttctcgg gcgatatgcc tggcgatgcg ccgtccgctg gccgtccgtt gttccgcttt    2460
gacgaagtac actggaagct tgacacgcct cttcaaccag gcgacacgat caaaatccaa    2520
aaaggcaacg gagatagcct ggaatacggc attgacttcc tcgaaatcga gccggttcca    2580
acagcaatcg ctaaacctgc caactcgctt tccgttacgg agtatggcgc tgtagcaaac    2640
gatggccaag acgaccttgc cgcattcaaa gcaacggtta cggctgcagt tgctgctggc    2700
aaatccgttt acattcctgc tggcacgttc aatctgagca gcatgtggga atcggatcg    2760 gctaacaaca tgatcaacaa cattacgatt acaggcgcag gctactggca tacgaacatt    2820
caattcacga atccgaatgc agcaggcggc ggcatttcgc tccggatttc cggacagctt    2880
gatttcagca atgtttacat gaactccaac ctgcgttcgc gttatggtca aaatgcgatt    2940
tacaaaggct tcatggacaa cttcggcaca aactccaaaa tccatgacgt atgggttgag    3000
cacttcgagt gcggcatgtg ggtaggcgat tacgcgcata cgccagcgat ctatgcaacg    3060
ggtcttgtcg ttgaaaacag ccggattcgc aacaaccttg cagacggcat caactactcg    3120
caaggcacga gcaattcgat cgtacgcaac agcagtatcc gcaataacgg tgatgacggt    3180
ctggcggttt ggacgagtaa cacgaatggc gcgccagcag gcgtgaacaa cacgttctcg    3240
tacaacacga tcgaaaacaa ctggcgtgca ggcggtatcc cattcttcgg cggcggcggc    3300
cacaaggctg accacaacct gatcgttgat acggttggcg gctccggcat ccggatgaac    3360
acggtattcc caggctacca cttccaaaac aacacgggta ttacgttctc cgacaacacg    3420
ctgatcaaca caggcacaag ccaagatttg tacaacggcg agcgcggtgc gatcgatctc    3480
gaagcatcga acgatgcaat caagaacgtc acgttcacga acatcgacat catcaacacc    3540
cagcgcgatg cgatacaatt cggctacggc ggcggattcg agaacatcgt atttaacaac    3600
attaacatta acgtacgggg cttgacggc gttacaacct cacggtttgc tggaccgcat    3660
aaaggtgctg caatctacac gtacacgggc aatggctctg caacgttcaa taacctgacg    3720
acgagcaacg tggcatatcc aggcttgaat ttcattcagc aaggctttaa tctggtgatc    3780
cagtag                                                                3786
```

<210> SEQ ID NO 16
<211> LENGTH: 1291
<212> TYPE: PRT
<213> ORGANISM: Paenibacillus sp. strain RM1

<400> SEQUENCE: 16

Met Arg Cys Lys Phe Val Ala Trp Ser Leu Val Thr Ala Met Leu Met
1               5                   10                  15

Ala Ser Leu Leu Thr Ala Val Gly Pro Phe Gly Pro Ala Ser Ala Ala
                20                  25                  30

Gly Gly Pro Asn Leu Thr Pro Gly Lys Pro Ile Thr Ala Ser Gly Gln
            35                  40                  45

Ser Gln Thr Tyr Ser Pro Gln Asn Val Lys Asp Gly Asn Gln Asn Thr
        50                  55                  60

Tyr Trp Glu Ser Thr Asn Asn Ala Phe Pro Gln Trp Ile Gln Val Asp
65                  70                  75                  80

Leu Gly Ala Ser Thr Gly Ile Asp Gln Ile Val Leu Lys Leu Pro Ala
                85                  90                  95

Ser Trp Glu Ala Arg Thr Gln Thr Leu Ala Val Gln Gly Ser Leu Asn
                100                 105                 110

Gly Ser Thr Phe Thr Asp Ile Val Gly Ser Ala Asn Tyr Val Phe Ser
            115                 120                 125

```
Pro Ser Val Gly Asn Asn Thr Val Thr Ile Asn Phe Thr Ala Thr Ser
    130                 135                 140

Thr Arg Tyr Val Arg Leu Tyr Val Thr Ala Asn Thr Gly Trp Pro Ala
145                 150                 155                 160

Ala Gln Leu Ser Glu Phe Glu Ile Tyr Gly Ser Gly Asp Gln Thr Pro
                165                 170                 175

Ala Pro Asp Thr Tyr Gln Ala Glu Ser Ala Ala Leu Ser Gly Gly Ala
            180                 185                 190

Lys Val Asn Thr Asp His Ala Gly Tyr Ile Gly Thr Gly Phe Val Asp
        195                 200                 205

Gly Tyr Trp Thr Gln Gly Ala Thr Thr Thr Phe Ser Val Asn Ala Pro
210                 215                 220

Thr Ala Gly Asn Tyr Asp Val Thr Leu Arg Tyr Gly Asn Ala Thr Gly
225                 230                 235                 240

Ser Asn Lys Thr Val Ser Leu Tyr Val Asn Gly Ala Lys Ile Arg Gln
                245                 250                 255

Thr Thr Leu Pro Ser Leu Pro Asn Trp Asp Ser Trp Ser Ser Lys Thr
            260                 265                 270

Glu Thr Leu Asn Leu Asn Ala Gly Ser Asn Thr Ile Ala Tyr Lys Tyr
        275                 280                 285

Asp Pro Gly Asp Ser Gly Asn Val Asn Leu Asp Gln Ile Thr Val Glu
    290                 295                 300

Ala Ser Thr Ser Thr Pro Thr Pro Thr Pro Ser Pro Thr Pro Thr Pro
305                 310                 315                 320

Thr Pro Thr Pro Thr Pro Thr Pro Thr Pro Thr Pro Thr Pro Thr Pro
                325                 330                 335

Thr Pro Thr Pro Thr Pro Thr Pro Thr Pro Thr Pro Thr Pro Thr Pro
            340                 345                 350

Pro Pro Gly Gly Asn Ile Ala Ile Gly Lys Ser Ile Ser Ala Ser Ser
        355                 360                 365

His Thr Gln Thr Tyr Val Ala Glu Asn Ala Asn Asp Asn Asp Val Asn
370                 375                 380

Thr Tyr Trp Glu Gly Gly Gly Asn Pro Ser Thr Leu Thr Leu Asp Leu
385                 390                 395                 400

Gly Ala Asn Tyr Asn Ile Thr Ser Ile Val Leu Lys Leu Asn Pro Ser
                405                 410                 415

Ser Ile Trp Ala Ala Arg Thr Gln Thr Ile Gln Val Leu Gly His Asp
            420                 425                 430

Gln Asn Thr Thr Thr Phe Ser Asn Leu Val Ser Ala Lys Ser Tyr Ser
        435                 440                 445

Phe Asp Pro Ala Ser Gly Asn Thr Val Thr Ile Pro Val Thr Ala Thr
    450                 455                 460

Val Lys Arg Leu Gln Leu Asn Ile Thr Ser Asn Ser Gly Ala Pro Ala
465                 470                 475                 480

Gly Gln Val Ala Glu Phe Gln Val Phe Gly Thr Ala Pro Asn Pro
                485                 490                 495

Asp Leu Thr Ile Thr Gly Met Ser Trp Ser Pro Ser Pro Val Glu
            500                 505                 510

Thr Asp Ala Ile Thr Leu Asn Ala Thr Val Lys Asn Asn Gly Asn Ala
        515                 520                 525

Ser Ala Ala Ala Thr Thr Val Asn Phe Tyr Leu Asn Asn Glu Leu Ala
    530                 535                 540
```

```
Gly Ser Ala Pro Val Ala Ala Leu Ala Ala Gly Ser Ala Thr Val
545                 550                 555                 560

Pro Leu Asn Val Gly Ala Lys Thr Ala Ala Thr Tyr Ala Val Gly Ala
                565                 570                 575

Lys Val Asp Glu Ser Asn Ala Val Ile Glu Leu Asn Glu Ser Asn Asn
            580                 585                 590

Ser Tyr Thr Asn Pro Ala Ser Leu Val Val Ala Pro Val Ser Ser Ser
        595                 600                 605

Asp Leu Val Gly Thr Val Ser Trp Thr Pro Ser Thr Pro Ile Ala Asn
    610                 615                 620

Asn Ala Val Ser Phe Asn Val Asn Leu Lys Asn Gln Gly Thr Ile Ala
625                 630                 635                 640

Ser Ala Gly Gly Ser His Gly Val Thr Val Leu Lys Asn Ala Ser
                645                 650                 655

Gly Ser Thr Val Gln Thr Phe Ser Gly Ser Tyr Thr Gly Ser Leu Ala
                660                 665                 670

Pro Gly Ala Ser Val Asn Ile Thr Leu Pro Gly Trp Leu Thr Ala Ala
                675                 680                 685

Ala Gly Ser Tyr Thr Val Thr Ala Thr Val Ala Ala Asp Ala Asn Glu
            690                 695                 700

Leu Pro Ile Lys Gln Ala Asn Asn Ala Asn Thr Ala Ser Leu Thr Val
705                 710                 715                 720

Tyr Ser Ala Arg Gly Ala Ser Met Pro Tyr Ser Arg Tyr Asp Thr Glu
                725                 730                 735

Asp Ala Thr Leu Gly Gly Gly Ala Thr Leu Lys Ser Ala Pro Thr Phe
            740                 745                 750

Asp Gln Ala Leu Thr Ala Ser Glu Ala Thr Gly Gln Leu Tyr Ala Ala
            755                 760                 765

Leu Pro Ser Asn Gly Ser Tyr Leu Gln Trp Thr Val Arg Gln Gly Gln
770                 775                 780

Gly Gly Ala Gly Val Thr Met Arg Phe Thr Met Pro Asp Ser Ala Asp
785                 790                 795                 800

Gly Met Gly Leu Asn Gly Ser Leu Asp Val Tyr Val Asn Gly Thr Lys
                805                 810                 815

Val Lys Thr Val Ser Leu Thr Ser Tyr Tyr Ser Trp Gln Tyr Phe Ser
            820                 825                 830

Gly Asp Met Pro Gly Asp Ala Pro Ser Ala Gly Arg Pro Leu Phe Arg
                835                 840                 845

Phe Asp Glu Val His Trp Lys Leu Asp Thr Pro Leu Lys Pro Gly Asp
850                 855                 860

Thr Ile Arg Ile Gln Lys Asn Asn Gly Asp Ser Leu Glu Tyr Gly Val
865                 870                 875                 880

Asp Phe Ile Glu Ile Glu Pro Val Pro Ala Ala Ile Ser Arg Pro Ala
                885                 890                 895

Asn Ser Val Ser Val Thr Asp Tyr Gly Ala Val Pro Asn Asp Gly Gln
                900                 905                 910

Asp Asp Leu Thr Ala Phe Lys Ala Ala Val Asn Ala Ala Val Ala Ser
            915                 920                 925

Asp Lys Ile Leu Tyr Ile Pro Glu Gly Thr Phe His Leu Gly Asn Met
            930                 935                 940

Trp Glu Ile Gly Ser Val Ser Asn Met Ile Asp His Ile Thr Ile Thr
945                 950                 955                 960

Gly Ala Gly Ile Trp Tyr Thr Asn Ile Gln Phe Thr Asn Ala Asn Pro
```

|   |   | 965 |   |   |   | 970 |   |   |   | 975 |   |   |
|---|---|---|---|---|---|---|---|---|---|---|---|---|

Ala Ser Gly Gly Ile Ser Leu Arg Ile Thr Gly Lys Leu Asp Phe Ser
            980                 985                 990

Asn Val Tyr Leu Asn Ser Asn Leu Arg Ser Arg Tyr Gly Gln Asn Ala
            995                 1000                1005

Val Tyr Lys Gly Phe Met Asp Asn Phe Gly Thr Asn Ser Val Ile
    1010                1015                1020

Arg Asp Trp Ile Val Glu His Phe Glu Cys Gly Phe Trp Val Gly
    1025                1030                1035

Asp Tyr Gly His Thr Pro Ala Ile Arg Ala Ser Gly Leu Leu Ile
    1040                1045                1050

Glu Asn Ser Arg Ile Arg Asn Asn Leu Ala Asp Gly Val Asn Phe
    1055                1060                1065

Ala Gln Gly Thr Ser Asn Ser Thr Val Arg Asn Ser Ser Leu Arg
    1070                1075                1080

Asn Asn Gly Asp Asp Ala Leu Ala Val Trp Thr Ser Asn Thr Asn
    1085                1090                1095

Gly Ala Pro Glu Gly Val Asn Asn Thr Phe Ser Tyr Asn Thr Ile
    1100                1105                1110

Glu Asn Asn Trp Arg Ala Gly Gly Ile Ala Phe Phe Gly Gly Ser
    1115                1120                1125

Gly His Lys Ala Asp His Asn Tyr Ile Val Asp Cys Val Gly Gly
    1130                1135                1140

Ser Gly Ile Arg Met Asn Thr Val Phe Pro Gly Tyr His Phe Gln
    1145                1150                1155

Asn Asn Thr Gly Ile Val Phe Ser Asp Thr Thr Ile Val Asn Cys
    1160                1165                1170

Gly Thr Ser Lys Asp Leu Tyr Asn Gly Glu Arg Gly Ala Ile Asp
    1175                1180                1185

Leu Glu Ala Ser Asn Asp Ala Ile Arg Asn Val Thr Phe Thr Asn
    1190                1195                1200

Ile Asp Ile Ile Asn Ser Gln Arg Asp Ala Ile Gln Phe Gly Tyr
    1205                1210                1215

Gly Gly Gly Phe Thr Asn Ile Val Phe Asn Asn Ile Asn Ile Asn
    1220                1225                1230

Gly Thr Gly Leu Asp Gly Val Thr Thr Ser Arg Phe Ser Gly Pro
    1235                1240                1245

His Leu Gly Ala Ala Ile Phe Thr Tyr Thr Gly Asn Gly Ser Ala
    1250                1255                1260

Thr Phe Asn Asn Leu Arg Thr Ser Asn Ile Ala Tyr Pro Asn Leu
    1265                1270                1275

Tyr Tyr Ile Gln Ser Gly Phe Asn Leu Ile Ile Asn Asn
    1280                1285                1290

<210> SEQ ID NO 17
<211> LENGTH: 5090
<212> TYPE: DNA
<213> ORGANISM: Paenibacillus sp. strain RM1

<400> SEQUENCE: 17
cccgggtacc agacctatcg ggaaaaacgc gagcggccct tcgcgcctta tgcgctacgg     60
acggtgctgg cgggcggttt gttttcatc atcattcccc tgatgatcta cacggcatcg    120
tatatcccgt ttttgctcgt gccgggtccc ggacacgggt tgaaagacgt cgtctccgcc    180

```
cagaagttca tgttcaatta tcatagccgg cttaacgcca cccacccatt ctcgtcgctg    240
tggtgggagt ggcctctcat ccgcaagccg atctggtatt acggagccgc ggaattggcg    300
ccgggaaaaa tggcgagcat cgtgggcatg gcaatccgg cggtgtggtg  gacgggaacg    360
attgcggtaa tcgcggccct tcgctcggcc tggaagaagc gggaccggag catgaccgtc    420
gtcttcgttg aatcgcctc gtcttatctt ccgtgggttt tcgtatccag actcacctt    480 atttatcact ttttcgcttg cgttccgttt ctcgttcttt gcatcgttta ttggattcga    540
aaaatggaat agcgtaagcc gggatatcgg attgcgacgc tcctttacgc aggcgcggtt    600
ctggtgctgt tcattttgtt ttacccgatt tgtcgggga ccgaaataga cgtttcttac    660
gcggaccgcg ttctgaagtg gttcggcggg tggattttc acgggtaagc gagcgttgga    720
agcaaggaag ggaaggaaga cgagcgtctc cttcccgaaa tccatccaat atcttgaaat    780
tgcatacatt tttcgtaaga ttgcttctta tctgtctccc tccctgttc ttataatggg    840 ggtatcccaa cgaaaggagg gtttgtaagc gctgtcagcs tgtttgccga aagttctcgc    900
atttgctgac ctacactttg aggaggagga atttaatgcg ctgcaaattt gtcgcatggt    960
cgcttgttac agccatgctg atggccagtt tgctgacggc tgtaggaccg ttcggccccg    1020
cttccgccgc gggaggaccg aatctgacgc cgggcaaacc cattacgcg agcggccaat    1080 cccaaaccta cagccctcag aacgtaaaag acggcaatca aaatacgtat tgggaaagca    1140
cgaacaacgc gttcccgcaa tggattcaag tggatttggg cgcaagcacg ggcatcgacc    1200
aaattgtgct gaagctgccc gcaagctggg aagcgcgcac gcaaacgctg gccgttcaag    1260
gcagcttgaa cggttcgacg ttcacggaca ttgtcggctc cgccaattat gtattcagtc    1320
cgtctgtcgg gaacaacacg gttacgatca actttaccgc gaccagcacg cgctacgtgc    1380
gcttgtatgt aacggccaac acgggctggc cggcggcgca gctgtccgaa ttcgaaattt    1440
acggctccgg cgaccagacg ccggcgcctg atacgtatca agccgaatcc gcggctctgt    1500
ccggcggcgc gaaagtcaac acggaccatg ccggatatat cggcacgggc tttgttgacg    1560
gttactggac gcaaggcgcg acgacgacct tttcggtcaa cgcgccgacg gcgggcaact    1620
acgatgtaac gctgaggtac ggcaacgcaa ccggcagcaa caaaacggta agcctctacg    1680
tcaatggagc gaagattcgc cagaccacgc tgcccagcct gcctaactgg gattcatgga    1740
gcagcaagac ggagacgctt aacctgaatg caggcagcaa caccattgcg tacaaatacg    1800
acccgggcga ttccggcaac gtcaatcttg accaaatcac ggtcgaagcg tcgacttcaa    1860
cgcctactcc tactccatcc cctactccta cacctacgcc aacgccgacg cctacgccta    1920
cgcctacacc cacacctact ccgaccccga cgcctacgcc tacacctaca cctacaccta    1980
cgccgacgcc tcctccgggc ggcaacatcg ccatcggcaa atcgatttcc gcatcctccc    2040
acacgcagac gtacgttgcg gagaacgcga acgataacga tgtcaacacg tactgggaag    2100
gcggcggcaa tccgagcacg ctgacgcgtcg atctccggagc gaactacaat attacgtcca    2160
tcgtgctgaa gctgaacccg tcctcgatat gggctgcgcg tacgcaaacg attcaagtgc    2220
tcggacacga tcagaacacg acgaccttca gcaatctggt ctcggcgaaa tcgtactcgt    2280
tcgatccggc ctccggcaat actgtgacca ttccggttac ggcgacggtg aaacgtttgc    2340
agttgaacat tacgtcgaac tccggcgccc cggccggaca agtcgccgag ttccaggtgt    2400
tcggcacgcc tgcgccgaat ccggacctga cgattaccgg catgtcctgg tcgccttctt    2460
ctccggttga gaccgacgcc attacgctaa acgcaacggt gaagaacaac gggaatgcca    2520
gcgccgcggc gaccaccgtc aatttctacc tgaacaacga gctggcgggt tccgcgccgg    2580
```

```
tagccgcgct ggcggcaggc gcttcggcaa cggtgccgct gaatgtcggc gcgaaaaccg    2640
ccgcgacata cgcggtcggc gccaaagtag acgagagcaa cgcggtcatc gagctgaacg    2700
agtcgaacaa cagctacacg aatccggctt cactcgttgt ggcccccgtt ccagctcgg     2760 atctggtggg cacggtttcg tggacgccga gcactccgat tgccaacaat gccgtttctt    2820
ttaacgtaaa tcttaaaaat caaggaacga ttgcttccgc cggcgggtct cacggcgtga    2880
cggtcgtgct taaaaatgct tccggttcga ccgttcaaac gttcagcggt tcctataccg    2940
gcagcctggc tccgggagcg tccgtcaaca tcacccttcc ggggacctgg acggcggcag    3000
ccggcagcta cacggtaacg gccaccgttg cggcagacgc caacgaactt ccgatcaagc    3060
aagccaacaa cgcgaacacc gcaagcctga ccgtatattc cgcccgcggc gcgagcatgc    3120
cgtacagccg gtatgacacc gaggacgcca ccctcggcgg cggcgccacg ctgaagtccg    3180
cgccgacatt cgatcaggcg cttacggcat cggaagccac cggccaactc tatgcggcgc    3240
tgccctcgaa cggctcctat cttcaatgga ccgtcagaca gggtcagggc ggcgcaggcg    3300
tgacgatgag atttacgatg cccgactcgg cggacggcat gggattaaac ggttcgctag    3360
acgtttacgt caacggcacc aaagtcaaaa ccgtatcgct gacctcctac tacagctggc    3420
agtatttctc gggcgatatg cccggagacg ctcccagcgc gggccgtccg ctcttccgct    3480
ttgacgaagt gcactggaag ctggatactc cgctcaaacc cggagacacg attcgcatcc    3540
agaagaacaa cggcgacagc ctggaatacg gtgtcgactt tattgaaatc gaaccggttc    3600
cggctgcgat ctcccgtccg gccaactcgg tttccgtaac ggattacggc gctgtgccga    3660
acgacggaca ggacgatctc accgcccttta aagccgccgt aaacgcggcg gtcgcatccg    3720
acaagatctt gtacattccg gaaggaacgt tccacctcgg caacatgtgg gagatcggtt    3780
ccgtcagcaa catgatcgat cacattacga ttacgggagc cggtatctgg tatacgaaca    3840
tccagtttac caacgccaat ccggcgtccg gcggcatctc gctccggatt acgggcaagc    3900
ttgatttcag caacgtgtac ctcaactcca atttgcggtc gcggtatggt caaaatgcgg    3960
tttacaaagg ctttatggac aacttcggga ccaattccgt catccgcgac gtctgggtcg    4020
agcacttcga atgcggcttc tgggtcgggg actacgggca tacgccggcg atccgcgcga    4080
gcgggctgct gattgaaaac agccgaatcc gcaacaacct ggccgatggc gtcaacttcg    4140
cccaagggac cagcaattcg accgtacgca acagcagcct gcgcaacaac ggcgacgacg    4200
cccttgccgt atggacgagt aatacgaacg gcgcgcccga aggcgtaaac aataccttct    4260
cgtacaacac catcgaaaac aactggcgcg cgggaggcat cgccttcttc ggaggaagcg    4320
gacacaaggc cgaccacaac tacatcgtcg actgcgtcgg cggttccggc atccggatga    4380
acaccgtgtt ccccggatac cacttccaga caataccgg cattgtgttc tcggacacga    4440
ccatcgtcaa ctgcggcacg agcaaagacc tatacaacgg cgaacgcggc gccatcgatc    4500
tggaagcttc gaacgacgcc atccggaacg tgacgtttac caacatcgat attatcaact    4560
ctcagcgcga tgcgatccag ttcggttacg gcggcggctt caccaacatc gtgttcaaca    4620
acatcaacat taacggaacc ggtcttgacg gcgtaaccac ctcgcggttc tcgggaccgc    4680
atctgggcgc ggcgatcttc acctataccg gcaacggctc cgccacgttc aacaatctga    4740
ggaccagcaa tatcgcttac cccaatctgt attacatcca gagcgggttc aatctgatca    4800
tcaataatta gatatctggg cccgtctgcg ggggaggaac tcttcggagc tcgaattcgt    4860
aatcatggtc atagctgttt cctgtgtgaa attgttatcc gctcacaatt ccacacaaca    4920
```

```
tacgagccgg aagcataaag tgtaaagcct ggggtgccta atgagtgagc taactcacat    4980
taattgcgtt gcgctcactg cccgctttcc agtcgggaaa ctgtcgtgcc agctgcatta    5040
atgaatcggc caacgcgcgg ggagaggcsg tttkcgtatt gggcgccctt               5090
```

<210> SEQ ID NO 18
<211> LENGTH: 635
<212> TYPE: PRT
<213> ORGANISM: Trichoderma harzianum

<400> SEQUENCE: 18

```
Met Leu Gly Val Phe Arg Arg Leu Arg Leu Gly Ala Leu Ala Ala
1               5                   10                  15

Ala Leu Ser Ser Leu Gly Ser Ala Ala Pro Ala Asn Val Ala Ile Arg
            20                  25                  30

Ser Leu Glu Glu Arg Ala Ser Ala Asp Arg Leu Val Phe Cys His
        35                  40                  45

Phe Met Ile Gly Ile Val Gly Asp Arg Gly Ser Ser Ala Asp Tyr Asp
    50                  55                  60

Asp Asp Met Gln Arg Ala Lys Ala Ala Gly Ile Asp Ala Phe Ala Leu
65                  70                  75                  80

Asn Ile Gly Val Asp Gly Tyr Thr Asp Gln Gln Leu Gly Tyr Ala Tyr
                85                  90                  95

Asp Ser Ala Asp Arg Asn Gly Met Lys Val Phe Ile Ser Phe Asp Phe
            100                 105                 110

Asn Trp Trp Ser Pro Gly Asn Ala Val Gly Val Gly Gln Lys Ile Ala
        115                 120                 125

Gln Tyr Ala Asn Arg Pro Ala Gln Leu Tyr Val Asp Asn Arg Pro Phe
    130                 135                 140

Ala Ser Ser Phe Ala Gly Asp Gly Leu Asp Val Asn Ala Leu Arg Ser
145                 150                 155                 160

Ala Ala Gly Ser Asn Val Tyr Phe Val Pro Asn Phe His Pro Gly Gln
                165                 170                 175

Ser Ser Pro Ser Asn Ile Asp Gly Ala Leu Asn Trp Met Ala Trp Asp
            180                 185                 190

Asn Asp Gly Asn Asn Lys Ala Pro Lys Pro Gly Gln Thr Val Thr Val
        195                 200                 205

Ala Asp Gly Asp Asn Ala Tyr Lys Asn Trp Leu Gly Gly Lys Pro Tyr
    210                 215                 220

Leu Ala Pro Val Ser Thr Trp Val Phe Asn His Phe Gly Pro Glu Val
225                 230                 235                 240

Ser Tyr Ser Lys Asn Trp Val Phe Pro Ser Gly Pro Leu Ile Tyr Asn
                245                 250                 255

Arg Trp Gln Gln Val Leu Gln Gln Gly Phe Pro Arg Val Glu Ile Val
            260                 265                 270

Thr Trp Asn Asp Tyr Gly Glu Ser His Tyr Val Gly Pro Leu Lys Ser
        275                 280                 285

Lys Gln Phe His Asp Gly Asn Ser Lys Trp Val Asn Asp Met Pro His
    290                 295                 300

Asp Gly Phe Leu Asp Leu Ser Lys Pro Phe Ile Ala Tyr Lys Asn
305                 310                 315                 320

Arg Asp Thr Asp Ile Ser Lys Tyr Val Gln Asn Glu Gln Leu Val Tyr
                325                 330                 335

Trp Tyr Arg Arg Asn Leu Lys Ala Leu Asp Cys Asp Ala Thr Asp Thr
            340                 345                 350
```

```
Thr Ser Asn Arg Pro Ala Asn Gly Ser Gly Asn Tyr Phe Glu Gly
        355                 360                 365

Arg Pro Asp Gly Trp Gln Thr Met Asp Asp Thr Val Tyr Val Ala Ala
    370                 375                 380

Leu Leu Lys Thr Ala Gly Ser Val Thr Val Thr Ser Gly Gly Thr Thr
385                 390                 395                 400

Gln Thr Phe Gln Ala Asn Ala Gly Ala Asn Leu Phe Gln Ile Pro Ala
                405                 410                 415

Ser Ile Gly Gln Gln Lys Phe Ala Leu Thr Arg Asn Gly Gln Thr Val
                420                 425                 430

Phe Ser Gly Thr Ser Leu Met Asp Ile Thr Asn Val Cys Ser Cys Gly
                435                 440                 445

Ile Tyr Asn Phe Asn Pro Tyr Val Gly Thr Ile Pro Ala Gly Phe Asp
            450                 455                 460

Asp Pro Leu Gln Ala Asp Gly Leu Phe Ser Leu Thr Ile Gly Leu His
465                 470                 475                 480

Val Thr Thr Cys Gln Ala Lys Pro Ser Leu Gly Thr Asn Pro Pro Val
                485                 490                 495

Thr Ser Gly Pro Val Ser Ser Leu Pro Ala Ser Ser Thr Thr Arg Ala
            500                 505                 510

Ser Ser Pro Pro Pro Val Ser Ser Thr Arg Val Ser Ser Pro Pro Val
        515                 520                 525

Ser Ser Pro Pro Val Ser Arg Thr Ser Ser Ala Pro Pro Pro Gly
        530                 535                 540

Asn Ser Thr Pro Pro Ser Gly Gln Val Cys Val Ala Gly Thr Val Ala
545                 550                 555                 560

Asp Gly Glu Ser Gly Asn Tyr Ile Gly Leu Cys Gln Phe Ser Cys Asn
                565                 570                 575

Tyr Gly Tyr Cys Pro Pro Gly Pro Cys Lys Cys Thr Ala Phe Gly Ala
            580                 585                 590

Pro Ile Ser Pro Pro Ala Ser Asn Gly Arg Asn Gly Cys Pro Leu Pro
        595                 600                 605

Gly Glu Gly Asp Gly Tyr Leu Gly Leu Cys Ser Phe Ser Cys Asn His
    610                 615                 620

Asn Tyr Cys Pro Pro Thr Ala Cys Gln Tyr Cys
625                 630                 635

<210> SEQ ID NO 19
<211> LENGTH: 2041
<212> TYPE: DNA
<213> ORGANISM: Trichoderma harzianum

<400> SEQUENCE: 19
atgttgggcg ttttccgccg cctcaggctc ggcgcccttg ccgccgcagc tctgtcttct      60
ctcggcagtg ccgctcccgc caatgttgct attcggtctc tcgaggaacg tgcttcttct     120
gctgaccgtc tcgtattctg tcatttcatg attgggatcg tgggtgaccg tggcagctcg     180
gcagattatg atgacgatat gcaacgtgcc aaagccgctg gcattgacgc cttcgccctg     240
aacatcggcg ttgacggcta taccgaccag cagctcggct atgcctatga ctctgccgat     300
cgtaatggca tgaaagtctt catttcattt gatttcaact ggtggagccc cggcaatgca     360
gttggtgttg ccagaagat tgcgcagtat gccaaccgcc ctgcccagct gtatgtcgac      420
aaccggccat tcgcctcttc cttcgccggt gacggtctgg atgtaaatgc gttgcgctct    480
```

```
gctgcaggct ccaacgttta ctttgtgccc aacttccacc ctggtcaatc ttccccctcc    540
aacattgatg gcgcccttaa ctggatggcc tgggataatg atggaaacaa caaggcaccc    600
aagccgggcc agactgtcac agtggcagac ggtgacaacg cttataagaa ttggttgggt    660
ggcaagcctt acctggcgcc tgtctcaact tgggttttca accatttcgg gcccgaagtt    720
tcatattcca agaactgggt tttcccaagt gggcctctga tctataaccg gtggcaacaa    780
gtcttgcagc aagggttccc aagggttgag atcgttacct ggaatgacta cggggaatct    840
cactacgtcg gtcccctgaa gtctaagcaa tttcatgatg gaactccaa atgggtcaat     900 gatatgcccc acgatggatt cctggatctt tcgaagccgt tcatagccgc atataaaaac    960
agggataccg acatctccaa gtatgttcaa atgagcagc ttgtttactg gtaccgccgc    1020
aacttaaagg cactggactg tgacgccacc gacacaacct ctaaccgccc ggctaacaat    1080
ggaagcggca attactttga gggacgcccc gatggttggc aaactatgga tgatacggtt    1140
tacgtggcgg cacttctcaa gactgccggt agcgtcacgg tcacgtctgg tggcaccact    1200
caaacgttcc aggccaacgc cggagccaat ctcttccaaa tcccggccag catcggccag    1260
caaaagtttg ctctgactcg taacggtcag accgtctta gcggaacctc attgatggat     1320
atcaccaacg tttgctcttg cggtatctac aacttcaacc catatgttgg caccattcct    1380
gccggctttg acgaccctct tcaggctgac ggtctttct ctttgaccat cggattgcac     1440
gtcacaactt gtcaggccaa gcatctctt ggaactaacc ctcctgtcac ttccggccct     1500
gtgtcctcgc ttccagcttc ctccaccacc cgcgcatcct cgccgcctcc tgtttcttca    1560
actcgtgtct cttctccccc tgtctcttcc cctccagttt ctcgcacctc ttctgccct     1620 cccctccgg gcaacagcac gccgccatcg ggtcaggttt gcgttgccgg caccgttgcc    1680
gacggcgagt ctggcaacta catcggcctg tgccaattca gctgcaacta cggttactgc    1740
ccaccaggac cgtgtaagtg caccgccttt ggtgctccca tctcgccacc ggcatccaac   1800
ggccgcaacg gctgccctct gccgggagaa ggcgatggtt atctgggcct gtgcagtttc   1860
agttgtaacc ataattactg cccgccaacg gcatgtcaat actgctagga gggatcaatc   1920
tcagtatgag tatatggagg ctgctgaagg accaattagc tgttcttatc ggcagacgaa    1980
acccatagag taagaagtta aataaaatgc aattaatgtg ttttcaaaaa aaaaaaaaa    2040 a                                                                   2041
```

<210> SEQ ID NO 20
<211> LENGTH: 635
<212> TYPE: PRT
<213> ORGANISM: Trichoderma harzianum

<400> SEQUENCE: 20

```
Met Leu Gly Val Phe Arg Arg Leu Arg Leu Gly Ala Leu Ala Ala Ala
1               5                   10                  15

Ala Leu Ser Ser Leu Gly Ser Ala Ala Pro Ala Asn Val Ala Ile Arg
            20                  25                  30

Ser Leu Glu Glu Arg Ala Ser Ser Ala Asp Arg Leu Val Phe Cys His
        35                  40                  45

Phe Met Ile Gly Ile Val Gly Asp Arg Gly Ser Ala Asp Tyr Asp
    50                  55                  60

Asp Asp Met Gln Arg Ala Lys Ala Ala Gly Ile Asp Ala Phe Ala Leu
65                  70                  75                  80

Asn Ile Gly Val Asp Gly Tyr Thr Asp Gln Gln Leu Gly Tyr Ala Tyr
                85                  90                  95
```

```
Asp Ser Ala Asp Arg Asn Gly Met Lys Val Phe Ile Ser Phe Asp Phe
            100                 105                 110

Asn Trp Trp Ser Pro Gly Asn Ala Val Gly Val Gly Gln Lys Ile Ala
            115                 120                 125

Gln Tyr Ala Asn Arg Pro Ala Gln Leu Tyr Val Asp Asn Arg Pro Phe
            130                 135                 140

Ala Ser Ser Phe Ala Gly Asp Gly Leu Asp Val Asn Ala Leu Arg Ser
145                 150                 155                 160

Ala Ala Gly Ser Asn Val Tyr Phe Val Pro Asn Phe His Pro Gly Gln
            165                 170                 175

Ser Ser Pro Ser Asn Ile Asp Gly Ala Leu Asn Trp Met Ala Trp Asp
            180                 185                 190

Asn Asp Gly Asn Asn Lys Ala Pro Lys Pro Gly Gln Thr Val Thr Val
            195                 200                 205

Ala Asp Gly Asp Asn Ala Tyr Lys Asn Trp Leu Gly Gly Lys Pro Tyr
            210                 215                 220

Leu Ala Pro Val Ser Thr Trp Val Phe Asn His Phe Gly Pro Glu Val
225                 230                 235                 240

Ser Tyr Ser Lys Asn Trp Val Phe Pro Ser Gly Pro Leu Ile Tyr Asn
            245                 250                 255

Arg Trp Gln Gln Val Leu Gln Gln Gly Phe Pro Arg Val Glu Ile Val
            260                 265                 270

Thr Trp Asn Asp Tyr Gly Glu Ser His Tyr Val Gly Pro Leu Lys Ser
            275                 280                 285

Lys Gln Phe His Asp Gly Asn Ser Lys Trp Val Asn Asp Met Pro His
            290                 295                 300

Asp Gly Phe Leu Asp Leu Ser Lys Pro Phe Ile Ala Ala Tyr Lys Asn
305                 310                 315                 320

Arg Asp Thr Asp Ile Ser Lys Tyr Val Gln Asn Glu Gln Leu Val Tyr
            325                 330                 335

Trp Tyr Arg Arg Asn Leu Lys Ala Leu Asp Cys Asp Ala Thr Asp Thr
            340                 345                 350

Thr Ser Asn Arg Pro Ala Asn Asn Gly Ser Gly Asn Tyr Phe Glu Gly
            355                 360                 365

Arg Pro Asp Gly Trp Gln Thr Met Asp Asp Thr Val Tyr Val Ala Ala
            370                 375                 380

Leu Leu Lys Thr Ala Gly Ser Val Thr Val Thr Ser Gly Gly Thr Thr
385                 390                 395                 400

Gln Thr Phe Gln Ala Asn Ala Gly Ala Asn Leu Phe Gln Ile Pro Ala
            405                 410                 415

Ser Ile Gly Gln Gln Lys Phe Ala Leu Thr Arg Asn Gly Gln Thr Val
            420                 425                 430

Phe Ser Gly Thr Ser Leu Met Asp Ile Thr Asn Val Cys Ser Cys Gly
            435                 440                 445

Ile Tyr Asn Phe Asn Pro Tyr Val Gly Thr Ile Pro Ala Gly Phe Asp
            450                 455                 460

Asp Pro Leu Gln Ala Asp Gly Leu Phe Ser Leu Thr Ile Gly Leu His
465                 470                 475                 480

Val Thr Thr Cys Gln Ala Lys Pro Ser Leu Gly Thr Asn Pro Pro Val
            485                 490                 495

Thr Ser Gly Pro Val Ser Ser Leu Pro Ala Ser Ser Thr Thr Arg Ala
            500                 505                 510
```

```
Ser Ser Pro Pro Val Ser Thr Arg Val Ser Ser Pro Pro Val
        515                 520                 525

Ser Ser Pro Pro Val Ser Arg Thr Ser Ser Ala Pro Pro Pro Gly
    530                 535                 540

Asn Ser Thr Pro Pro Ser Gly Gln Val Cys Val Ala Gly Thr Val Ala
545                 550                 555                 560

Asp Gly Glu Ser Gly Asn Tyr Ile Gly Leu Cys Gln Phe Ser Cys Asn
                565                 570                 575

Tyr Gly Tyr Cys Pro Pro Gly Pro Cys Lys Cys Thr Ala Phe Gly Ala
            580                 585                 590

Pro Ile Ser Pro Pro Ala Ser Asn Gly Arg Asn Gly Cys Pro Leu Pro
        595                 600                 605

Gly Glu Gly Asp Gly Tyr Leu Gly Leu Cys Ser Phe Ser Cys Asn His
    610                 615                 620

Asn Tyr Cys Pro Pro Thr Ala Cys Gln Tyr Cys
625                 630                 635
```

<210> SEQ ID NO 21
<211> LENGTH: 2041
<212> TYPE: DNA
<213> ORGANISM: Trichoderma harzianum

<400> SEQUENCE: 21

```
atgttgggcg ttttccgccg cctcaggctc ggcgcccttg ccgccgcagc tctgtcttct      60
ctcggcagtg ccgctcccgc caatgttgct attcggtctc tcgaggaacg tgcttcttct    120
gctgaccgtc tcgtattctg tcatttcatg attgggatcg tgggtgaccg tggcagctcg    180
gcagattatg atgacgatat gcaacgtgcc aaagccgctg gcattgacgc cttcgccctg    240
aacatcggcg ttgacggcta taccgaccag cagctcggct atgcctatga ctctgccgat    300
cgtaatggca tgaaagtctt catttcattt gatttcaact ggtggagccc cggcaatgca    360
gttggtgttg ccagaagat tgcgcagtat gccaaccgcc ctgcccagct gtatgtcgac     420
aaccggccat tcgcctcttc cttcgccggt gacggtctgg atgtaaatgc gttgcgctct    480
gctgcaggct ccaacgttta ctttgtgccc aacttccacc tggtcaatc ttcccctcc      540 aacattgatg gcgcccttaa ctggatggcc tgggataatg atggaaacaa caaggcaccc    600
aagccgggcc agactgtcac agtggcagac ggtgacaacg cttataagaa ttggttgggt    660
ggcaagcctt acctggcgcc tgtctcaact tgggttttca accatttcgg gcccgaagtt    720
tcatattcca gaactgggt tttcccaagt gggcctctga tctataaccg gtggcaacaa     780
gtcttgcagc aagggttccc aagggttgag atcgttacct ggaatgacta cggggaatct    840
cactacgtcg gtcccctgaa gtctaagcaa tttcatgatg gaactccaa atgggtcaat     900 gatatgcccc acgatggatt cctggatctt tcgaagccgt tcatagccgc atataaaaac    960
agggatcccg acatctccaa gtatgttcaa aatgagcagc ttgtttactg gtaccgccgc   1020
aacttaaagg cactggactg tgacgccacc gacacaacct ctaaccgccc ggctaacaat   1080
ggaagcggca attactttga gggacgcccc gatggttggc aaactatgga tgatacggtt   1140
tacgtggcgg cacttctcaa gactgccggt agcgtcacgg tcacgtctgg tggcaccact   1200
caaacgttcc aggccaacgc cggagccaat ctcttccaaa tcccggccag catcggccag   1260
caaaagtttg ctctgactcg taacggtcag accgtcttta gcggaaccctc attgatggat   1320 atcaccaacg tttgctcttg cggtatctac aacttcaacc catatgttgg caccattcct   1380
gccggctttg acgaccctct tcaggctgac ggtctttttct cttttgaccat cggattgcac   1440
```

-continued

```
gtcacaactt gtcaggccaa gccatctctt ggaactaacc ctcctgtcac ttccggccct    1500
gtgtcctcgc ttccagcttc ctccaccacc cgcgcatcct cgccgcctcc tgtttcttca    1560
actcgtgtct cttctccccc tgtctcttcc cctccagttt ctcgcacctc ttctgccct     1620 ccccctccgg caacagcac gccgccatcg ggtcaggttt gcgttgccgg caccgttgcc     1680
gacggcgagt ctggcaacta catcggcctg tgccaattca gctgcaacta cggttactgc    1740
ccaccaggac cgtgtaagtg caccgccttt ggtgctccca tctcgccacc ggcatccaac    1800
ggccgcaacg gctgccctct gccgggagaa ggcgatggtt atctgggcct gtgcagtttc    1860
agttgtaacc ataattactg cccgccaacg gcatgtcaat actgctagga gggatcaatc    1920
tcagtatgag tatatggagg ctgctgaagg accaattagc tgttcttatc ggcagacgaa    1980
acccatagag taagaagtta aataaaatgc aattaatgtg ttttcaaaaa aaaaaaaaa    2040 a                                                                    2041
```

<210> SEQ ID NO 22
<211> LENGTH: 608
<212> TYPE: PRT
<213> ORGANISM: Penicillium minioluteum

<400> SEQUENCE: 22

```
Met Ala Thr Met Leu Lys Leu Leu Ala Leu Thr Leu Ala Ile Ser Glu
1               5                   10                  15

Ser Ala Ile Gly Ala Val Met His Pro Pro Gly Asn Ser His Pro Gly
            20                  25                  30

Thr His Met Gly Thr Thr Asn Asn Thr His Cys Gly Ala Asp Phe Cys
        35                  40                  45

Thr Trp Trp His Asp Ser Gly Glu Ile Asn Thr Gln Thr Pro Val Gln
    50                  55                  60

Pro Gly Asn Val Arg Gln Ser His Lys Tyr Ser Val Gln Val Ser Leu
65                  70                  75                  80

Ala Gly Thr Asn Asn Phe His Asp Ser Phe Val Tyr Glu Ser Ile Pro
                85                  90                  95

Arg Asn Gly Asn Gly Arg Ile Tyr Ala Pro Thr Asp Pro Pro Asn Ser
            100                 105                 110

Asn Thr Leu Asp Ser Ser Val Asp Asp Gly Ile Ser Ile Glu Pro Ser
        115                 120                 125

Ile Gly Leu Asn Met Ala Trp Ser Gln Phe Glu Tyr Ser His Asp Val
    130                 135                 140

Asp Val Lys Ile Leu Ala Thr Asp Gly Ser Ser Leu Gly Ser Pro Ser
145                 150                 155                 160

Asp Val Val Ile Arg Pro Val Ser Ile Ser Tyr Ala Ile Ser Gln Ser
                165                 170                 175

Asp Asp Gly Gly Ile Val Ile Arg Val Pro Ala Asp Ala Asn Gly Arg
            180                 185                 190

Lys Phe Ser Val Glu Phe Lys Thr Asp Leu Tyr Thr Phe Leu Ser Asp
        195                 200                 205

Gly Asn Glu Tyr Val Thr Ser Gly Gly Ser Val Gly Val Glu Pro
    210                 215                 220

Thr Asn Ala Leu Val Ile Phe Ala Ser Pro Phe Leu Pro Ser Gly Met
225                 230                 235                 240

Ile Pro His Met Thr Pro Asp Asn Thr Gln Thr Met Thr Pro Gly Pro
                245                 250                 255
```

```
Ile Asn Asn Gly Asp Trp Gly Ala Lys Ser Ile Leu Tyr Phe Pro Pro
                260                 265                 270

Gly Val Tyr Trp Met Asn Gln Asp Gln Ser Gly Asn Ser Gly Lys Leu
            275                 280                 285

Gly Ser Asn His Ile Arg Leu Asn Ser Asn Thr Tyr Trp Val Tyr Leu
        290                 295                 300

Ala Pro Gly Ala Tyr Val Lys Gly Ala Ile Glu Tyr Phe Thr Lys Gln
305                 310                 315                 320

Asn Phe Tyr Ala Thr Gly His Gly Ile Leu Ser Gly Glu Asn Tyr Val
                325                 330                 335

Tyr Gln Ala Asn Ala Gly Asp Asn Tyr Ile Ala Val Lys Ser Asp Ser
            340                 345                 350

Thr Ser Leu Arg Met Trp Trp His Asn Asn Leu Gly Gly Gln Thr
        355                 360                 365

Trp Tyr Cys Val Gly Pro Thr Ile Asn Ala Pro Pro Phe Asn Thr Met
    370                 375                 380

Asp Phe Asn Gly Asn Ser Gly Ile Ser Ser Gln Ile Ser Asp Tyr Lys
385                 390                 395                 400

Gln Val Gly Ala Phe Phe Gln Thr Asp Gly Pro Glu Ile Tyr Pro
                405                 410                 415

Asn Ser Val Val His Asp Val Phe Trp His Val Asn Asp Asp Ala Ile
            420                 425                 430

Lys Ile Tyr Tyr Ser Gly Ala Ser Val Ser Arg Ala Thr Ile Trp Lys
        435                 440                 445

Cys His Asn Asp Pro Ile Ile Gln Met Gly Trp Thr Ser Arg Asp Ile
450                 455                 460

Ser Gly Val Thr Ile Asp Thr Leu Asn Val Ile His Thr Arg Tyr Ile
465                 470                 475                 480

Lys Ser Glu Thr Val Val Pro Ser Ala Ile Ile Gly Ala Ser Pro Phe
                485                 490                 495

Tyr Ala Ser Gly Met Ser Pro Asp Ser Arg Lys Ser Ile Ser Met Thr
            500                 505                 510

Val Ser Asn Val Val Cys Glu Gly Leu Cys Pro Ser Leu Phe Arg Ile
        515                 520                 525

Thr Pro Leu Gln Asn Tyr Lys Asn Phe Val Val Lys Asn Val Ala Phe
530                 535                 540

Pro Asp Gly Leu Gln Thr Asn Ser Ile Gly Thr Gly Glu Ser Ile Ile
545                 550                 555                 560

Pro Ala Ala Ser Gly Leu Thr Met Gly Leu Asn Ile Ser Asn Trp Thr
                565                 570                 575

Val Gly Gly Gln Lys Val Thr Met Glu Asn Phe Gln Ala Asn Ser Leu
            580                 585                 590

Gly Gln Phe Asn Ile Asp Gly Ser Tyr Trp Gly Glu Trp Gln Ile Ser
        595                 600                 605

<210> SEQ ID NO 23
<211> LENGTH: 3629
<212> TYPE: DNA
<213> ORGANISM: Penicillium minioluteum

<400> SEQUENCE: 23
ggcatagtaa tcccgacagc cgagtatgat ggagcttctt cggataatga tagcgccacc      60
agaccttgct tgagctggag agctaaaaca ttaaacgcca cacgaccaac actctcatta    120
gttgcgatag atgatgctcg gagctgttga aactcagaaa ttccttctat gcggggtctc    180
```

```
caagatcgat cctgggggat gtgaatacta cggtggacct aattgacgcc ttgacaggtg    240
atgttaagcg aaccaaggaa gaataatctg gggctagatg aagatgttga gctgtaaggt    300
acggtacgtt cctattggct ttatcggagc ttctccgggt tactcagtct ttccgggagc    360
atgatcattt ttgtattgtc caatagtaag cagaaactga gagccaccac aaactcaaaa    420
cctcggtagc gaagtttccc ggaaccagtc aggattctca gaaactgtgc tcgtgttgcg    480
gggaatccgc attctacgtc gtctggagca aggaaatgtt cgtgctggat tgaggaggat    540
aggtaggttg gagaatctct tcagctaacc aatctataag catgctccgg taacctttag    600
agtttcacat tcaacgtaat ttccaagata gccagagcgt ccttgaatta ctatgtagaa    660
atcctaaaat ttcccctgta aaatgcaagt caacgagatg cgtgccctca atgtctctcg    720
gcgctacccc ggaaatgatg cataaggcca agaatgtcac ccggtaactt tttcttcaga    780
atatcctaag atttccatca aacacagtcg aataggtcaa tgctcgcgag agactttctg    840
ccttcactct acgtcctact catagaagtt caacggctca attccggggt aatctagagt    900
ttggacctca agggagatgt tgcaacaaat tgtactagaa cgatgcgctt gctttccaat    960
acagtagttg acttcatata gcttccaaca aagggatggg gatgaaggc tctatagcga   1020 gaagtctata agaaagtgtc ctcatacctg tatctctcag tcgttcgaga acaatcccgg   1080
aaactatctt atcttgcgag aaagaagaca atatctcaaa cttatggcca caatgctaaa   1140
gctacttgcg ttgacccttg caattagcga gtccgccatt ggagcagtca tgcacccacc   1200
tggcaattct catcccggta cccatatggg cactacgaat aatacccatt gcggcgccga   1260
tttctgtacc tggtggcatg attcagggga gatcaatacg cagacacctg tccaaccagg   1320
gaacgtgcgc caatctcaca agtattccgt gcaagtgagc ctagctggta caaacaattt   1380
tcatgactcc tttgtatatg aatcgatccc ccggaacgga aatggtcgca tctatgctcc   1440
caccgatcca cccaacagca acacactaga ttcaagtgtg gatgatggaa tctcgattga   1500
gcctagtatc ggccttaata tggcatggtc ccaattcgag tacagccacg atgtagatgt   1560
aaagatcctg gccactgatg gctcatcgtt gggctcgcca agtgatgttg ttattcgccc   1620
cgtctcaatc tcctatgcga tttctcagtc tgacgatggt gggattgtca tccgggtccc   1680
agccgatgcg aacggccgca aattttcagt tgagttcaaa actgacctgt acacattcct   1740
ctctgatggc aacgagtacg tcacatcggg aggcagcgtc gtcggcgttg agcctaccaa   1800
cgcacttgtg atcttcgcaa gtccgtttct tccttctggc atgattcctc atatgacacc   1860
cgacaacacg cagaccatga cgccaggtcc tatcaataac ggcgactggg cgccaagtc   1920 aattctttac ttcccaccag gtgtatactg gatgaaccaa gatcaatcgg gcaactcggg   1980
gaagttagga tctaatcata tacgtctaaa ctcgaacact tactgggtct accttgcccc   2040
cggtgcgtac gtgaagggtg ctatagagta ttttaccaag cagaacttct atgcaactgg   2100
tcatggtatc ctatcgggtg aaaactatgt ttaccaagcc aatgccggcg acaactacat   2160
tgcagtcaag agcgattcaa ccagcctccg gatgtggtgg cacaataacc ttgggggtgg   2220
tcaaacatgg tactgcgttg gcccgacgat caatgcgcca ccattcaata ctatggattt   2280
caatggaaat tctggcatct caagtcaaat tagcgactat aagcaggtgg agccttctt   2340 cttccagacg gatggaccag aaatatatcc caatagtgtc gtgcacgacg tcttctggca   2400
cgtcaatgat gatgcaatca aaatctacta ttcgggagca tctgtatcgc gggcaacgat   2460
ctggaaatgt cacaatgacc caatcatcca gatgggatgg acgtctcggg atatcagtgg   2520
```

```
agtgacaatc gacacattaa atgttattca cacccgctac atcaaatcgg agacggtggt    2580
gccttcggct atcattgggg cctctccatt ctatgcaagt gggatgagtc ctgattcaag    2640
aaagtccata tccatgacgg tttcaaacgt tgtttgcgag ggtctttgcc cgtccctatt    2700
ccgcatcaca ccccttcaga actacaaaaa ttttgttgtc aaaaatgtgg ctttcccaga    2760
cgggctacag acgaatagta ttggcacagg agaaagcatt attccagccg catctggtct    2820
aacgatggga ctgaatatct ccaactggac tgttggtgga caaaaagtga ctatggagaa    2880 cttttcaagcc aatagcctgg ggcagttcaa tattgacggc agctattggg gggagtggca    2940
gattagctga attccagctc tcggagcgcg tgagtgcttc tacccgctcc tttacccttg    3000
tcgagagata aaggcataag ttagctcatg tgaaggcgat ttcagttcat tctctctttt    3060
tggagcttat ttcctgttcg accaattgtg acaccaactt gcctttcaaa agacgtggac    3120
gatatgtgta cggtaatcag tcaaatgaac gtcaacattc atttaataag gacatttcca    3180
ggtttcctta ctctgtcgat tatgcctaac tcgggttgat gtcttgtcag gatggaaaat    3240
ctcgttgtgt acttccagtg aaatgggcag ggctaagccc taaaccctaa cgcatacaat    3300
ttgtaggcac ctacccatgt aagttcacac ccagtcgact tataagtcta gatatttatg    3360
ctatgcaggc tctggaatga tttacattcc atgctataca tagttatttg caagaatttg    3420
cagacgagat aaaaatcaat ggacgaataa tcacgcatta ctccacaggc tcatgccacg    3480
gagcaagggt tcccccgaat ctaggccaga ccggatgatg attcaaccga ttcttttgc     3540 agtaactatc tccgtacgag ctgcacgagc taaacggatt atataaaggt gctaactgag    3600
cattggatcc gtcagttata tgaaatgca                                       3629
```

<210> SEQ ID NO 24
<211> LENGTH: 608
<212> TYPE: PRT
<213> ORGANISM: Penicillium aculeatum

<400> SEQUENCE: 24

```
Met Ala Thr Met Leu Lys Leu Leu Thr Leu Ala Leu Ala Ile Ser Glu
1               5                   10                  15

Ser Ala Ile Gly Ala Val Leu His Pro Gly Ser Ser His Pro Ser
                20                  25                  30

Thr Arg Thr Asp Thr Thr Asn Asn Thr His Cys Gly Ala Asp Phe Cys
            35                  40                  45

Thr Trp Trp His Asp Ser Gly Glu Ile Asn Thr Gln Thr Pro Val Gln
        50                  55                  60

Pro Gly Asn Val Arg Gln Ser His Lys Tyr Ser Val Gln Val Ser Leu
65                  70                  75                  80

Ala Gly Ala Asn Asn Phe Gln Asp Ser Phe Val Tyr Glu Ser Ile Pro
                85                  90                  95

Arg Asn Gly Asn Gly Arg Ile Tyr Ala Pro Thr Asp Pro Asn Ser
            100                 105                 110

Asn Thr Leu Asp Ser Ser Val Asp Asp Gly Ile Ser Ile Glu His Ser
        115                 120                 125

Ile Gly Leu Asn Met Ala Trp Ser Gln Phe Glu Tyr Ser Gln Asp Val
    130                 135                 140

Asp Ile Lys Ile Leu Ala Ala Asp Gly Ser Ser Leu Gly Ser Pro Ser
145                 150                 155                 160

Asp Val Val Ile Arg Pro Val Ser Ile Ser Tyr Ala Ile Ser Gln Ser
                165                 170                 175
```

-continued

Asp Asp Gly Gly Ile Val Ile Arg Val Pro Ala Asp Ala Asn Gly Arg
            180                 185                 190

Lys Phe Ser Val Glu Phe Lys Asn Asp Pro Tyr Thr Phe Leu Ser Asp
        195                 200                 205

Gly Asn Glu Tyr Val Thr Ser Gly Gly Ser Val Val Gly Val Glu Pro
    210                 215                 220

Thr Asn Ala Leu Val Ile Phe Ala Ser Pro Phe Leu Pro Ser Gly Met
225                 230                 235                 240

Ile Pro His Met Thr Pro Asp Asn Thr Gln Thr Met Thr Pro Gly Pro
                245                 250                 255

Ile Asn Asn Gly Asp Trp Gly Ser Lys Ser Ile Leu Tyr Phe Pro Pro
            260                 265                 270

Gly Val Tyr Trp Met Asn Gln Asp Gln Ser Gly Asn Ser Gly Lys Leu
        275                 280                 285

Gly Ser Asn His Ile Arg Leu Asn Ser Asn Thr Tyr Trp Val Tyr Phe
    290                 295                 300

Ala Pro Gly Ala Tyr Val Lys Gly Ala Ile Glu Tyr Phe Thr Lys Gln
305                 310                 315                 320

Asn Phe Tyr Ala Thr Gly His Gly Val Leu Ser Gly Glu Asn Tyr Val
                325                 330                 335

Tyr Gln Ala Asn Ala Gly Glu Asn Tyr Val Ala Val Lys Ser Asp Ser
            340                 345                 350

Thr Ser Leu Arg Met Trp Trp His Asn Asn Leu Gly Gly Gln Thr
        355                 360                 365

Trp Tyr Cys Val Gly Pro Thr Ile Asn Ala Pro Pro Phe Asn Thr Met
    370                 375                 380

Asp Phe Asn Gly Asn Ser Gly Ile Ser Ser Gln Ile Ser Asp Tyr Lys
385                 390                 395                 400

Gln Val Gly Ala Phe Phe Gln Thr Asp Gly Pro Glu Ile Tyr Pro
                405                 410                 415

Asn Ser Val Val His Asp Val Phe Trp His Val Asn Asp Asp Ala Ile
            420                 425                 430

Lys Ile Tyr Tyr Ser Gly Ala Ser Val Ser Arg Ala Thr Ile Trp Lys
        435                 440                 445

Cys His Asn Asp Pro Ile Ile Gln Met Gly Trp Thr Ser Arg Asp Ile
    450                 455                 460

Ser Gly Val Thr Ile Asp Thr Leu Asn Val Ile His Thr Arg Tyr Ile
465                 470                 475                 480

Lys Ser Glu Thr Val Val Pro Ser Ala Ile Gly Ala Ser Pro Phe
                485                 490                 495

Tyr Ala Ser Gly Met Ser Pro Asp Ser Ser Lys Ser Ile Ser Met Thr
            500                 505                 510

Val Ser Asn Val Val Cys Glu Gly Leu Cys Pro Ser Leu Phe Arg Ile
        515                 520                 525

Thr Pro Leu Gln Asn Tyr Lys Asn Phe Val Val Lys Asn Val Ala Phe
    530                 535                 540

Pro Asp Gly Leu Gln Thr Asn Ser Ile Gly Thr Gly Glu Ser Ile Ile
545                 550                 555                 560

Pro Ala Ala Ser Gly Leu Thr Met Gly Leu Asp Ile Ser Asn Trp Ser
                565                 570                 575

Val Gly Gly Gln Lys Val Thr Met Gln Asn Phe Gln Ala Asn Ser Leu
            580                 585                 590

Gly Gln Phe Asp Ile Asp Gly Ser Tyr Trp Gly Glu Trp Gln Ile Asn

<210> SEQ ID NO 25
<211> LENGTH: 1888
<212> TYPE: DNA
<213> ORGANISM: Penicillium aculeatum

<400> SEQUENCE: 25

```
atggccacaa tgctaaagct acttacgttg gcccttgcaa ttagcgagtc tgccattgga      60
gcagtcctgc acccacctgg cagttctcat cccagtaccc gtacggacac tacgaataat     120
acccattgcg gtgccgactt ctgtacctgg tggcatgatt caggcgagat caacacacag     180
acacctgtcc aaccggggaa cgtgcgccaa tctcacaagt attccgtaca agtgagccta     240
gctggtgcga caactttca ggactccttt gtatatgaat cgatccctcg gaacggaaat      300
ggtcgcatct atgctcccac cgatccaccc aacagcaaca cactagattc aagtgttgat     360
gatggaatct cgattgaaca tagtattggc ctcaatatgg catggtccca attcgagtac     420
agccaggatg tcgatataaa gatcctggcc gctgatggct catcgttggg ctcaccaagt     480
gatgttgtta ttcgccccgt ctcaatctcc tatgcaattt ctcaatccga cgatggcgga     540
attgtcattc gggtcccagc cgatgcgaac ggccgcaaat tttcagtcga gttcaaaaat     600
gacccgtaca cgttcctctc tgacggcaac gagtacgtca catcgggagg cagcgttgtc     660
ggcgttgagc ctaccaacgc acttgtgatc ttcgcaagcc cgtttcttcc gtcaggcatg     720
attcctcata tgacacccga caacacgcag accatgacac caggacctat caataacggc     780
gactggggct ccaagtcaat tctttatttc ccaccgggcg tatactggat gaaccaagat     840
caatcaggca actcggggaa attaggatct aatcatatac gcctgaactc gaacacctac     900
tgggtctact ttgccccagg tgcgtacgtg aagggtgcta tagagtattt caccaagcag     960
aacttctatg caactggtca tggtgtccta tcgggtgaaa actatgttta ccaagccaat    1020
gctggcgaaa actacgttgc ggtcaagagc gattcgacta gcctccggat gtggtggcac    1080
aataacctgg gaggtggaca acatggtac tgcgttgggc ctacgatcaa tgcgccgcca    1140
tttaacacaa tggattttcaa tggaaattcc ggtatctcaa gtcaaattag cgactataag    1200
caggtgggag ctttcttctt tcagacggat ggaccagaaa tttatcccaa tagtgtcgtg    1260
cacgacgtct tctggcatgt caatgatgat gcaatcaaaa tctactattc cggagcatct    1320
gtctcgcggg caacgatctg gaaatgtcac aacgatccaa tcatccagat gggatggacg    1380
tctcgggata tcagtggagt gacaatcgac acattgaatg tcatccacac cgctacatc    1440
aagtcggaga cggtggtgcc ttcggctatc attggggctt ctccattcta tgcaagtggg    1500
atgagtcctg attcaagcaa gtctatatcc atgacggttt caaacgttgt ctgcgaggga    1560
ctttgcccgt ctctgttccg aatcacacct ttacagaact acaagaattt tgttgtcaaa    1620
aatgtggctt tcccagatgg gctacagacg aatagtattg gcacgggaga aagcattatt    1680
ccagccgcat ctggtctaac gatgggactg gatatctcca actggtctgt tggtggtcag    1740
aaggtgacta tgcagaactt tcaagccaat agtctggggc aattcgacat tgacggcagc    1800
tattggggg agtggcagat taactagctg aataatattg cagcttttcag ggcgcatgag    1860
tgcttgtacc cgctcctta cccttgtc                                        1888
```

<210> SEQ ID NO 26
<211> LENGTH: 615
<212> TYPE: PRT
<213> ORGANISM: Penicillium funiculosum

<400> SEQUENCE: 26

Met Ala Thr Met Leu Lys Leu Leu Ala Leu Thr Leu Ala Ile Ser Glu
1               5                   10                  15

Ser Ala Ile Gly Ala Val Met His Pro Pro Gly Val Ser His Pro Gly
            20                  25                  30

Thr His Thr Gly Thr Thr Asn Asn Thr His Cys Gly Ala Asp Phe Cys
            35                  40                  45

Thr Trp Trp His Asp Ser Gly Glu Ile Asn Thr Gln Thr Pro Val Gln
50                  55                  60

Pro Gly Asn Val Arg Gln Ser His Lys Tyr Ser Val Gln Val Ser Leu
65                  70                  75                  80

Ala Gly Thr Asn Asn Phe His Asp Ser Phe Val Tyr Glu Ser Ile Pro
            85                  90                  95

Arg Asn Gly Asn Gly Arg Ile Tyr Ala Pro Thr Asp Pro Ser Asn Ser
            100                 105                 110

Asn Thr Leu Asp Ser Ser Val Asp Asp Gly Ile Ser Ile Glu Pro Ser
            115                 120                 125

Ile Gly Leu Asn Met Ala Trp Ser Gln Phe Glu Tyr Ser Gln Asp Val
130                 135                 140

Asp Ile Lys Ile Leu Ala Thr Asp Gly Ser Ser Leu Gly Ser Pro Ser
145                 150                 155                 160

Asp Val Val Ile Arg Pro Val Ser Ile Ser Tyr Ala Ile Ser Gln Ser
                165                 170                 175

Asn Asp Gly Gly Ile Val Ile Arg Val Pro Ala Asp Ala Asn Gly Arg
            180                 185                 190

Lys Phe Ser Val Glu Phe Lys Asn Asp Leu Tyr Thr Phe Leu Ser Asp
            195                 200                 205

Gly Asn Glu Tyr Val Thr Ser Gly Gly Ser Val Val Gly Val Glu Pro
210                 215                 220

Thr Asn Ala Leu Val Ile Phe Ala Ser Pro Phe Leu Pro Ser Gly Met
225                 230                 235                 240

Ile Pro His Met Lys Pro His Asn Thr Gln Thr Met Thr Pro Gly Pro
                245                 250                 255

Ile Asn Asn Gly Asp Trp Gly Ala Lys Ser Ile Leu Tyr Phe Pro Pro
            260                 265                 270

Gly Val Tyr Trp Met Asn Gln Asp Gln Ser Gly Asn Ser Gly Lys Leu
            275                 280                 285

Gly Ser Asn His Ile Arg Leu Asn Ser Asn Thr Tyr Trp Val Tyr Leu
            290                 295                 300

Ala Pro Gly Ala Tyr Val Lys Gly Ala Ile Glu Tyr Phe Thr Lys Gln
305                 310                 315                 320

Asn Phe Tyr Ala Thr Gly His Gly Val Leu Ser Gly Glu Asn Tyr Val
                325                 330                 335

Tyr Gln Ala Asn Ala Gly Asp Asn Tyr Val Ala Val Lys Ser Asp Ser
            340                 345                 350

Thr Ser Leu Arg Met Trp Trp His Asn Asn Leu Gly Gly Gln Thr
            355                 360                 365

Trp Tyr Cys Val Gly Pro Thr Ile Asn Ala Pro Phe Asn Thr Met
            370                 375                 380

Asp Phe Asn Gly Asn Ser Gly Ile Ser Gln Ile Ser Asp Tyr Lys Gln
385                 390                 395                 400

Val Gly Ala Phe Phe Phe Gln Thr Asp Gly Pro Glu Ile Tyr Pro Asn

|   | 405 |   |   |   |   | 410 |   |   |   |   | 415 |   |   |
|---|---|---|---|---|---|---|---|---|---|---|---|---|---|
| Ser | Val | Val | His | Asp | Val | Phe | Trp | His | Val | Asn | Asp | Ala | Ile | Lys |
|   |   |   | 420 |   |   |   |   | 425 |   |   |   | 430 |   |   |

Ile Tyr Tyr Ser Gly Ala Ser Val Ser Arg Ala Thr Ile Trp Lys Cys
        435                 440                 445

His Asn Asp Pro Ile Ile Gln Met Gly Trp Thr Ser Arg Asp Ile Ser
    450                 455                 460

Gly Val Thr Ile Asp Thr Leu Asn Val Ile His Thr Arg Tyr Ile Lys
465                 470                 475                 480

Ser Glu Thr Val Val Pro Ser Ala Ile Ile Gly Ala Ser Pro Phe Tyr
            485                 490                 495

Ala Ser Gly Met Ser Pro Asp Ser Ser Lys Ser Ile Ser Met Thr Val
        500                 505                 510

Ser Asn Val Val Cys Glu Gly Leu Cys Pro Ser Leu Phe Arg Ile Thr
    515                 520                 525

Pro Leu Gln Asn Tyr Lys Asn Phe Val Val Lys Asn Val Ala Phe Pro
530                 535                 540

Asp Gly Leu Gln Thr Asn Ser Ile Gly Thr Gly Glu Ser Ile Ile Pro
545                 550                 555                 560

Ala Ala Ser Gly Leu Thr Met Gly Leu Asn Ile Ser Ser Trp Thr Val
            565                 570                 575

Gly Gly Gln Lys Val Thr Met Glu Asn Phe Gln Ala Asn Ser Leu Gly
        580                 585                 590

Gln Phe Asn Ile Asp Gly Ser Tyr Trp Gly Glu Trp Gln Ile Ser Arg
    595                 600                 605

Ile Ser Ser Ser Gln Ser Ala
    610                 615

<210> SEQ ID NO 27
<211> LENGTH: 2225
<212> TYPE: DNA
<213> ORGANISM: Penicillium funiculosum

<400> SEQUENCE: 27

| atggccacaa tgctaaagct acttgcgttg acccttgcaa ttagcgagtc cgccattgga | 60 |
| gcagtcatgc acccacctgg cgtttctcat cccggtaccc atacgggcac tacgaataat | 120 |
| acccattgcg gcgccgactt ctgtacctgg tggcatgatt caggggagat caacacgcag | 180 |
| acacctgtcc aaccagggaa cgtgcgccaa tctcacaagt attccgtgca agtgagtcta | 240 |
| gctggtacaa caactttca tgactccttt gtatatgaat cgatccccg gaacggaaat | 300 |
| ggtcgcatct atgctcccac cgatccatcc aacagcaaca cattagattc aagcgtggat | 360 |
| gatggaatct cgattgagcc tagtatcggc ctcaatatgg catggtccca attcgagtac | 420 |
| agccaggatg tcgatataaa gatcctggca actgatggct catcgttggg ctcaccaagt | 480 |
| gatgttgtta ttcgccccgt ctcaatctcc tatgcgattt ctcagtccaa cgatggcggg | 540 |
| attgtcatcc gggtcccagc cgatgcgaac ggccgcaaat tttcagtcga attcaaaaat | 600 |
| gacctgtaca ctttcctctc tgatggcaac gagtacgtca tcgggagg tagcgtcgtc | 660 |
| ggcgttgagc ctaccaacgc acttgtgatc ttcgcaagtc cgtttcttcc ttctggcatg | 720 |
| attcctcata tgaaaccca caacacgcag accatgacgc aggtcctat caataacggc | 780 |
| gactggggcg ccaagtcaat tctttacttc ccaccaggtg tatactggat gaaccaagat | 840 |
| caatcgggca actcgggtaa attaggatct aatcatatac gtctaaactc gaacacttac | 900 |

```
tgggtctacc ttgcccccgg tgcgtacgtg aagggtgcta tagagtattt caccaagcaa    960
aacttctatg caactggtca tggtgtccta tcaggtgaaa actatgttta ccaagccaat   1020
gctggcgaca actatgttgc agtcaagagc gattcgacca gcctccggat gtggtggcac   1080
aataaccttg ggggtggtca aacatggtac tgcgttggcc cgacgatcaa tgcgccacca   1140
ttcaacacta tggatttcaa tggaaattct ggcatctcaa gtcaaattag cgactataag   1200
caggtgggag ccttcttctt ccagacggat ggaccagaaa tctatcccaa tagtgtcgtg   1260
cacgacgtct tctggcacgt caatgatgat gcaatcaaaa tctactattc gggagcatct   1320
gtatcgcggg caacgatctg gaaatgtcac aatgacccaa tcatccagat gggatggaca   1380
tctcgggata tcagtggagt gacaatcgac acattaaatg ttattcacac ccgctacatc   1440
aaatcggaga cggtggtgcc ttcggctatc attgggcct  ctccattcta tgcaagtggg   1500
atgagtcccg attcaagcaa gtccatatcc atgacggttt caaacgttgt ttgcgagggt   1560
ctttgcccgt ccctgttccg catcacaccc ctacagaact acaaaaattt tgttgtcaaa   1620
aatgtggctt tcccagatgg gctacagaca aatagtattg gcacaggaga aagcattatt   1680
ccagccgcat ctggtctaac gatgggacta aatatctcca gctggactgt tggtggacaa   1740
aaagtgacaa tggagaactt tcaagccaat agcctggggc agttcaatat tgacggcagc   1800
tattgggggg agtggcagat tagtcgaatt tccagctctc agagcgcgtg agtgcttcta   1860
cccgctcctt tacccttgtc gaaggatcaa ggcataagtt agctcatgtg aaggcgattt   1920
cagttcattc tctctttttt ggagctcatt tcctttcga ccaattgtga caccaaattg   1980
ccatgtgtac tgtaattggt caaatgaacg ttaaccttcg atttaatatg gacatttcca   2040
ggtttcctta ctctgtcgat tatgcctaac tcgggttgat gtcttgtcag gatgaaaatc   2100
tcgttgtcat gtacttcgag tgaaatgggc agggctaacc cctaagccct aacgcccaat   2160
cgacttataa gtctagatgt ttatgctatg caggctctgg aatgatttac attccatgct   2220
ataca                                                               2225
```

<210> SEQ ID NO 28
<211> LENGTH: 21
<212> TYPE: PRT
<213> ORGANISM: Artificial Sequence
<220> FEATURE:
<223> OTHER INFORMATION: CSP

<400> SEQUENCE: 28

```
Ser Gly Ser Leu Ser Thr Phe Phe Arg Leu Phe Asn Arg Ser Phe Thr
1               5                   10                  15

Gln Ala Leu Gly Lys
            20
```

What is claimed is:

1. A multi-component composition comprising freeze dried plant leaves harboring a nucleic acid encoding at least one antimicrobial peptide (AMP) operably linked to a nucleic acid encoding a mutanase enzyme of SEQ ID NO: 1 for production of an AMP-mutanase fusion protein, said AMP and mutanase enzyme acting synergistically to degrade biofilm structures and inhibit biofilm deposition, said composition comprising a biologically acceptable carrier for delivery of said composition.

2. The composition as claimed in claim 1 wherein the AMP encoding nucleic acid encodes an AMP selected from protegrin 1 (PG-1), RC-101 CSP, CSPC16, G2, C16G2, CSPM8, M8G2, S6L3-33, C16-33 and M8-33.

3. The composition as claimed in claim 1 wherein the composition further comprises at least one of nucleic acid encoding glucoamylase, glucanase, deoxyribonuclease I, DNAase, dispersin B, glycoside hydrolases, and enzymes encoded by SEQ ID NOS: 12, 14, 16, 18, 20, 24, and 26.

4. The composition as claimed in claim 1 wherein said AMP and said mutanase encoding nucleic acids are produced recombinantly.

5. The composition of claim 1, wherein said AMP is PG-1, and said composition further comprises a nucleic acid encoding PG-1 operably linked to a dextranase of SEQ ID NO: 2.

6. The composition of claim 5 wherein the dextranase to mutanase ratio in said composition is 5:1.

7. The composition of claim 6 further comprising glucoamylase.

8. The composition as claimed in claim 1 further comprising an antimicrobial/antibiotic.

9. The composition as claimed in claim 1, further comprising fluoride and/or chlorhexidine (CHX).

10. The composition of claim 1, wherein said carrier is chewing gum.

11. The composition of claim 1, wherein said carrier is an oral rinse.

12. The composition of claim 1, wherein said carrier is a biologically compatible buffer.

13. A chewing gum comprising the composition of claim 1.

14. An oral rinse comprising the composition of claim 1.

15. The oral rinse of claim 11, comprising 0.064% thymol, 0.06% methyl salicylate, 0.042% menthol, 0.092% eucalyptol, 20-30% ethanol, water, benzoic acid, poloxamer 407, sodium benzoate, and caramel.

16. A method of degrading and/or removing biofilm comprising contacting a surface harboring said biofilm with the multicomponent composition of claim 1, said composition having a bactericidal effect, and synergistically reducing or eliminating said biofilm comprising one or more undesirable microorganisms, wherein when said biofilm is present in or on a subject in need of said reduction or elimination.

17. A method of degrading and/or removing biofilm comprising contacting a surface harboring said biofilm with the multicomponent composition of claim 5, said composition having a bactericidal effect, and synergistically reducing or eliminating said biofilm comprising one or more undesirable microorganisms, wherein when said biofilm is present in or on a subject in need of said reduction or elimination.

18. A method of degrading and/or removing biofilm comprising contacting a surface harboring said biofilm with the multicomponent composition of claim 6, said composition having a bactericidal effect, and synergistically reducing or eliminating said biofilm comprising one or more undesirable microorganisms, wherein when said biofilm is present in or on a subject in need of said reduction or elimination.

19. The method of claim 16, wherein said biofilm is present in the mouth.

20. The method of claim 16, wherein said biofilm is present on an implanted medical device.

21. The method of claim 16, wherein the biofilm is present in an internal or external body surface selected from the group consisting of a surface in a urinary tract, a middle ear, a prostate, vascular intima, heart valves, skin, scalp, nails, teeth and an interior of a wound.

22. The composition of claim 1, wherein said AMP and said enzyme are produced in a plant plastid, said composition further comprising a plant remnant.

23. The composition of claim 5, wherein said plant leaves are from a tobacco or a lettuce plant.

24. The composition of claim 6, wherein said at least one AMP and said at least one mutanase enzyme are expressed in a lettuce plant as a fusion protein.

25. The composition of claim 1, wherein said biofilm is present in the mouth.

26. The composition of claim 5, wherein said carrier is chewing gum.

* * * * *